US009901340B2

(12) United States Patent
Smith et al.

(10) Patent No.: US 9,901,340 B2
(45) Date of Patent: *Feb. 27, 2018

(54) ACTIVE BRAKING ELECTRICAL SURGICAL INSTRUMENT AND METHOD FOR BRAKING SUCH AN INSTRUMENT

(71) Applicant: Ethicon Endo-Surgery, Inc., Cincinnati, OH (US)

(72) Inventors: Kevin W. Smith, Coral Gables, FL (US); Thomas O. Bales, Jr., Coral Gales, FL (US); Derek Dee Deville, Coral Gables, FL (US); Carlos Rivera, Cooper City, FL (US); Matthew A. Palmer, Miami, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 714 days.

This patent is subject to a terminal disclaimer.

(21) Appl. No.: 13/847,971

(22) Filed: Mar. 20, 2013

(65) Prior Publication Data

US 2013/0221061 A1    Aug. 29, 2013

Related U.S. Application Data

(60) Division of application No. 11/705,381, filed on Feb. 12, 2007, now Pat. No. 8,038,046, and a division of
(Continued)

(51) Int. Cl.
*A61B 17/068* (2006.01)
*A61B 17/072* (2006.01)
(Continued)

(52) U.S. Cl.
CPC .......... *A61B 17/072* (2013.01); *A61B 17/068* (2013.01); *A61B 17/115* (2013.01);
(Continued)

(58) Field of Classification Search
CPC  A61B 2017/00017; A61B 2017/00398; A61B 2017/00734; A61B 2019/302; A61B 2019/464
(Continued)

(56) References Cited

U.S. PATENT DOCUMENTS 2,533,494 A    12/1950    Mitchell, Jr.
2,588,006 A    3/1952    Hufnagel
(Continued)

FOREIGN PATENT DOCUMENTS

CA    2168693 A1    10/1996
CA    2359426 A1    4/2002
(Continued)

OTHER PUBLICATIONS wikipedia.org Entry for "SWITCH", archived version dated Jan. 31, 2006, URL: http://en.wikipedia.org/w/index/php?title=Switch &oldid=3746595.*
(Continued)

*Primary Examiner* — Hemant M Desai
*Assistant Examiner* — Valentin Neacsu
(74) *Attorney, Agent, or Firm* — Mayback & Hoffman, P.A.; Gregory L. Mayback; Rebecca A. Tie

(57) ABSTRACT

An electrically powered surgical instrument includes a surgical end effector having a surgical procedure effecting actuation assembly. A handle is coupled with the end effector. An electric motor is disposed within a shell of the handle and has power terminals and a drive train actuating the assembly when the motor is supplied with power. A break-before-make power supply switch at the handle selectively controls supply of power to the motor. A post-termination braking circuit electrically short-circuits the power terminals when the switch does not supply power to the motor. A method for post-termination braking of an electrical motor
(Continued)

utilizes the permanent magnetic field of the motor to counteract an inertia-induced over-stroke characteristic of the motor, drive train, and/or actuation assembly after powered operation by short-circuiting the still-spinning motor to create an electrically generated magnetic field in opposition to the permanent magnetic field upon ceasing supply of power to the motor.

14 Claims, 31 Drawing Sheets

Related U.S. Application Data application No. 11/705,246, filed on Feb. 12, 2007, now Pat. No. 8,028,885, and a division of application No. 11/705,334, filed on Feb. 12, 2007, now Pat. No. 8,573,462, and a division of application No. 11/750,622, filed on May 18, 2007, now Pat. No. 7,479,608, and a division of application No. 12/102,464, filed on Apr. 14, 2008, now Pat. No. 8,286,846, and a division of application No. 12/102,181, filed on Apr. 14, 2008, now Pat. No. 8,573,459, and a continuation-in-part of application No. 12/270,518, filed on Nov. 13, 2008, now Pat. No. 7,714,239, and a division of application No. 12/612,525, filed on Nov. 4, 2009, now Pat. No. 8,627,993, and a continuation-in-part of application No. 12/728,471, filed on Mar. 22, 2010, now Pat. No. 8,269,121, and a division of application No. 12/793,962, filed on Jun. 4, 2010, now Pat. No. 9,681,873, and a division of application No. 13/229,076, filed on Sep. 9, 2011, now Pat. No. 8,292,157, and a continuation-in-part of application No. 13/571,159, filed on Aug. 9, 2012, now Pat. No. 8,592,700, and a division of application No. 13/611,881, filed on Sep. 12, 2012, now Pat. No. 8,827,138, and a division of application No. 13/622,819, filed on Sep. 19, 2012, now Pat. No. 9,687,234.

(51) Int. Cl.
  *A61B 17/115* (2006.01)
  *A61B 17/11* (2006.01)
  *A61B 17/00* (2006.01)
  *A61B 90/00* (2016.01)

(52) U.S. Cl.
  CPC ..... *A61B 17/1155* (2013.01); *A61B 17/07207* (2013.01); *A61B 17/1114* (2013.01); *A61B 2017/00017* (2013.01); *A61B 2017/00398* (2013.01); *A61B 2017/00734* (2013.01); *A61B 2017/07285* (2013.01); *A61B 2090/032* (2016.02); *A61B 2090/064* (2016.02)

(58) Field of Classification Search
  USPC ............... 227/175.1–182.1, 217; 173/1–11, 173/176–183; 606/1, 128, 139; 128/898; 318/362
  See application file for complete search history.

(56) References Cited

U.S. PATENT DOCUMENTS

| | | | |
|---|---|---|---|
| 2,744,176 A * | 5/1956 | Kaman | H01H 9/06 173/171 |
| 2,770,694 A | 11/1956 | Jean | |
| 2,770,964 A | 11/1956 | Mercier | |
| 4,255,698 A | 3/1981 | Simon | |
| 4,278,091 A | 7/1981 | Borzone | |
| 4,475,679 A | 10/1984 | Fleury | |
| 4,483,562 A | 11/1984 | Schoolman | |
| 4,488,523 A | 12/1984 | Shichman | |
| 4,558,263 A * | 12/1985 | Harris | B60L 7/22 180/211 |
| 4,564,730 A | 1/1986 | Tomizu | |
| 4,566,620 A | 1/1986 | Green et al. | |
| 4,608,981 A | 9/1986 | Rothfuss et al. | |
| 4,639,646 A * | 1/1987 | Harris | B60L 11/1805 318/139 |
| 4,701,578 A * | 10/1987 | Keranen | H01H 13/72 200/5 B |
| 4,703,140 A | 10/1987 | Poling | |
| 4,795,863 A | 1/1989 | Tomizu et al. | |
| 4,825,134 A * | 4/1989 | Tracht | B60S 1/0807 318/443 |
| 4,857,818 A | 8/1989 | Hobbs | |
| 4,873,977 A | 10/1989 | Avant et al. | |
| 4,897,882 A * | 1/1990 | Pickering | B60L 3/00 318/139 |
| 4,944,443 A | 7/1990 | Oddsen | |
| 4,950,273 A | 8/1990 | Briggs | |
| 4,964,558 A * | 10/1990 | Crutcher | B25C 1/06 173/124 |
| 4,979,497 A | 12/1990 | Matsuura | |
| 5,020,933 A | 6/1991 | Salvestro | |
| 5,020,993 A | 6/1991 | Levandoski et al. | |
| 5,100,418 A | 3/1992 | Yoon et al. | |
| 5,104,025 A | 4/1992 | Main et al. | |
| 5,136,220 A * | 8/1992 | Philipp | H02P 6/24 318/362 |
| 5,139,513 A | 8/1992 | Segato | |
| 5,188,188 A * | 2/1993 | Mars | B23D 49/162 173/147 |
| 5,197,649 A | 3/1993 | Bessler et al. | |
| 5,219,111 A | 6/1993 | Bilotti | |
| 5,255,698 A | 10/1993 | Riley | |
| 5,268,622 A | 12/1993 | Philipp | |
| 5,271,543 A | 12/1993 | Grant et al. | |
| 5,271,544 A | 12/1993 | Fox et al. | |
| 5,292,053 A | 3/1994 | Bilotti et al. | |
| 5,304,184 A | 4/1994 | Hathaway et al. | |
| 5,333,773 A * | 8/1994 | Main | A61B 17/115 227/179.1 |
| 5,348,259 A | 9/1994 | Blanco et al. | |
| 5,350,104 A | 9/1994 | Main | |
| 5,355,897 A | 10/1994 | Pietrafitta et al. | |
| 5,383,874 A | 1/1995 | Jackson et al. | |
| 5,383,880 A | 1/1995 | Hooven | |
| 5,415,666 A | 5/1995 | Gourlay et al. | |
| 5,417,203 A | 5/1995 | Tovey et al. | |
| 5,431,645 A | 7/1995 | Smith | |
| 5,433,721 A * | 7/1995 | Hooven | A61B 17/072 227/175.1 |
| 5,439,156 A | 8/1995 | Grant et al. | |
| 5,465,895 A | 11/1995 | Knodel et al. | |
| 5,467,911 A | 11/1995 | Tsuruta et al. | |
| 5,497,934 A | 3/1996 | Brady | |
| 5,505,593 A | 4/1996 | Hartley et al. | |
| 5,507,426 A | 4/1996 | Young et al. | |
| 5,510,077 A | 4/1996 | Dinh et al. | |
| 5,533,661 A | 7/1996 | Main et al. | |
| 5,575,799 A | 11/1996 | Bolanos | |
| 5,609,285 A | 3/1997 | Grant et al. | |
| 5,626,595 A | 5/1997 | Sklar | |
| 5,632,432 A | 5/1997 | Schulze | |
| 5,645,209 A | 7/1997 | Green et al. | |
| 5,653,374 A | 8/1997 | Young | |
| 5,673,840 A | 10/1997 | Schulze et al. | |
| 5,673,841 A | 10/1997 | Schulze et al. | |
| 5,680,981 A | 10/1997 | Mililli et al. | |
| 5,732,871 A | 3/1998 | Clark et al. | |
| 5,742,718 A | 4/1998 | Harman et al. | |
| 5,743,456 A | 4/1998 | Jones et al. | |
| 5,746,753 A | 5/1998 | Sullivan et al. | |
| 5,759,151 A | 6/1998 | Sturges | |
| 5,762,255 A | 6/1998 | Chrisman et al. | |
| 5,769,820 A | 6/1998 | Rammler | |

(56) References Cited

U.S. PATENT DOCUMENTS

| | | | |
|---|---|---|---|
| 5,779,130 A | 7/1998 | Alesi et al. | |
| 5,779,623 A | 7/1998 | Bonnell et al. | |
| 5,782,396 A | 7/1998 | Mastri et al. | |
| 5,782,397 A | 7/1998 | Koukline | |
| 5,792,165 A | 8/1998 | Klieman et al. | |
| 5,796,188 A | 8/1998 | Bays | |
| 5,797,537 A | 8/1998 | Oberlin et al. | |
| 5,807,261 A | 9/1998 | Benaron et al. | |
| 5,810,811 A | 9/1998 | Yates et al. | |
| 5,817,119 A | 10/1998 | Klieman | |
| 5,862,972 A | 1/1999 | Green et al. | |
| 5,871,863 A | 2/1999 | Miyasaka | |
| 5,901,895 A | 5/1999 | Heaton et al. | |
| 5,915,616 A | 6/1999 | Viola et al. | |
| 5,954,259 A * | 9/1999 | Viola | A61B 17/07207 227/176.1 |
| 5,984,864 A | 11/1999 | Fox et al. | |
| 6,013,991 A | 1/2000 | Philipp et al. | |
| 6,076,018 A | 6/2000 | Sturman et al. | |
| 6,084,366 A * | 7/2000 | Koselke | H02P 6/24 318/362 |
| 6,114,942 A | 9/2000 | Kitamoto et al. | |
| 6,118,234 A * | 9/2000 | Marcellus | H01H 23/164 200/553 |
| 6,120,462 A | 9/2000 | Hibner et al. | |
| 6,127,811 A | 10/2000 | Shenoy et al. | |
| 6,165,173 A | 12/2000 | Kamdar | |
| 6,177,209 B1 | 1/2001 | Okutoh | |
| 6,193,129 B1 | 2/2001 | Bittner et al. | |
| 6,228,287 B1 | 5/2001 | Wong | |
| 6,250,532 B1 | 6/2001 | Green et al. | |
| 6,264,086 B1 | 7/2001 | McGuckin, Jr. | |
| 6,264,087 B1 * | 7/2001 | Whitman | A61B 17/07207 227/176.1 |
| 6,296,634 B1 | 10/2001 | McMillen et al. | |
| 6,315,184 B1 | 11/2001 | Whitman | |
| 6,330,965 B1 | 12/2001 | Milliman et al. | |
| 6,338,737 B1 | 1/2002 | Toledano | |
| 6,340,878 B1 | 1/2002 | Oglesbee | |
| 6,434,507 B1 | 8/2002 | Clayton et al. | |
| 6,443,973 B1 * | 9/2002 | Whitman | A61B 17/07207 227/176.1 |
| 6,491,201 B1 | 12/2002 | Whitman | |
| 6,517,565 B1 | 2/2003 | Whitman | |
| 6,518,528 B2 | 2/2003 | Nickerson et al. | |
| 6,533,157 B1 | 3/2003 | Whitman | |
| 6,585,664 B2 * | 7/2003 | Burdorff | A61B 10/0275 600/564 |
| 6,644,532 B2 | 11/2003 | Green et al. | |
| 6,645,663 B2 | 11/2003 | Bean et al. | |
| 6,666,875 B1 | 12/2003 | Sakurai et al. | |
| 6,676,600 B1 | 1/2004 | Conero | |
| 6,698,643 B2 | 3/2004 | Whitman | |
| 6,716,233 B1 * | 4/2004 | Whitman | A61B 17/07207 606/219 |
| 6,767,153 B1 | 7/2004 | Holbrook | |
| 6,793,652 B1 | 9/2004 | Whitman et al. | |
| 6,830,174 B2 | 12/2004 | Hillstead | |
| 6,846,308 B2 * | 1/2005 | Whitman | A61B 10/0233 600/117 |
| 6,872,226 B2 | 3/2005 | Cali | |
| 6,887,244 B1 | 5/2005 | Walker et al. | |
| 6,905,057 B2 | 6/2005 | Swayze | |
| 6,935,985 B2 | 8/2005 | Ishimaru | |
| 6,945,444 B2 | 9/2005 | Gresham et al. | |
| 6,964,363 B2 | 11/2005 | Wales et al. | |
| 6,981,628 B2 | 1/2006 | Wales | |
| 6,981,941 B2 | 1/2006 | Whitman et al. | |
| 7,023,159 B2 | 4/2006 | Gorti | |
| 7,032,798 B2 | 4/2006 | Whitman | |
| 7,055,731 B2 | 6/2006 | Shelton et al. | |
| 7,059,508 B2 | 6/2006 | Shelton, IV et al. | |
| 7,097,650 B2 | 8/2006 | Weller et al. | |
| 7,111,769 B2 | 9/2006 | Wales et al. | |
| 7,147,138 B2 | 12/2006 | Shelton, IV | |
| 7,168,604 B2 | 1/2007 | Milliman et al. | |
| 7,210,609 B2 | 5/2007 | Leiboff et al. | |
| 7,213,736 B2 | 5/2007 | Wales et al. | |
| 7,246,734 B2 | 7/2007 | Shelton, IV | |
| 7,328,828 B2 | 2/2008 | Ortiz et al. | |
| 7,404,508 B2 | 7/2008 | Smith et al. | |
| 7,419,080 B2 | 9/2008 | Smith et al. | |
| 7,479,608 B2 | 1/2009 | Smith | |
| 7,506,791 B2 | 3/2009 | Omaits et al. | |
| 7,549,563 B2 | 6/2009 | Mather et al. | |
| 7,714,239 B2 | 5/2010 | Smith | |
| 7,922,063 B2 | 4/2011 | Zemlok et al. | |
| 8,028,885 B2 | 10/2011 | Smith et al. | |
| 8,034,077 B2 | 10/2011 | Smith et al. | |
| 8,038,046 B2 | 10/2011 | Smith | |
| 8,245,898 B2 | 8/2012 | Smith et al. | |
| 8,269,121 B2 | 9/2012 | Smith | |
| 8,573,459 B2 | 11/2013 | Smith | |
| 8,579,176 B2 | 11/2013 | Smith et al. | |
| 8,592,700 B2 | 11/2013 | Smith | |
| 8,627,993 B2 | 1/2014 | Smith | |
| 8,627,995 B2 | 1/2014 | Smith et al. | |
| 8,695,865 B2 | 4/2014 | Smith et al. | |
| 8,920,435 B2 | 12/2014 | Smith et al. | |
| 2001/0025136 A1 | 9/2001 | Leonard et al. | |
| 2001/0031975 A1 | 10/2001 | Whitman | |
| 2001/0052416 A1 | 12/2001 | Wissmach et al. | |
| 2002/0077645 A1 | 6/2002 | Wiener et al. | |
| 2002/0161385 A1 | 10/2002 | Wiener et al. | |
| 2003/0092364 A1 | 5/2003 | Erickson | |
| 2003/0105478 A1 | 6/2003 | Whitman et al. | |
| 2003/0130676 A1 | 7/2003 | Sugimura | |
| 2003/0195538 A1 | 10/2003 | Wang | |
| 2004/0003683 A1 | 1/2004 | Rudduck | |
| 2004/0034280 A1 | 2/2004 | Privitera et al. | |
| 2004/0049217 A1 | 3/2004 | Ross | |
| 2004/0059338 A1 | 3/2004 | Ebner | |
| 2004/0093057 A1 | 5/2004 | Bolduc | |
| 2004/0122419 A1 | 6/2004 | Neuberger | |
| 2004/0129551 A1 | 7/2004 | Kent et al. | |
| 2004/0210282 A1 | 10/2004 | Flock | |
| 2004/0220602 A1 | 11/2004 | Deng | |
| 2004/0249366 A1 | 12/2004 | Kunz | |
| 2004/0267297 A1 | 12/2004 | Malackowski | |
| 2005/0052145 A1 | 3/2005 | Carrier | |
| 2005/0090837 A1 | 4/2005 | Sixto, Jr. et al. | |
| 2005/0127131 A1 | 6/2005 | Mastri et al. | |
| 2005/0131390 A1 * | 6/2005 | Heinrich | A61B 17/0469 606/1 |
| 2005/0131428 A1 | 6/2005 | Bombard et al. | |
| 2005/0149003 A1 | 7/2005 | Tierney et al. | |
| 2005/0159752 A1 | 7/2005 | Walker | |
| 2005/0173490 A1 | 8/2005 | Shelton | |
| 2005/0222616 A1 | 10/2005 | Rethy et al. | |
| 2005/0234435 A1 * | 10/2005 | Layer | A61B 17/3403 606/1 |
| 2005/0234442 A1 * | 10/2005 | Spears | A61B 18/1402 606/39 |
| 2005/0252756 A1 | 11/2005 | Kent et al. | |
| 2005/0268750 A1 * | 12/2005 | Bruce | A61B 17/866 81/52 |
| 2006/0011361 A1 * | 1/2006 | Shimma | B25D 16/006 173/48 |
| 2006/0047308 A1 | 3/2006 | Ortiz et al. | |
| 2006/0060630 A1 | 3/2006 | Shelton, IV et al. | |
| 2006/0087283 A1 | 4/2006 | Phillips et al. | |
| 2006/0092674 A1 | 5/2006 | Belton | |
| 2006/0095096 A1 | 5/2006 | DeBenedictis | |
| 2006/0129140 A1 | 6/2006 | Todd et al. | |
| 2006/0212069 A1 | 9/2006 | Shelton, IV | |
| 2006/0241655 A1 | 10/2006 | Viola | |
| 2006/0264742 A1 | 11/2006 | Neubauer et al. | |
| 2006/0278680 A1 | 12/2006 | Viola | |
| 2006/0278681 A1 | 12/2006 | Viola et al. | |
| 2006/0282084 A1 | 12/2006 | Blier et al. | |
| 2007/0027469 A1 | 2/2007 | Smith et al. | |
| 2007/0039996 A1 | 2/2007 | Mather et al. | |
| 2007/0073341 A1 | 3/2007 | Smith et al. | |

(56) References Cited

U.S. PATENT DOCUMENTS

| | | |
|---|---|---|
| 2007/0083233 A1 | 4/2007 | Ortiz |
| 2007/0175952 A1 | 8/2007 | Shelton et al. |
| 2007/0175956 A1 | 8/2007 | Swayze et al. |
| 2007/0175964 A1 | 8/2007 | Shelton et al. |
| 2007/0179408 A1 | 8/2007 | Soltz |
| 2007/0187453 A1 | 8/2007 | Smith et al. |
| 2007/0213692 A1 | 9/2007 | Neubauer et al. |
| 2007/0221701 A1 | 9/2007 | Ortiz et al. |
| 2008/0167672 A1 | 7/2008 | Giordano et al. |
| 2008/0262654 A1 | 10/2008 | Omori et al. |
| 2008/0263855 A1 | 10/2008 | Li |
| 2010/0270355 A1 | 10/2010 | Whitman |

FOREIGN PATENT DOCUMENTS

| | | |
|---|---|---|
| CA | 2609970 A1 | 12/2006 |
| CN | 87207549 | 5/1988 |
| CN | 1417004 | 5/2003 |
| CN | 1730245 | 2/2006 |
| EP | 0 134 560 | 3/1985 |
| EP | 0 216 532 | 4/1987 |
| EP | 0 438 827 | 7/1991 |
| EP | 0541987 A1 | 5/1993 |
| EP | 0 552 050 | 7/1993 |
| EP | 0552050 A2 | 7/1993 |
| EP | 0567146 A2 | 10/1993 |
| EP | 0592243 A2 | 4/1994 |
| EP | 0625335 A1 | 11/1994 |
| EP | 0 634 144 | 1/1995 |
| EP | 0 674 876 | 3/1995 |
| EP | 0 705 57 | 4/1996 |
| EP | 0 705 570 | 4/1996 |
| EP | 0 705 571 A1 | 4/1996 |
| EP | 0 717 960 | 6/1996 |
| EP | 1040790 A2 | 10/2000 |
| EP | 1 201 195 | 5/2002 |
| EP | 1 201 196 | 5/2002 |
| EP | 1201196 A1 | 5/2002 |
| EP | 1411626 A2 | 4/2004 |
| EP | 1479348 A1 | 11/2004 |
| EP | 1496805 A2 | 1/2005 |
| EP | 1 728 475 | 12/2006 |
| EP | 1 997 439 | 12/2008 |
| EP | 1 359 851 | 9/2010 |
| JP | S4934609 | 3/1974 |
| JP | S57-168147 U | 4/1981 |
| JP | S60-035431 | 3/1985 |
| JP | S58127136 | 3/1985 |
| JP | S62-032444 | 2/1987 |
| JP | S60122464 | 2/1987 |
| JP | S62-166814 U | 10/1987 |
| JP | S62-229617 A | 10/1987 |
| JP | H01-159337 | 11/1989 |
| JP | 03-273708 | 12/1991 |
| JP | 03-286755 | 12/1991 |
| JP | 06-304174 | 11/1994 |
| JP | H7-217762 | 8/1995 |
| JP | 08-182684 | 7/1996 |
| JP | 08-336540 A | 12/1996 |
| JP | H09-289991 | 11/1997 |
| JP | 10-507384 | 7/1998 |
| JP | 11-192225 | 7/1999 |
| JP | 2001-190563 | 7/2001 |
| JP | 2001-272485 | 10/2001 |
| JP | 2002-503975 A | 2/2002 |
| JP | H3273108 | 4/2002 |
| JP | 2003-175056 | 6/2003 |
| JP | 2003175056 A | 6/2003 |
| JP | 2003-523255 | 8/2003 |
| JP | 2003525650 A | 9/2003 |
| JP | 2004514490 A | 5/2004 |
| JP | 2004260980 A | 9/2004 |
| JP | 2004274928 A | 9/2004 |
| JP | 2005-502441 | 1/2005 |
| JP | 2005094128 A | 4/2005 |
| JP | 2005-118606 | 5/2005 |
| JP | 2005243652 A | 9/2005 |
| JP | 2006-218297 | 8/2006 |
| WO | 83/03341 | 10/1983 |
| WO | 94/14129 | 6/1994 |
| WO | 95/18572 | 7/1995 |
| WO | 97/29678 | 8/1997 |
| WO | 99/66850 | 12/1999 |
| WO | 01/12090 | 2/2001 |
| WO | 0162163 A1 | 8/2001 |
| WO | 02/28290 | 4/2002 |
| WO | 02/39909 | 5/2002 |
| WO | 02/085194 | 10/2002 |
| WO | 03/05698 | 1/2003 |
| WO | 03/077769 | 9/2003 |
| WO | 03/090630 | 11/2003 |
| WO | 2004021909 A1 | 3/2004 |
| WO | 20040019710 | 3/2004 |
| WO | 2004/032596 | 4/2004 |
| WO | 2004/032760 A2 | 4/2004 |
| WO | 2004112618 | 12/2004 |
| WO | 2005/037084 | 4/2005 |
| WO | 2005078892 A1 | 8/2005 |
| WO | 2006/012752 | 2/2006 |
| WO | 2006/031632 | 3/2006 |
| WO | 2007142625 A2 | 12/2007 |

OTHER PUBLICATIONS

Supplementary European Search Report for EP 08730353 dated Dec. 10, 2015.
Office Action for Chinese Patent Application No. 201410133489.X dated Jul. 23, 2015.
Office Action of European Patent App. No. 10 004 893.3 dated Aug. 4, 2015.
European Search Report of European App. No. 10 00 7212 dated Nov. 30, 2012.
European Search Report of European App. No. 12 00 3870 dated Dec. 4, 2012.
European Search Report of European App. No. 12 00 3924 dated Dec. 4, 2012.
European Search Report of European App. No. 12 00 3925 dated Jul. 28, 2015.
Office Action for Japanese Patent App. No. 2010-204593 dated Jul. 17, 2012.
Office Action for Japanese Patent App. No. 2013-229885 dated Mar. 13, 2015.
Office Action for Chinese Patent App. No. 200880012925.0 dated Jul. 2011.
Office Action for Australian Patent App. No. 2012203402 dated Dec. 10, 2010.
Office Action for Japanese Patent App. No. 2009-551007 dated Mar. 16, 2012.
Office Action for Japanese Patent App. No. 2009-551007 dated Oct. 25, 2011.
Office Action for Japanese Patent App. No. 2014-08518 dated Apr. 27, 2015.
Office Action for Australian Patent App. No. 2012203920 dated Jan. 31, 2014.
European Search Report of European Patent App. No. 08 83 4819 dated Dec. 1, 2011.
Office Action for Japanese Patent App. No. 2010-528199 dated Mar. 5, 2013.
Office Action for Japanese Patent App. No. 2014-008906 dated Jan. 13, 2015.
Office Action for Australian Patent App. No. 2010257314 dated May 21, 2012.
Office Action for Australian Patent App. No. 2010257434 dated May 3, 2012.
Office Action for Australian Patent App. No. 2010257442 dated Apr. 5, 2011.
Office Action for Australian Patent App. No. 2014202303 dated May 22, 2014.

(56) References Cited

OTHER PUBLICATIONS

Office Action for Chinese Patent App. No. 200720017794.0 dated Dec. 7, 2012.
Office Action for Chinese Patent App. No. 200880110386.4 dated Apr. 1, 2013.
European Search Report of European App. No. 07 78 4247 dated Oct. 21, 2009.
Office Action for European Patent App. No. 11 007 4838 dated Aug. 9, 2013.
Office Action for European Patent App. No. 11 007 6551 dated Aug. 13, 2013.
Office Action for European Patent App. No. 12 00 1644 dated Oct. 31, 2013.
European Search Report of European App. No. 14 19 0268 dated Jan. 27, 2015.
European Search Report of European App. No. 14 19 0271 dated Feb. 4, 2015.
Office Action for Japanese Patent App. No. 2009-511264 dated Feb. 10, 2010.
Office Action for Japanese Patent App. No. 2011-005788 dated Oct. 2, 2012.
Office Action for Japanese Patent App. No. 2013-176415 dated Sep. 9, 2014.
International Search Report of PCT/US08/54530 dated Nov. 7, 2008.
International Search Report of PCT/US07/69334 dated Feb. 13, 2008.
International Search Report of PCT/US07/70085 dated Aug. 4, 2008.
International Search Report of PCT/US08/50829 dated Aug. 1, 2008.
International Search Report of PCT/US08/78876 dated Dec. 5, 2008.
European Search Report of EP App. No. 11 00 7409 dated Dec. 12, 2012.
European Search Report of EP App. No. 11 00 7483 dated Nov. 21, 2012.
European Search Report of EP App. No. 11 00 7655 dated Nov. 29, 2012.
European Search Report of EP App. No. 12 00 1644 dated Jan. 7, 2013.
European Search Report of EP App. No. 12 00 1655 dated dated Dec. 7, 2012.
European Search Report of EP App. No. 11 00 7731 dated Dec. 3, 2012.
Communication Pursuant to Article 94(3) for European Patent App. No. 12 001 655.5 dated Jan. 14, 2014.
Office Action for Chinese Patent App. No. 201110152302.7 dated Dec. 26, 2013.
European Search Report of EP App. No. 12 00 1645 dated Jan. 31, 2013.
European Search Report of EP App. No. 12 00 1576 dated Jan. 18, 2013.
European Search Report of EP App. No. 12 00 1653 dated Jan. 31, 2013.
European Search Report of EP App. No. 11 00 7576 dated Feb. 20, 2013.
European Search Report of EP App. No. 12 00 1656 dated Feb. 18, 2013.
European Search Report of EP App. No. 12 00 1654 dated Feb. 13, 2013.
European Search Report of EP App. No. 12 00 1588 dated Jan. 24, 2013.
European Search Report of European Patent App. No. 12003926 dated Sep. 10, 2015.
European Search Report of European Patent App. No. 15168712 dated Sep. 25, 2015.
European Search Report of European Patent App. No. 12003957 dated Sep. 22, 2015.
European Search Report of European Patent App. No. 15 17 2665 dated Oct. 13, 2015.
Summons to Attend Oral Hearing of European Patent App. No. 12 001 644.9 dated Oct. 7, 2015.
Summons to Attend Oral Hearing of European Patent App. No. 12 001 654.8 dated Oct. 19, 2015.
European Search Report of European Patent App. No. 12003959 dated Jan. 8, 2016.
European Search Report for the application No. EP 16153184 dated May 10, 2016.
Examination Report Issued from App. No. 2014250664 dated May 13, 2016.
Notice of Rejection in Japanese Patent App. No. 2015-220874, dated Sep. 13, 2016.
Official Communication on European Patent No. 14190268.4 dated Sep. 27, 2016.
Examination Report Issued on AU. App. No. 2013211550 dated Jan. 8, 2016.
Office Action for Japanese Patent App. No. 2016-051247 dated Feb. 28, 2017.
Office Action for Japanese Patent App. No. 2017-019295 dated May 16, 2017.
First Examination Report from India Application No. 4316/DELNP/2010 dated Jun. 30, 2017.
European Search Report of European App. No. EP17154834 dated May 11, 2017.
Notice of Rejection in Japanese Patent App. No. 2015-220874 dated Jul. 4, 2017.
Official Action for Brazilian Application No. PI-0614175-7 dated Jun. 5, 2017.
JP 03-273708, ITO, machine translation with drawing, Apr. 1991.
JP 62-032444 (equivalent to JP 60-122465), Kobayashi, machine translation Feb. 1987.
European Search Report of European Patent App. No. 17178415.0 dated Sep. 28, 2017.
European Search Report of European Patent App. No. 17179644.4 dated Oct. 12, 2017.

* cited by examiner

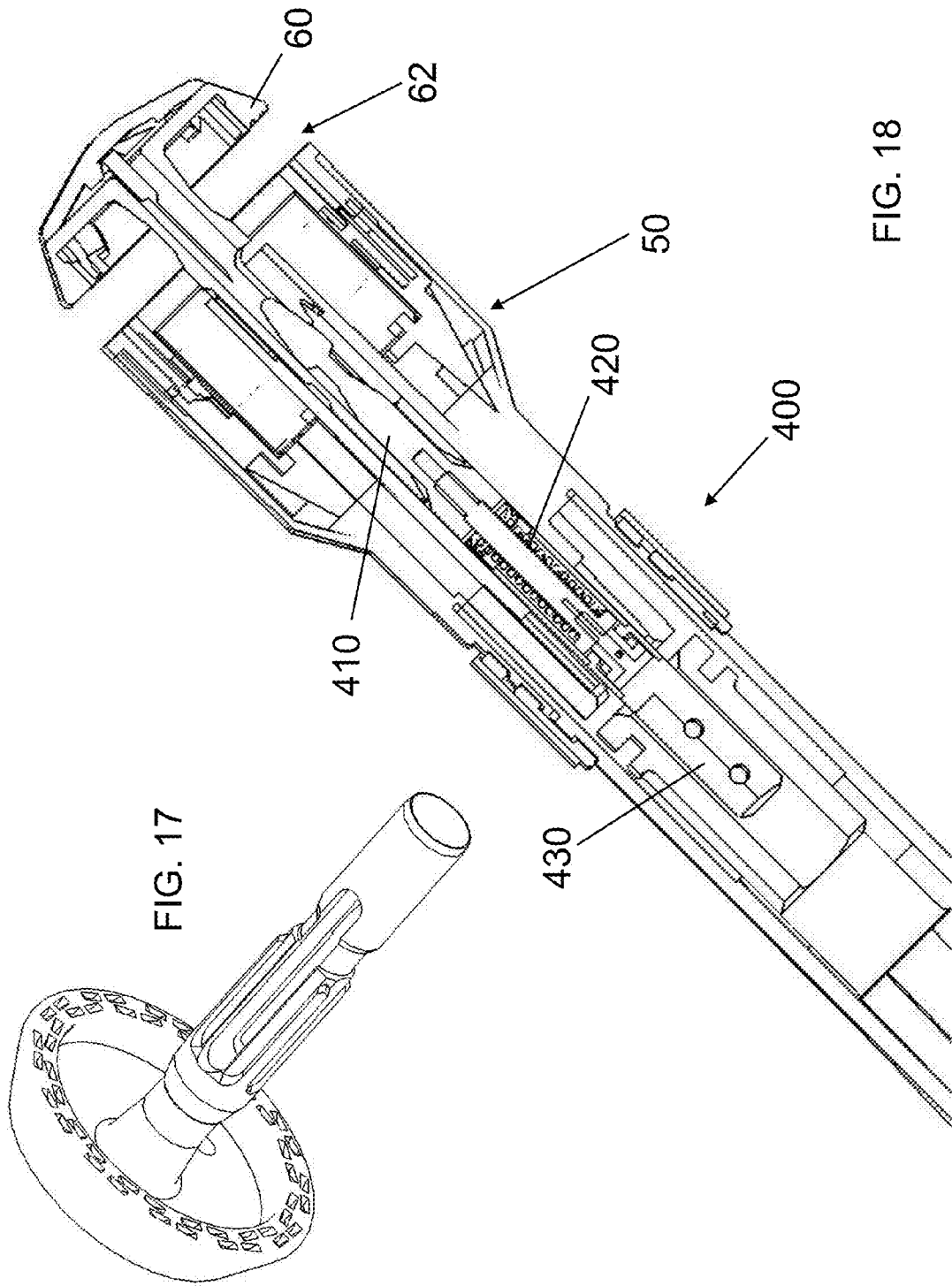

ACTIVE BRAKING ELECTRICAL SURGICAL INSTRUMENT AND METHOD FOR BRAKING SUCH AN INSTRUMENT

CROSS-REFERENCE TO RELATED APPLICATIONS

This application is:

a divisional of U.S. patent application Ser. No. 11/705,381, now U.S. Pat. No. 8,038,046, filed on Feb. 12, 2007 (which application claims the priority, under 35 U.S.C. §119, of U.S. Provisional Patent Application Ser. Nos. 60/801,989, filed on May 19, 2006, 60/810,272, filed on Jun. 2, 2006, and 60/858,112, filed on Nov. 9, 2006);

a divisional of U.S. patent application Ser. No. 11/705,246, now U.S. Pat. No. 8,028,885, filed on Feb. 12, 2007 (which application claims the priority, under 35 U.S.C. §119, of U.S. Provisional Patent Application Ser. Nos. 60/801,989, filed on May 19, 2006, 60/810,272, filed on Jun. 2, 2006, and 60/858,112, filed on Nov. 9, 2006);

a divisional of U.S. patent application Ser. No. 11/705,334, filed on Feb. 12, 2007 (which application claims the priority, under 35 U.S.C. §119, of U.S. Provisional Patent Application Ser. Nos. 60/801,989, filed on May 19, 2006, 60/810,272, filed on Jun. 2, 2006, and 60/858,112, filed on Nov. 9, 2006);

is a continuation-in-part of U.S. patent application Ser. No. 11/750,622, filed May 18, 2007, now U.S. Pat. No. 7,479,608 (which claims the priority, under 35 U.S.C. §119, of U.S. Provisional Patent Application Ser. No. 60/801,989, filed on May 19, 2006);

a divisional of U.S. patent application Ser. Nos. 12/102,464 and 12/102,181, filed on Apr. 14, 2008, (which applications claim priority, under 35 U.S.C. §119, of U.S. Provisional Patent Application Ser. No. 60/997,489, filed Oct. 4, 2007);

is a continuation-in-part of U.S. patent application Ser. No. 12/270,518, filed Nov. 13, 2008, now U.S. Pat. No. 7,714,239;

a divisional of U.S. patent application Ser. No. 12/612,525 filed on Nov. 4, 2009;

is a continuation-in-part of U.S. patent application Ser. No. 12/728,471, filed Mar. 22, 2010;

a divisional of U.S. patent application Ser. No. 12/793,962, filed on Jun. 4, 2010;

a divisional of U.S. patent application Ser. No. 13/229,076, filed on Sep. 9, 2011;

is a continuation-in-part of U.S. patent application Ser. No. 13/571,159, filed Aug. 9, 2012;

a divisional of U.S. patent application Ser. No. 13/611,881, filed on Sep. 12, 2012; and a divisional of U.S. patent application Ser. No. 13/622,819, filed on Sep. 19, 2012, the entire disclosures of these applications are all hereby incorporated herein by reference in their entireties.

COMPUTER PROGRAM LISTING APPENDIX

A computer program listing appendix is included with this application on a single compact disc, the entire contents of which are incorporated herein by reference. The file name, date of creation, and size for the file submitted on the compact disc are:

Elec Stap Active Brake Div 1 Comp Prog Listing f.pdf, Nov. 8, 2017, 80 KB.

FIELD OF THE INVENTION

The present invention lies in the field of surgical instruments, in particular but not necessarily, stapling devices. The stapling device described in the present application is a hand-held, fully electrically powered and controlled surgical stapler.

BACKGROUND OF THE INVENTION

Medical stapling devices exist in the art. Ethicon Endo-Surgery, Inc. (a Johnson & Johnson company; hereinafter "Ethicon") manufactures and sells such stapling devices. Circular stapling devices manufactured by Ethicon are referred to under the trade names PROXIMATE® PPH, CDH and ILS and linear staplers are manufactured by Ethicon under the trade names CONTOUR and PROXIMATE. In each of these exemplary surgical staplers, tissue is compressed between a staple cartridge and an anvil and, when the staples are ejected, the compressed tissue is also cut. Depending upon the particular tissue engaged by the physician, the tissue can be compressed too little (where blood color is still visibly present in the tissue), too much (where tissue is crushed), or correctly (where the liquid is removed from the tissue, referred to as dessicating or blanching.)

Staples to be delivered have a given length and the cartridge and anvil need to be within an acceptable staple firing distance so that the staples close properly upon firing. Therefore, these staplers have devices indicating the relative distance between the two planes and whether or not this distance is within the staple length firing range. Such an indicator is mechanical and takes the form of a sliding bar behind a window having indicated thereon a safe staple-firing range. These staplers are all hand-powered, in other words, they require physical actuations by the user/physician to position the anvil and stapler cartridge about the tissue to be stapled and/or cut, to close the anvil and stapler cartridge with respect to one another, and to fire and secure the staples at the tissue (and/or cut the tissue). No prior art staplers are electrically powered to carry out each of these operations because the longitudinal force necessary to effect staple firing is typically on the order of 250 pounds at the staple cartridge. Further, such staplers do not have any kind of active compression indicator that would optimizes the force acting upon the tissue that is to be stapled so that tissue degradation does not occur.

One hand-powered, intraluminal anastomotic circular stapler is depicted, for example, in U.S. Pat. No. 5,104,025 to Main et al., and assigned to Ethicon. Main et al. is hereby incorporated herein by reference in its entirety. As can be seen most clearly in the exploded view of FIG. 7 in Main et al., a trocar shaft 22 has a distal indentation 21, some recesses 28 for aligning the trocar shaft 22 to serrations 29 in the anvil and, thereby, align the staples with the anvils 34. A trocar tip 26 is capable of puncturing through tissue when pressure is applied thereto. FIGS. 3 to 6 in Main et al. show how the circular stapler 10 functions to join two pieces of tissue together. As the anvil 30 is moved closer to the head 20, interposed tissue is compressed therebetween, as particularly shown in FIGS. 5 and 6. If this tissue is overcompressed, the surgical stapling procedure might not succeed. Thus, it is desirable to not exceed the maximum acceptable tissue compression force. The interposed tissue can be subject to a range of acceptable compressing force during surgery. This range is known and referred to as optimal tissue compression or OTC, and is dependent upon the type of tissue being stapled. While the stapler shown in Main et al. does have a bar indicator that displays to the user a safe staple-firing distance between the anvil and the staple cartridge, it cannot indicate to the user any level of compressive force being imparted upon the tissue prior to stapling. It would be desirable to provide such an indication so that over-compression of the tissue can be avoided.

SUMMARY OF THE INVENTION

The invention overcomes the above-noted and other deficiencies of the prior art by providing an electric surgical stapling device that is electrically powered to position the anvil and stapler cartridge with respect to one another about the tissue to be stapled and/or cut, to close the anvil and stapler cartridge with respect to one another, and to fire and secure the staples at the tissue (and/or cut the tissue). Further, the electric surgical stapling device can indicate to the user a user-pre-defined level of compressive force being imparted upon the tissue prior to firing the staples. The present invention also provides methods for operating the electric surgical stapling device to staple when OTC exists.

An offset-axis configuration for the two anvil and staple firing sub-assemblies creates a device that can be sized to comfortably fit into a user's hand. It also decreases manufacturing difficulty by removing previously required nested (co-axial) hollow shafts. With the axis of the anvil sub-assembly being offset from the staple firing sub-assembly, the length of the threaded rod for extending and retracting the anvil can be decreased by approximately two inches, thereby saving in manufacturing cost and generating a shorter longitudinal profile.

An exemplary method for using the electric stapler includes a power-on feature that permits entry into a manual mode for testing purposes. In a surgical procedure, the stapler is a one-way device. In the test mode, however, the user has the ability to move the trocar back and forth as desired. This test mode can be disengaged and the stapler reset to the use mode for packaging and shipment. For packaging, it is desirable (but not necessary) to have the anvil be at a distance from the staple cartridge. Therefore, a homing sequence can be programmed to place the anvil 1 cm (for example) away from the staple cartridge before powering down for packaging and shipment. Before use, the trocar is extended and the anvil is removed. If the stapler is being used to dissect a colon, for example, the trocar is retracted back into the handle and the handle is inserted trans-anally into the colon to downstream side of the dissection while the anvil is inserted through a laparoscopic incision to an upstream side of the dissection. The anvil is attached to the trocar and the two parts are retracted towards the handle until a staple ready condition occurs. The staple firing sequence is started, which can be aborted, to staple the dissection and simultaneously cut tissue at the center of the dissection to clear an opening in the middle of the circular ring of staples. The staple firing sequence includes an optimal tissue compression (OTC) measurement and feedback control mechanism that causes staples to be fired only when the compression is in a desired pressure range, referred to as the OTC range. This range or value is known beforehand based upon known characteristics of the tissue to be compressed between the anvil and staple cartridge.

Some exemplary procedures in which the electric stapler can be used include colon dissection and gastric bypass surgeries. There are many other uses for the electric stapler in various different technology areas.

With the foregoing and other objects in view, there is provided, in accordance with the invention, a surgical instrument, comprising a surgical end effector having at least one actuation assembly to effect a surgical procedure when actuated, a handle mechanically coupled with the end effector and having a shell, an electric motor disposed within the shell and having motor terminals and a drive train operatively coupled to the at least one actuation assembly to actuate the at least one actuation assembly when the motor is supplied with power, a power supply having power terminals, and a selective switching connection disposed within the shell and having a break-before-make switch with three positions including a forward position, a reverse position, and an off position, the selective switching connection in the forward position, electrically connecting the power terminals to the motor terminals to power the motor in a forward direction, in the reverse position, electrically connecting the power terminals to the motor terminals to power the motor in a reverse direction, and in the off position, electrically separating at least one of the power terminals from the motor terminals.

In accordance with another feature of the invention, the power supply is a removable battery pack and has two power terminals, and the switch of the selective switching connection is a double-pole/double-throw, break-before-make switch with three positions including the forward position, the reverse position, and the off position, and in the forward position, electrically connects the two power terminals to the two motor terminals to power the motor in a forward direction, in the reverse position, electrically connects the two power terminals to the two motor terminals to power the motor in a reverse direction, and in the off position, electrically separates at least one of the two power terminals from the two motor terminals.

In accordance with a further feature of the invention, the end effector, handle, motor, and selective switching connection are all operable with only a single hand.

In accordance with an added feature of the invention, the end effector is a surgical stapling endocutter.

In accordance with an additional feature of the invention, the motor has a permanent magnetic field and at least one of the motor, the drive train, and the actuation assembly has an inertia-induced over-stroke characteristic after powered operation.

In accordance with another feature of the invention, there is provided a post-termination braking circuit having the selective switching connection as a component thereof, the post-termination braking circuit electrically short-circuiting the motor terminals with the off position of the switch.

In accordance with an added feature of the invention, the inertia-induced over-stroke of at least one of the motor, the drive train, and the actuation assembly is counteracted with the short-circuit.

In accordance with yet an added feature of the invention, the short-circuit slows the still-spinning motor at a rate that substantially eliminates the inertia-induced over-stroke of at least one of the motor, the drive train, and the actuation assembly.

In accordance with yet another feature of the invention, the drive train has a rotational inertia when operating, and the motor has a rotational inertia when spinning and a permanent magnetic field.

In accordance with another feature of the invention, there is provided a post-termination braking circuit having the selective switching connection as a component thereof, the post-termination braking circuit operable to create an electrically-generated magnetic field in opposition to the permanent magnetic field with the rotational inertia of at least one of the drive train and the motor when short-circuiting the motor terminals with the off position of the switch.

With the objects of the invention in view, there is also provided a surgical instrument, comprising a surgical end effector having at least one actuation assembly to effect a surgical procedure when actuated, a handle mechanically coupled with the end effector and having a shell, an electric motor disposed within the shell and having motor terminals and a drive train operatively coupled to the at least one actuation assembly to actuate the at least one actuation assembly when the motor is supplied with power, a power supply having power terminals, and a post-termination braking circuit having a selective switching connection disposed within the shell and having a break-before-make switch with three positions including a forward position, a reverse position, and an off position, the selective switching connection in the forward position, electrically connecting the power terminals to the motor terminals to power the motor in a forward direction, in the reverse position, electrically connecting the power terminals to the motor terminals to power the motor in a reverse direction, and in the off position, electrically separating at least one of the power terminals from the motor terminals, and electrically short-circuiting the motor terminals with the off position of the switch.

In accordance with another feature of the invention, the power supply is a removable battery pack and has two power terminals and the switch of the selective switching connection is a double-pole/double-throw, break-before-make switch with three positions including the forward position, the reverse position, and the off position, and in the forward position, electrically connects the two power terminals to the two motor terminals to power the motor in a forward direction, in the reverse position, electrically connects the two power terminals to the two motor terminals to power the motor in a reverse direction, and in the off position, electrically separates at least one of the two power terminals from the two motor terminals.

With the objects of the invention in view, there is further provided a surgical instrument, comprising a surgical end effector having at least one actuation assembly to effect a surgical procedure when actuated, a handle mechanically coupled with the end effector and having a shell, an electric motor disposed within the shell and having a rotational inertia when spinning, a permanent magnetic field, motor terminals, and a drive train operatively coupled to the at least one actuation assembly to actuate the at least one actuation assembly when the motor is supplied with power, the drive train having a rotational inertia when operating, a power supply having power terminals, and a post-termination braking circuit having a selective switching connection disposed within the shell and having a break-before-make switch with three positions including a forward position, a reverse position, and an off position, the selective switching connection in the forward position, electrically connecting the power terminals to the motor terminals to power the motor in a forward direction, in the reverse position, electrically connecting the power terminals to the motor terminals to power the motor in a reverse direction, and in the off position, electrically separating at least one of the power terminals from the motor terminals, electrically short-circuiting the motor terminals with the off position of the switch, and being operable to create an electrically-generated magnetic field in opposition to the permanent magnetic field with the rotational inertia of at least one of the drive train and the motor when short-circuiting the motor terminals with the off position of the switch.

Other features that are considered as characteristic for the invention are set forth in the appended claims.

Although the invention is illustrated and described herein as embodied in an active braking electrical surgical instrument and a method for braking such an instrument, it is, nevertheless, not intended to be limited to the details shown because various modifications and structural changes may be made therein without departing from the spirit of the invention and within the scope and range of equivalents of the claims.

The construction and method of operation of the invention, however, together with additional objects and advantages thereof, will be best understood from the following description of specific embodiments when read in connection with the accompanying drawings.

BRIEF DESCRIPTION OF THE DRAWINGS

Advantages of embodiments of the present invention will be apparent from the following detailed description of the preferred embodiments thereof, which description should be considered in conjunction with the accompanying drawings in which:

FIG. 17 is a perspective view of a portion of an anvil of the stapler of FIG. 1;

FIG. 18 is a fragmentary, cross-sectional view of a removable stapling assembly including the anvil, a stapler cartridge, a force switch, and a removable cartridge connecting assembly of the stapler of FIG. 1;

DETAILED DESCRIPTION OF THE INVENTION

Figure 1:
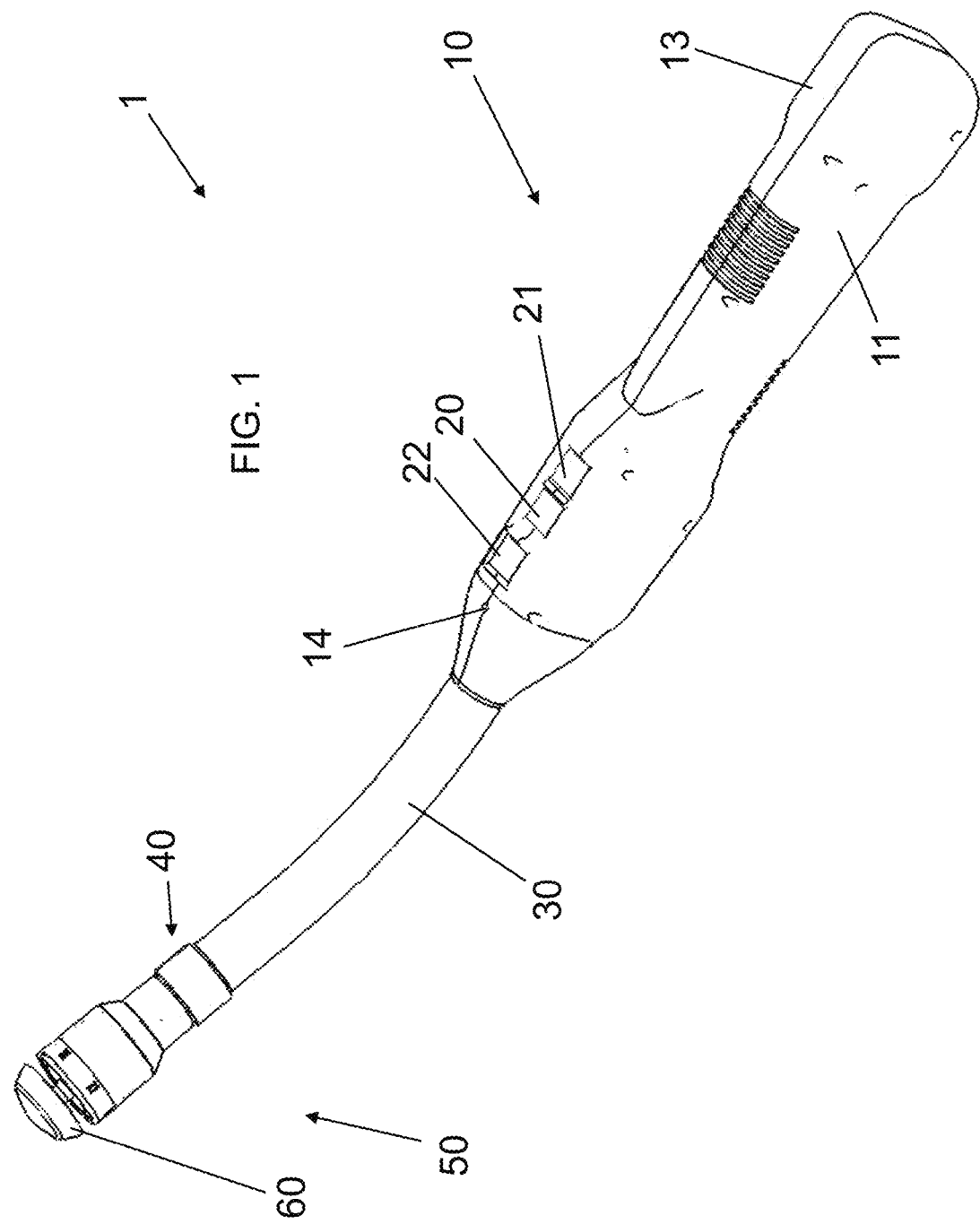
FIG. 1 is a perspective view from a side of an exemplary embodiment of an electric stapler according to the invention.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention.

Before the present invention is disclosed and described, it is to be understood that the terminology used herein is for the purpose of describing particular embodiments only and is not intended to be limiting. It must be noted that, as used in the specification and the appended claims, the singular forms "a," "an," and "the" include plural references unless the context clearly dictates otherwise. The term "another," as used herein, is defined as at least a second or more. The terms "including" and/or "having," as used herein, are defined as comprising (i.e., open language).

While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale. Further, it is noted that the figures have been created using a computer-aided design computer program. This program at times removes certain structural lines and/or surfaces when switching from a shaded or colored view to a wireframe view. Accordingly, the drawings should be treated as approximations and be used as illustrative of the features of the present invention.

Figure 2:
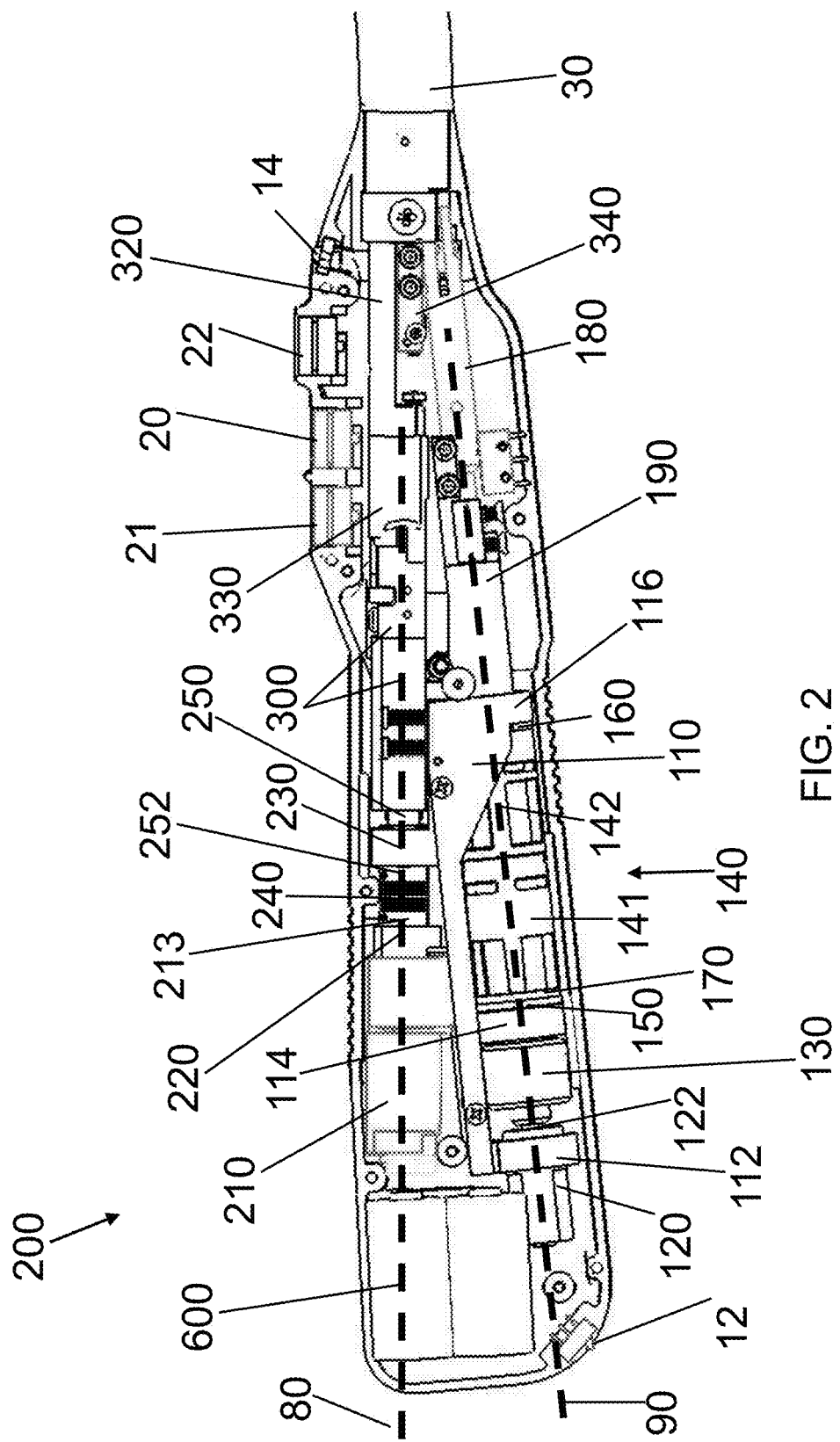
FIG. 2 is a fragmentary side elevational view of the stapler of FIG. 1 with a right half of a handle body and with a proximal backbone plate removed.

Referring now to the figures of the drawings in detail and first, particularly to FIGS. 1 to 2 thereof, there is shown an exemplary embodiment of an electric surgical circular stapler 1. The present application applies the electrically powered handle to a circular surgical staple head for ease of understanding only. The invention is not limited to circular staplers and can be applied to any surgical stapling head, such as a linear stapling device, for example.

Figure 12:
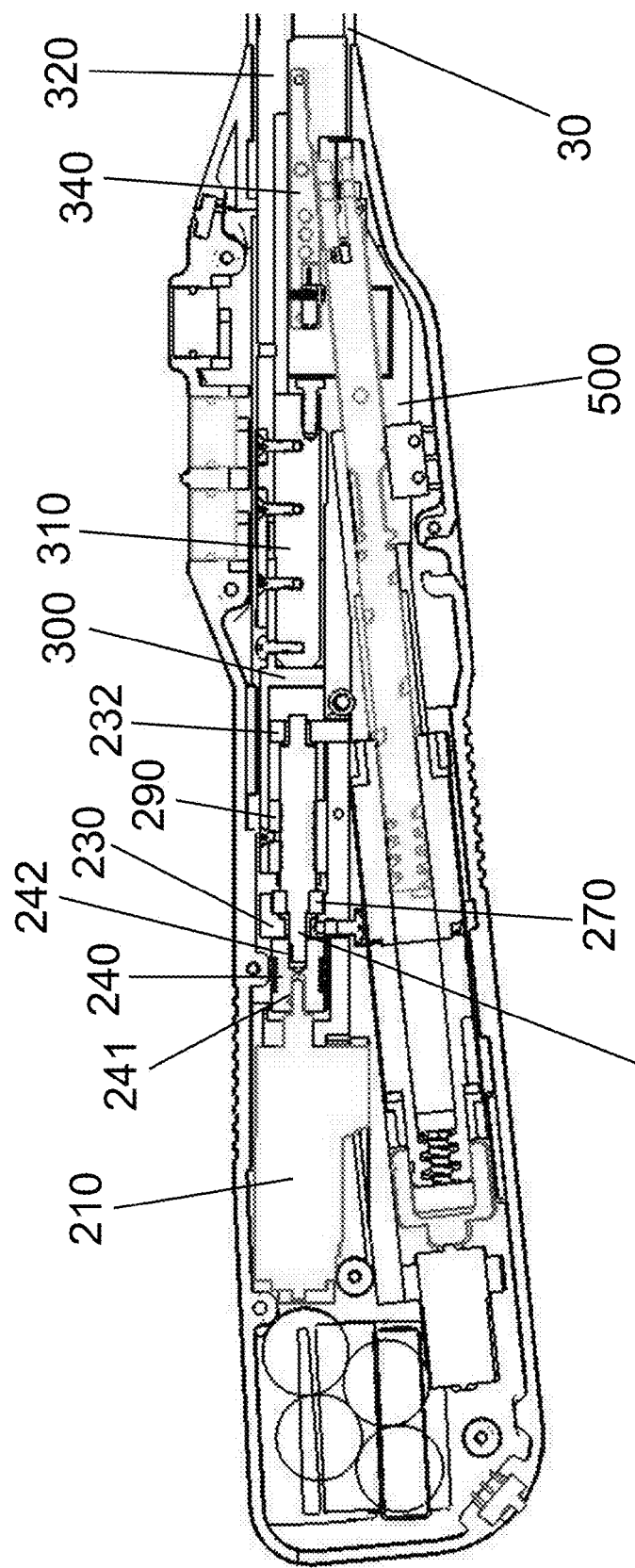
FIG. 12 is a fragmentary, vertically cross-sectional view from a right side of a handle body portion of the stapler of FIG. 1.
Figure 13:
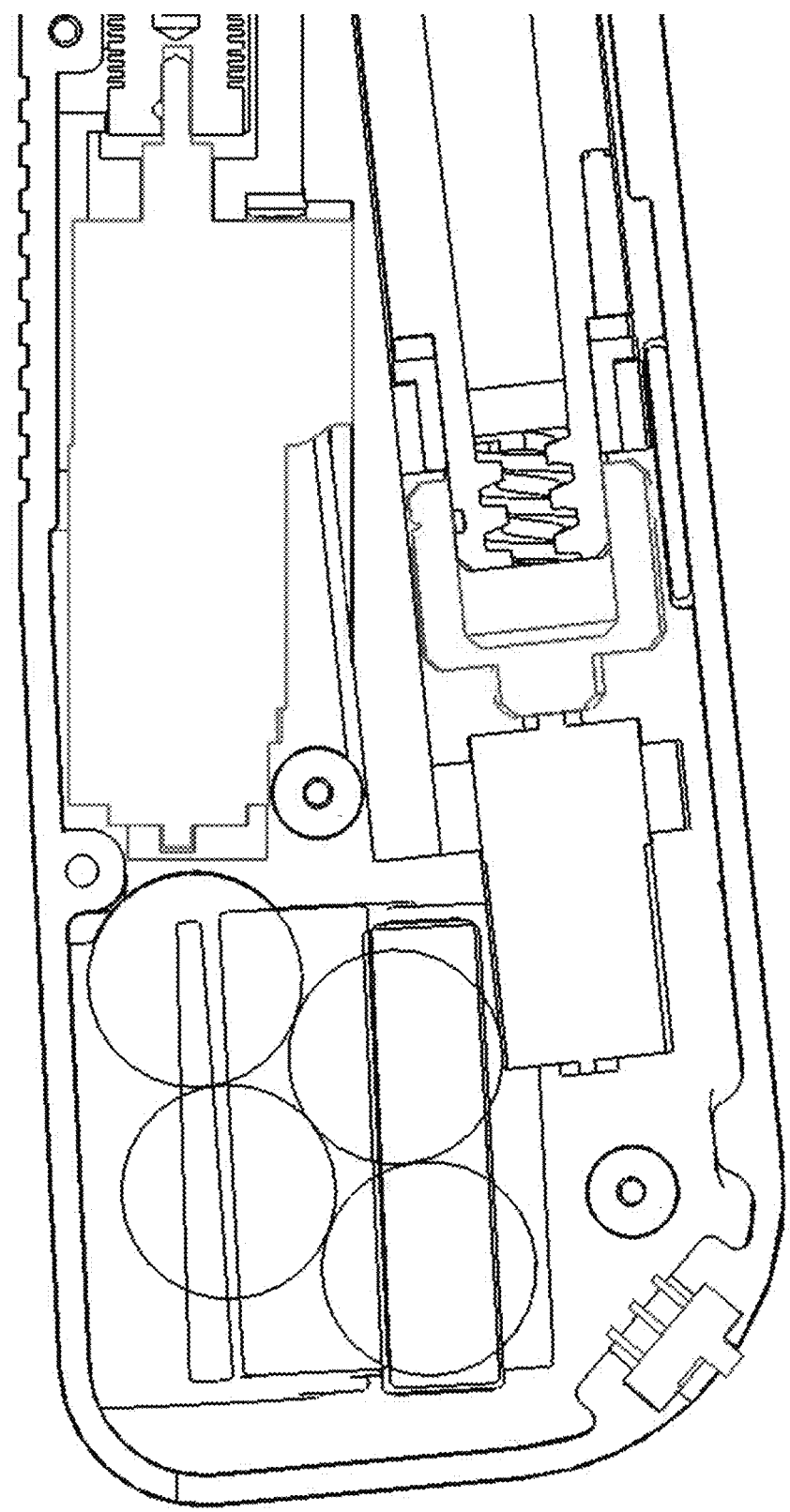
FIG. 13 is a fragmentary, enlarged, vertically cross-sectional view from the right side of a proximal handle body portion of the stapler of FIG. 12.

The powered stapler 1 has a handle body 10 containing three switches: an anvil open switch 20, an anvil close switch 21, and a staple firing switch 22. Each of these switches is electrically connected to a circuit board 500 (see FIG. 12) having circuitry programmed to carry out the stapling functions of the stapler 1. The circuit board 500 is electrically connected to a power supply 600 contained within the handle body 10. One exemplary embodiment utilizes 2 to 6 Lithium CR123 or CR2 cells as the power supply 600. Other power supply embodiments are possible, such as rechargeable batteries or a power converter that is connected to an electric mains (in the latter embodiment, the stapler would not be self-powered or self-contained). As used herein, the terms self-powered or self-contained when used with regard to the electric power supply (600) are interchangeable and mean that the power supply is a complete and independent unit in and of itself and can operate under its own power without the use of external power sources. For example, a power supply having an electric cord that is plugged into an electric mains during use is not self-powered or self-contained.

Insulated conductive wires or conductor tracks on the circuit board 500 connect all of the electronic parts of the stapler 1, such as an on/off switch 12, a tissue compression indicator 14, the anvil and firing switches 20, 21, 22, the circuit board 500, and the power supply 600, for example. But these wires and conductors are not shown in the figures of the drawings for ease of understanding and clarity.

The distal end of the handle body 10 is connected to a proximal end of a rigid anvil neck 30. Opposite this connection, at the distal end of the anvil neck 30, is a coupling device 40 for removably attaching a staple cartridge 50 and an anvil 60 thereto. Alternatively, the staple cartridge 50 can be non-removable in a single-use configuration of the stapler 1. These connections will be described in further detail below.

FIG. 2 shows the handle body 10 with the right half 13 of the handle body 10 and the circuit board 500 removed. As will be discussed below, a proximal backbone plate 70 is also removed from the view of FIG. 2 to allow viewing of the internal components inside the handle body 10 from the right side thereof. What can be seen from the view of FIG. 2 is that there exist two internal component axes within the handle body 10. A first of these axes is the staple control axis 80, which is relatively horizontal in the view of FIG. 2. The staple control axis 80 is the centerline on which lie the components for controlling staple actuation. The second of these axes is the anvil control axis 90 and is disposed at an angle to the staple control axis 80. The anvil control axis 90 is the centerline on which lie the components for controlling anvil actuation. It is this separation of axes 80, 90 that allows the electric stapler 1 to be powered using a handle body 10 that is small enough to fit in a physician's hand and that does not take up so much space that the physician becomes restricted from movement in all necessary directions and orientations.

Shown inside the handle body 10 is the on/off switch 12 (e.g., a grenade pin) for controlling power (e.g., battery power) to all of the electrical components and the tissue compression indicator 14. The tissue compression indicator 14 indicates to the physician that the tissue being compressed between the anvil 60 and the staple cartridge 50 has or has not been compressed with greater than a pre-set compressive force, which will be described in further detail below. This indicator 14 is associated with a force switch 400 that has been described in co-pending U.S. Patent Provisional Application Ser. No. 60/801,989 filed May 19, 2006, and titled "Force Switch" (the entirety of which is incorporated by reference herein).

The components along the anvil control axis 90 make up the anvil control assembly 100. An anvil control frame 110 is aligned along the anvil control axis 90 to house and/or fix various part of the anvil control assembly 100 thereto. The anvil control frame 110 has a proximal mount 112, an intermediate mount 114, and a distal mount 116. Each of these mounts 112, 114, 116 can be attached to or integral with the control frame 110. In the exemplary embodiment, for ease of manufacturing, the proximal mount 112 has two halves and is separate from the frame 110 and the intermediate mount 114 is separate from the frame 110.

At the proximal end of the anvil control assembly 100 is an anvil motor 120. The anvil motor 120 includes the drive motor and any gearbox that would be needed to convert the native motor revolution speed to a desired output axle revolution speed. In the present case, the drive motor has a native speed of approximately 10,000 rpm and the gearbox converts the speed down to between approximately 50 and 70 rpm at an axle 122 extending out from a distal end of the anvil motor 120. The anvil motor 120 is secured both longitudinally and rotationally inside the proximal mount 112.

A motor-shaft coupler 130 is rotationally fixed to the axle 122 so that rotation of the axle 122 translates into a corresponding rotation of the motor coupler 130.

Positioned distal of the coupler 130 is a rotating nut assembly 140. The nut assembly 140 is, in this embodiment, a two part device having a proximal nut half 141 and a distal nut half 142 rotationally and longitudinally fixed to the proximal nut half 141. It is noted that these nut halves 141, 142 can be integral if desired. Here, they are illustrated in two halves for ease of manufacturing. The proximal end of the nut assembly 140 is rotationally fixed to the distal end of the coupler 130. Longitudinal and rotational support throughout the length of these two connected parts is assisted by the intermediate 114 and distal 116 mounts.

Figure 3:
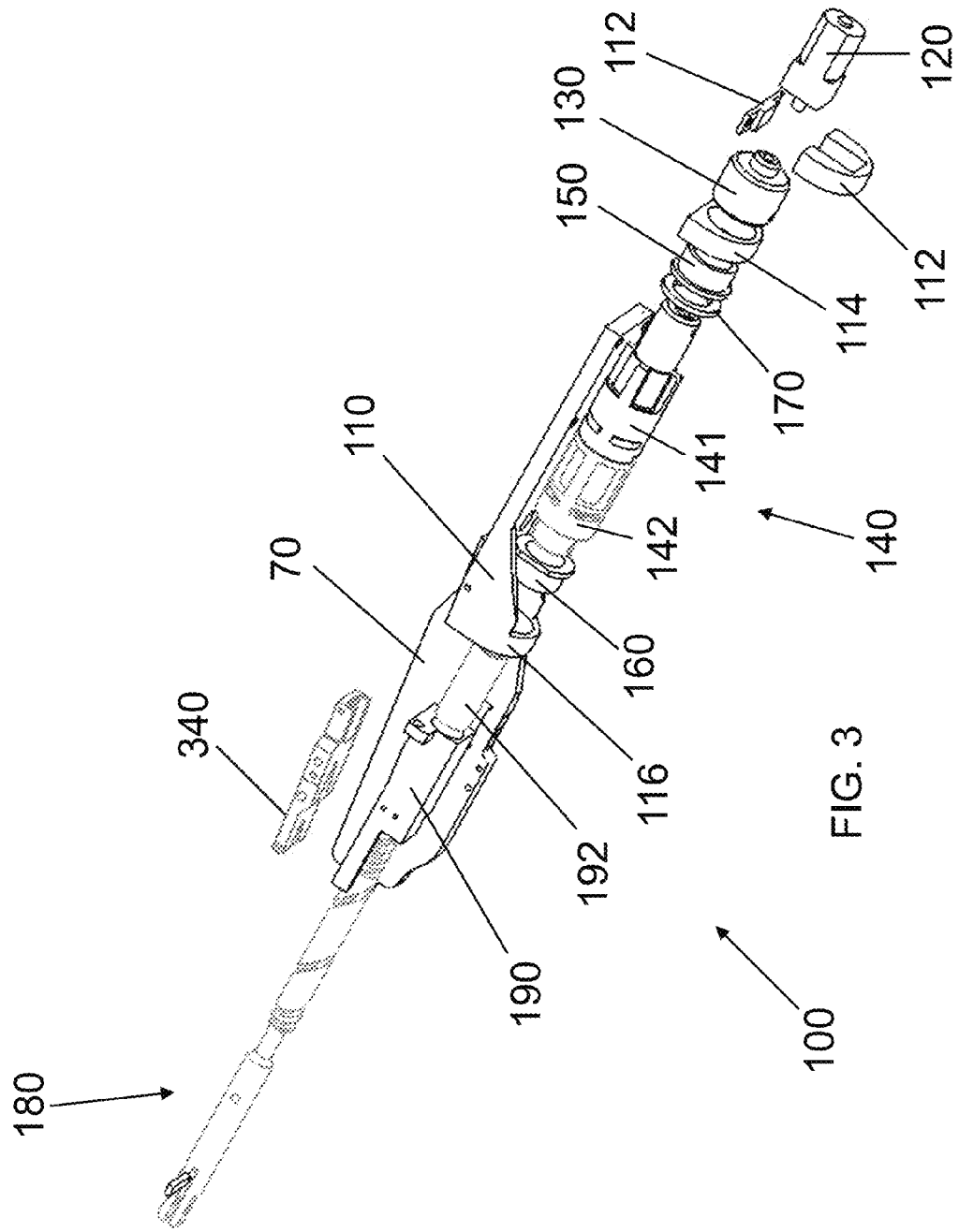
FIG. 3 is an exploded, perspective view of an anvil control assembly of the stapler of FIG. 1.

A proximal nut bushing 150 (see FIG. 3) is interposed between the intermediate mount 114 and the proximal nut half 141 and a distal nut bushing 160 is interposed between the distal mount 116 and the distal nut half 142 to have these parts spin efficiently and substantially without friction within the handle body 10 and the anvil control frame 110. The bushings 150, 160 can be of any suitable bearing material, for example, they can be of metal such as bronze or a polymer such as nylon. To further decrease the longitudinal friction between the rotating nut assembly 140 and the coupler 130, a thrust washer 170 is disposed between the proximal bushing 150 and the proximal nut half 141.

Figure 4:
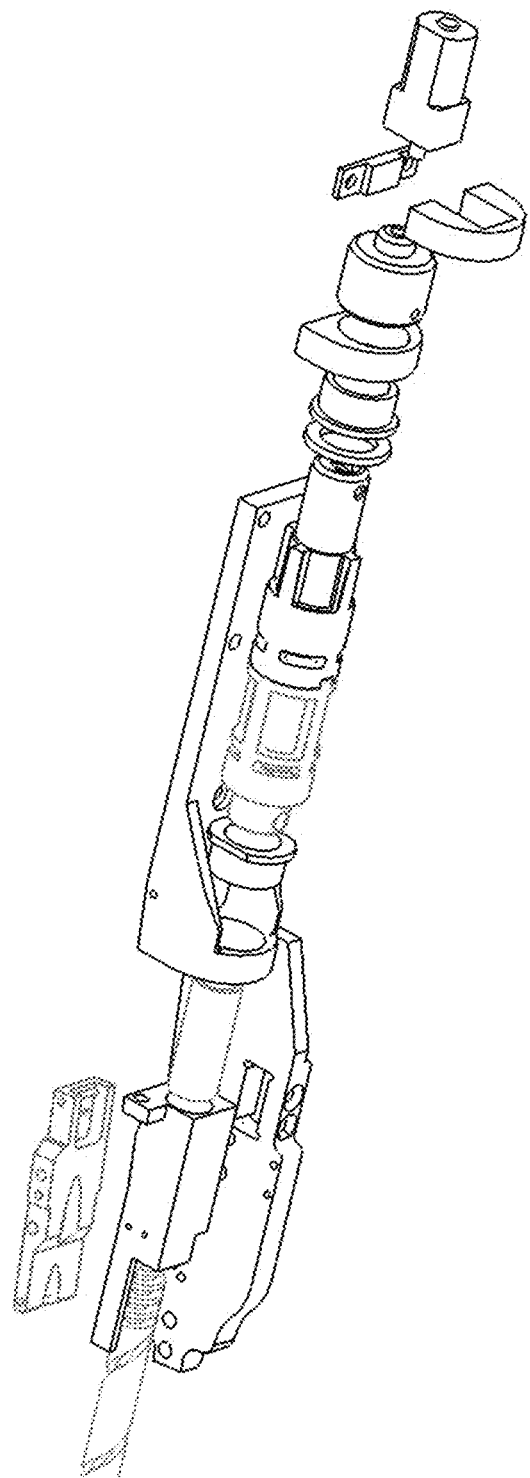
FIG. 4 is an enlarged, fragmentary, exploded, perspective view of the anvil control assembly of FIG. 3.

Rotation of the coupler 130 and nut assembly 140 is used to advance or retract a threaded rod 180, which is the mechanism through which the anvil 60 is extended or retracted. The threaded rod 180 is shown in further detail in the exploded view of FIGS. 3 to 4 and is described in further detail below. A rod support 190 is attached to a distal end of the anvil control frame 110 for extending the supporting surfaces inside the nut assembly 140 that keep the rod 180 aligned along the anvil control axis 90. The rod support 190 has a smooth interior shape corresponding to an external shape of the portion of the rod 180 that passes therethrough. This mating of shapes allows the rod 180 to move proximally and distally through the support 190 substantially without friction. To improve frictionless movement of the rod 180 through the support 190, in the exemplary embodiment, a cylindrical rod bushing 192 is disposed between the support 190 and the rod 180. The rod bushing 192 is not visible in FIG. 2 because it rests inside the support 190. However, the rod bushing 192 is visible in the exploded view of FIGS. 3 to 4. With the rod bushing 192 in place, the internal shape of the support 190 corresponds to the external shape of the rod bushing 192 and the internal shape of the rod bushing 192 corresponds to the external shape of the portion of the rod 180 that passes therethrough. The rod bushing 192 can be, for example, of metal such as bronze or a polymer such as nylon.

Figure 5:
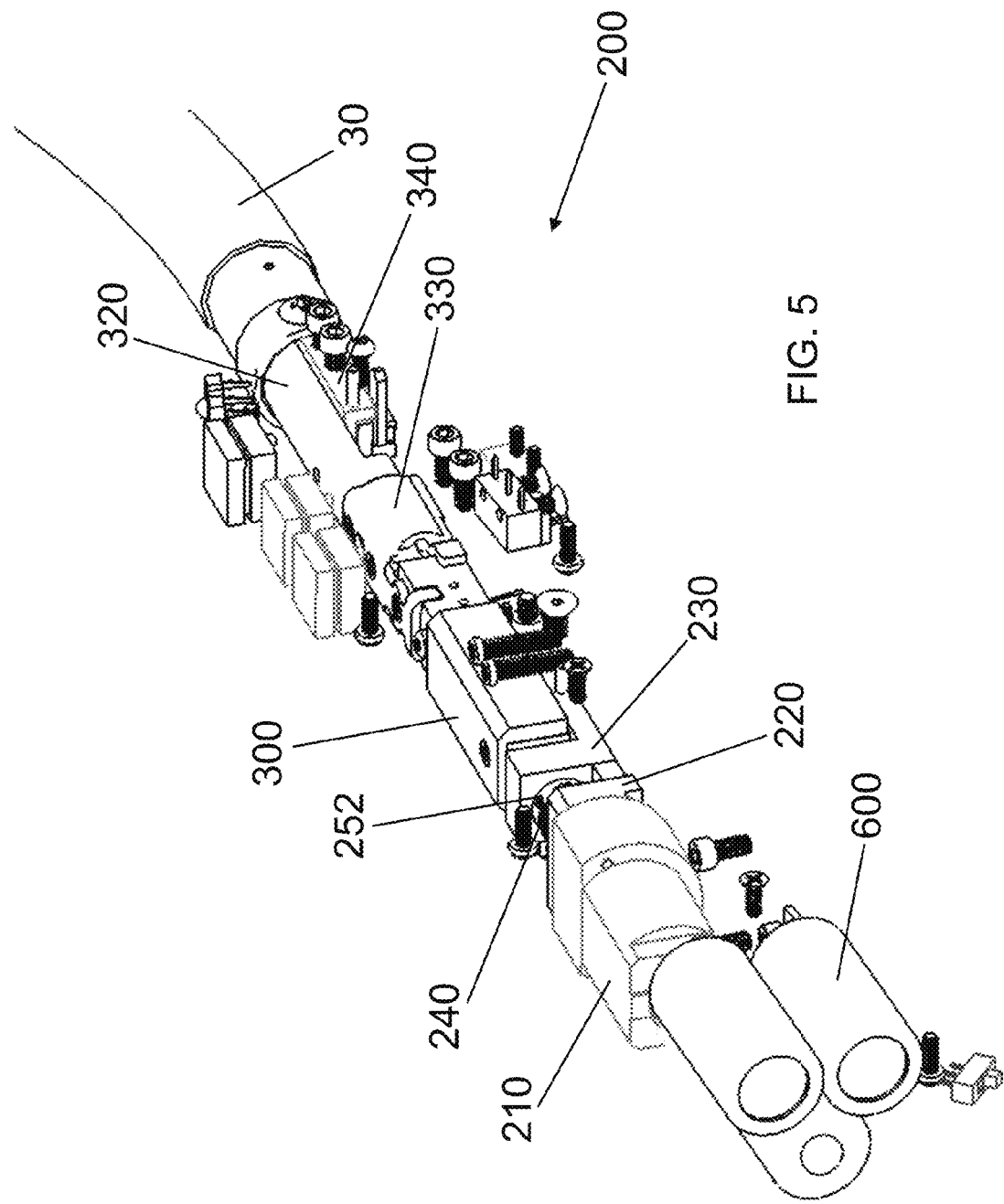
FIG. 5 is a fragmentary, perspective view of a staple firing control assembly of the stapler of FIG. 1 from a rear side thereof.
Figure 6:
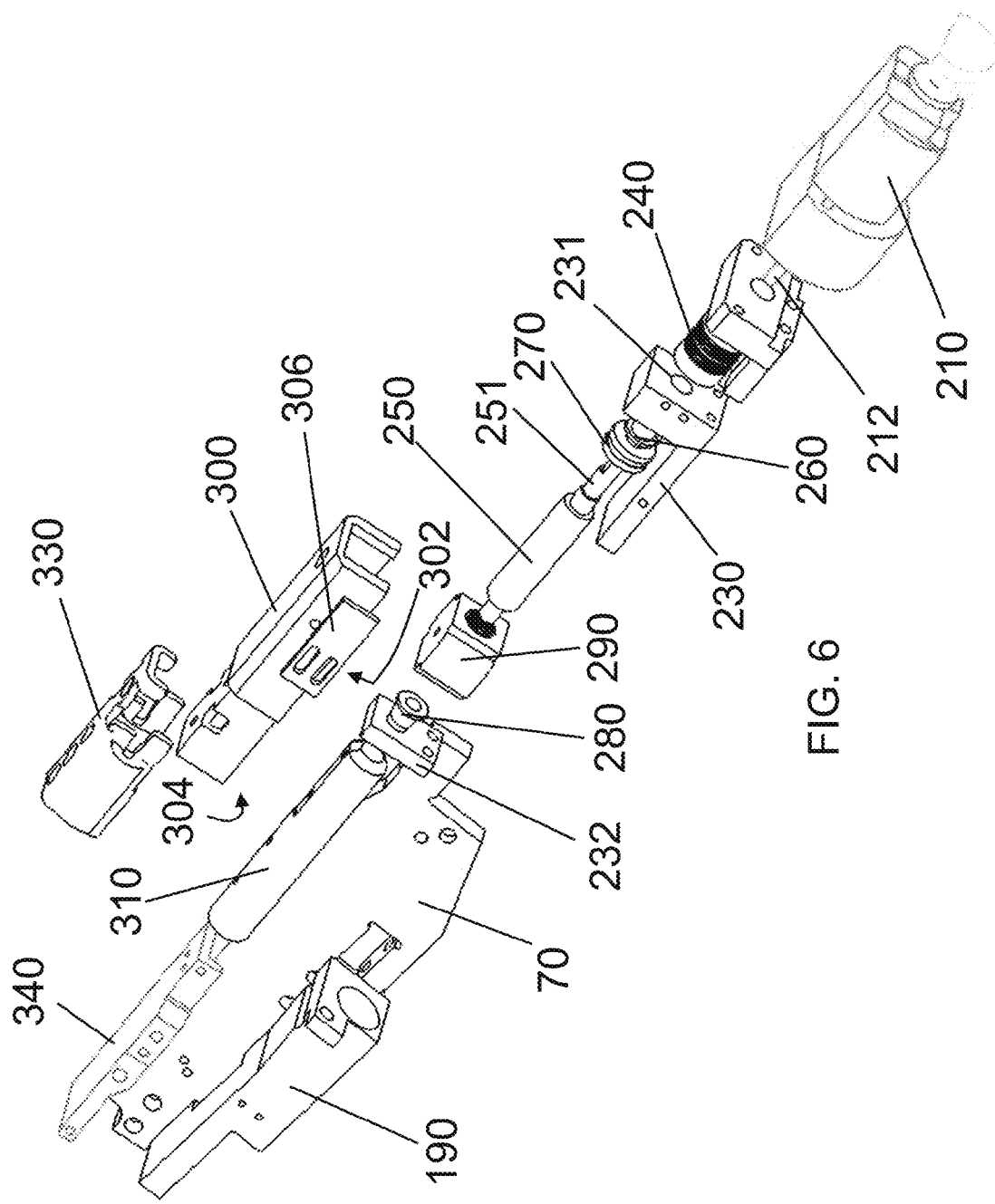
FIG. 6 is an exploded, perspective view of the staple firing control assembly of the stapler of FIG. 1.
Figure 7:
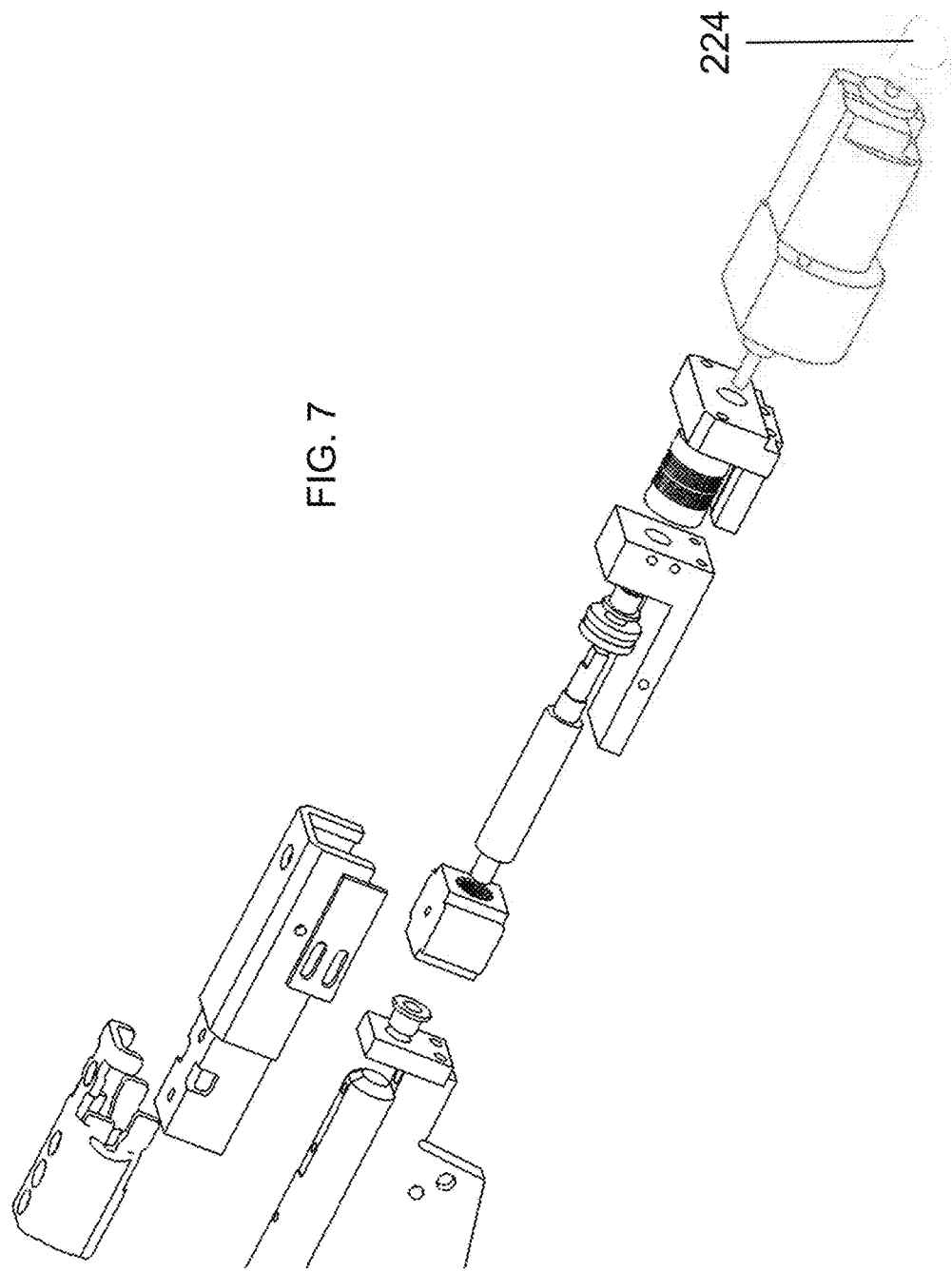
FIG. 7 is an enlarged, fragmentary, exploded, perspective view of the staple firing control assembly of FIG. 6.
Figure 8:
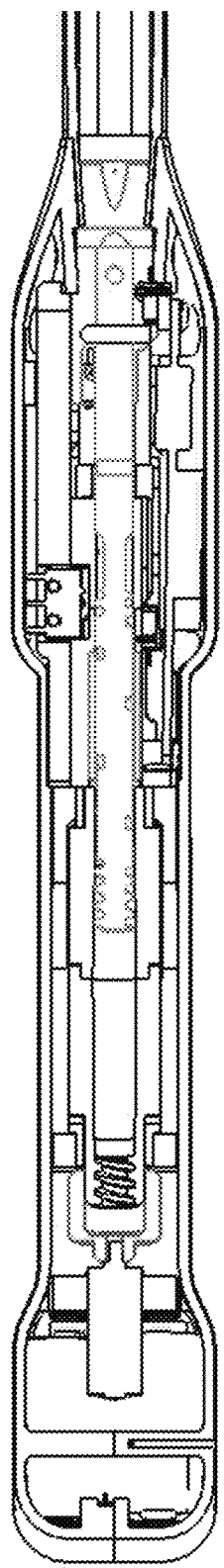
FIG. 8 is a fragmentary, horizontally cross-sectional view of the anvil control assembly from below the handle body portion of the stapler of FIG. 1.
Figure 9:
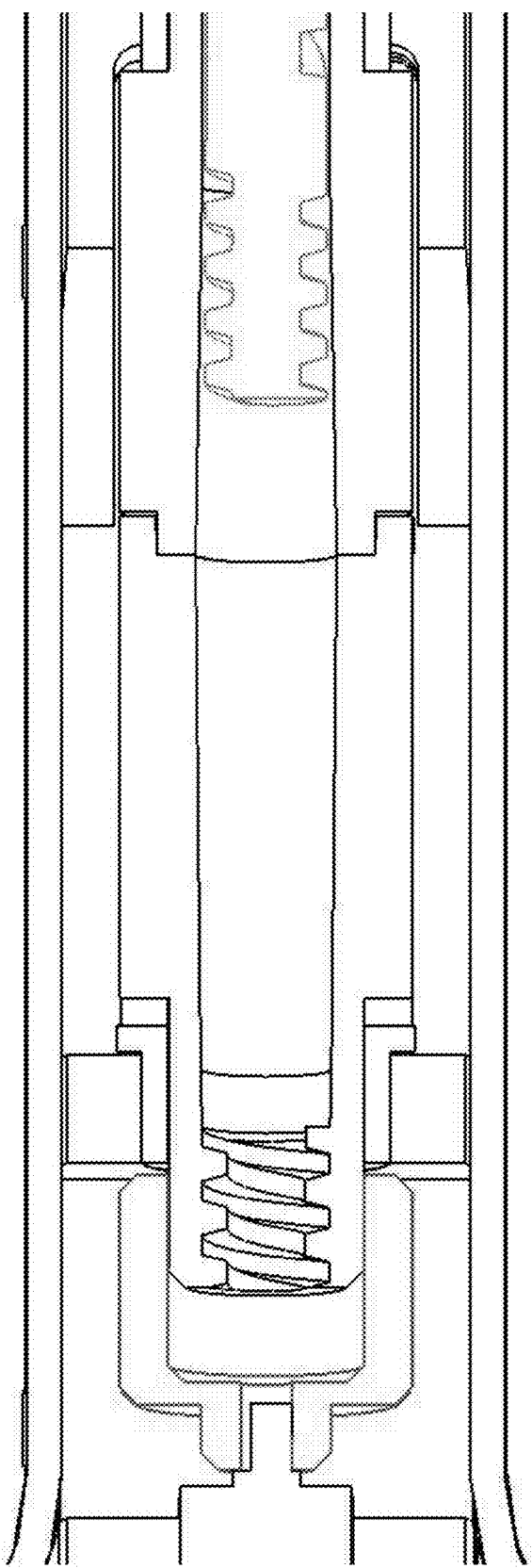
FIG. 9 is a fragmentary, enlarged, horizontally cross-sectional view from below a proximal portion of the anvil control assembly FIG. 8.
Figure 10:
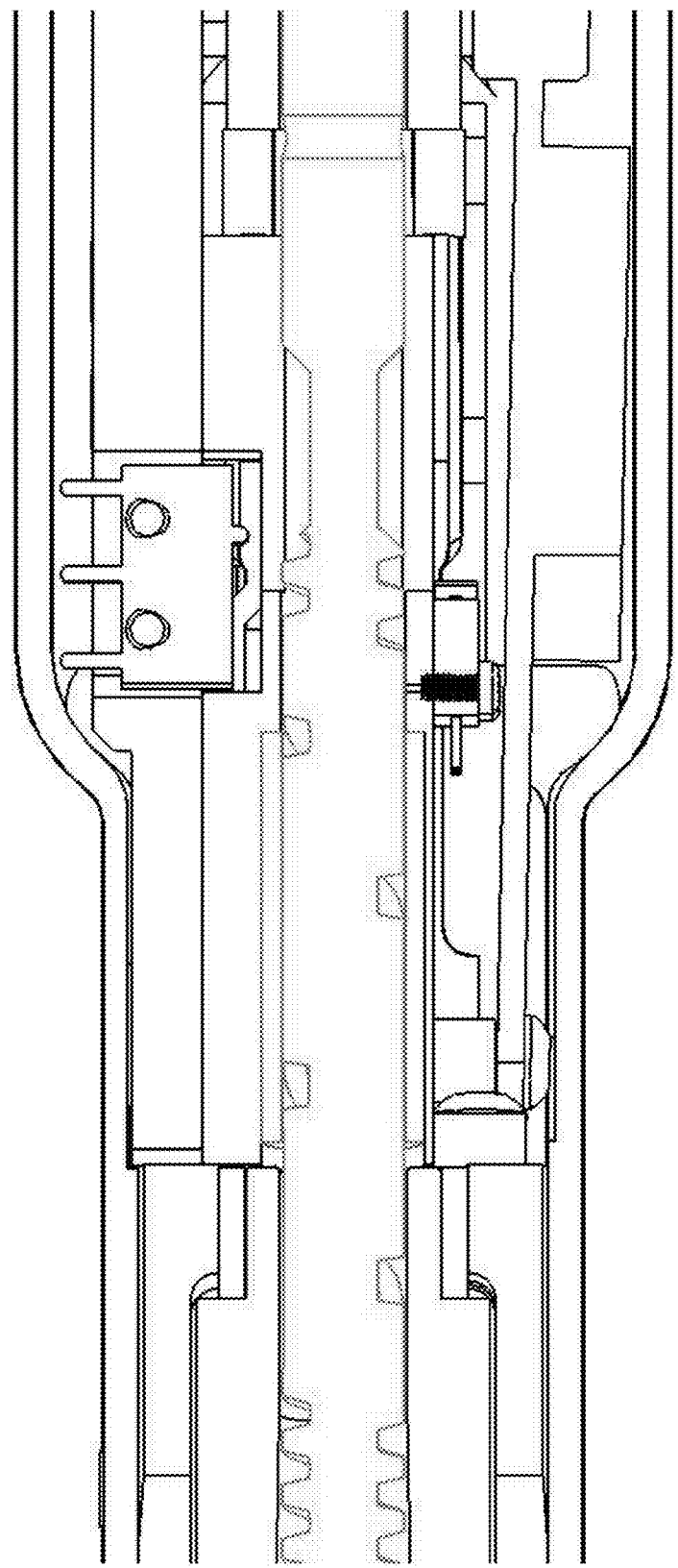
FIG. 10 is a fragmentary, enlarged, horizontally cross-sectional view from below an intermediate portion of the anvil control assembly of FIG. 8.
Figure 11:
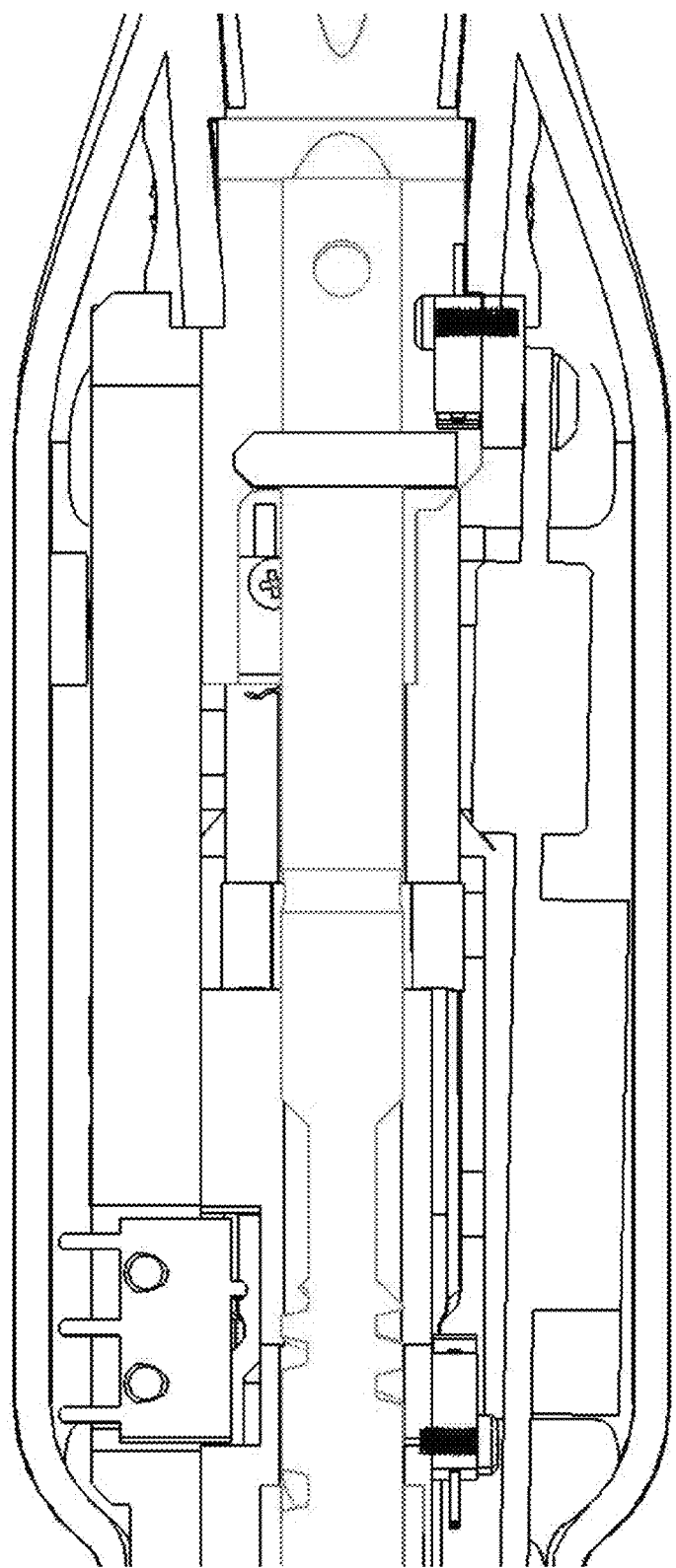
FIG. 11 is a fragmentary, enlarged, horizontally cross-sectional view from below a distal portion of the anvil control assembly of FIG. 8.

The components along the staple control axis 80 form the staple control assembly 200. The staple control assembly 200 is illustrated in FIG. 5 viewed from a proximal upper and side perspective. The proximal end of the staple control assembly 200 includes a stapling motor 210. The stapling motor 210 includes the drive motor and any gearbox that would be needed to convert the native motor revolution speed to a desired revolution speed. In the present case, the drive motor has a native speed of approximately 20,000 rpm and the gearbox converts the speed to approximately 200 rpm at an output axle 212 at the distal end of the gearbox. The axle 212 cannot be seen in the view of FIG. 5 but can be seen in the exploded view of FIGS. 6 to 7.

The stapling motor 210 is rotationally and longitudinally fixed to a motor mount 220. Distal of the motor mount 220 is an intermediate coupling mount 230. This coupling mount 230 has a distal plate 232 that is shown, for example in FIG. 6. The distal plate 232 is removable from the coupling mount 230 so that a rotating screw 250 can be held therebetween. It is this rotating screw 250 that acts as the drive for ejecting the staples out of the staple cartridge 50. The efficiency in transferring the rotational movement of axle 212 to the rotating screw 250 is a factor that can substantially decrease the ability of the stapler 1 to deliver the necessary staple ejection longitudinal force of up to 250 pounds. Thus, an exemplary embodiment of the screw 250 has an acme profile thread.

There are two exemplary ways described herein for efficiently coupling the rotation of the axle 212 to the screw 250. First, the stapling motor 210 can be housed "loosely" within a chamber defined by the handle body 10 so that it is rotationally stable but has play to move radially and so that it is longitudinally stable but has play to move. In such a configuration, the stapling motor 210 will "find its own center" to align the axis of the axle 212 to the axis of the screw 250, which, in the exemplary embodiment, is also the staple control axis 80.

A second exemplary embodiment for aligning the axle 212 and the screw 250 is illustrated in FIGS. 1 to 5, for example. In this embodiment, a proximal end of a flexible coupling 240 is fixed (both rotationally and longitudinally) to the axle 212. This connection is formed by fitting the distal end of the axle 212 inside a proximal bore 241 of the flexible coupling 240. See FIG. 12. The axle 212 is, then, secured therein with a proximal setscrew 213. The screw 250 has a proximal extension 251 that fits inside a distal bore 242 of the flexible coupling 240 and is secured therein by a distal setscrew 252. It is noted that the figures of the drawings show the flexible coupling 240 with ridges in the middle portion thereof. In an exemplary embodiment of the coupling 240, the part is of aluminum or molded plastic and has a spiral or helixed cut-out around the circumference of the center portion thereof. In such a configuration, one end of the coupling 240 can move in any radial direction (360 degrees) with respect to the other end (as in a gimbal), thus providing the desired flex to efficiently align the central axes of the axle 212 and the screw 250.

The proximal extension 251 of the screw 250 is substantially smaller in diameter than the diameter of the bore 231 that exists in and through the intermediate coupling mount 230. This bore 231 has two increasing steps in diameter on the distal side thereof. The first increasing step in diameter is sized to fit a proximal radius screw bushing 260, which is formed of a material that is softer than the intermediate coupling mount 230. The proximal radius screw bushing 260 only keeps the screw 250 axially aligned and does not absorb or transmit any of the longitudinal thrust. The second increasing step in diameter is sized to fit a proximal thrust bearing 270 for the screw 250. In an exemplary embodiment of the thrust bearing 270, proximal and distal plates sandwich a bearing ball retainer plate and bearing balls therebetween. This thrust bearing 270 absorbs all of the longitudinal thrust that is imparted towards the axle 212 while the up to 250 pounds of longitudinal force is being applied to eject the staples in the staple cartridge 50. The proximal extension 251 of the screw 250 has different sized diameters for each of the interiors of the screw bushing 260 and the thrust bearing 270. The motor mount 220 and the coupling mount 230, therefore, form the two devices that hold the flexible coupling 240 therebetween.

The rotating screw 250 is held inside the distal plate 232 with a distal radius screw bushing 280 similar to the proximal radius screw bushing 260. Thus, the screw 250 rotates freely within the distal plate 232. To translate the rotation of the screw 250 into a linear distal movement, the screw 250 is threaded within a moving nut 290. Movement of the nut 290 is limited to the amount of movement that is needed for complete actuation of the staples; in other words, the nut 290 only needs to move through a distance sufficient to form closed staples between the staple cartridge 50 and the anvil 60 and to extend the cutting blade, if any, within the staple cartridge 50, and then retract the same. When the nut 290 is in the proximal-most position (see, e.g., FIG. 12), the staples are at rest and ready to be fired. When the nut 290 is in the distal-most position, the staples are stapled through and around the tissue interposed between the staple cartridge 50 and the anvil, and the knife, if any, is passed entirely through the tissue to be cut. The distal-most position of the nut 290 is limited by the location of the distal plate 232. Thus, the longitudinal length of the threads of the screw 250 and the location of the distal plate 232 limit the distal movement of the nut 290.

Frictional losses between the screw 250 and the nut 290 contribute to a significant reduction in the total pounds of force that can be transmitted to the staple cartridge 50 through the cartridge plunger 320. Therefore, it is desirable to select the materials of the screw 250 and the nut 290 and the pitch of the threads of the screw 250 in an optimized way. It has been found that use of a low-friction polymer for manufacturing the nut 290 will decrease the friction enough to transmit the approximately 250 pounds of longitudinal force to the distal end of the cartridge plunger 320—the amount of force that is needed to effectively deploy the staples. Two particular exemplary materials provide the desired characteristics and are referred to in the art as DELRIN® AF Blend Acetal (a thermoplastic material combining TEFLON® fibers uniformly dispersed in DELRIN® acetal resin) and RULON® (a compounded form of TFE fluorocarbon) or other similar low-friction polymers.

A nut coupling bracket 300 is longitudinally fixed to the nut 290 so that it moves along with the nut 290. The nut coupling bracket 300 provides support for the relatively soft, lubricious nut material. In the exemplary embodiment shown, the bracket 300 has an interior cavity having a shape corresponding to the exterior shape of the nut 290. Thus, the nut 290 fits snugly into the coupling bracket 300 and movement of the nut 290 translates into a corresponding movement of the nut coupling bracket 300. The shape of the nut coupling bracket 300 is, in the exemplary embodiment, dictated by the components surrounding it and by the longitudinal forces that it has to bear. For example, there is an interior cavity 302 distal of the nut 290 that is shaped to receive the distal plate 232 therein. The nut coupling bracket 300 also has a distal housing 304 for receiving therein a stiffening rod 310. The stiffening rod 310 increases the longitudinal support and forms a portion of the connection between the nut 290 and a cartridge plunger 320 (see, i.e., FIG. 5), which is the last moving link between elements in the handle body 10 and the staple cartridge 50. A firing bracket 330, disposed between the distal end of the nut coupling bracket 300 and the stiffening rod 310, strengthens the connection between the nut coupling bracket 300 and the rod 310.

Various components of the stapler 1 are connected to one another to form a backbone or spine. This backbone is a frame providing multi-directional stability and is made up of four primary parts (in order from proximal to distal): the anvil control frame 110, the proximal backbone plate 70 (shown in FIGS. 3 to 4 and 6 to 7), a distal backbone plate 340, and the anvil neck 30. Each of these four parts is longitudinally and rotationally fixed to one another in this order and forms the skeleton on which the remainder of the handle components is attached in some way. Lateral support to the components is provided by contours on the inside surfaces of the handle body 10, which in an exemplary embodiment is formed of two halves, a left half 11 and a right half 13. Alternatively, support could be single frame, stamped, or incorporated into the handle halves 11, 13.

Functionality of the anvil control assembly 100 is described with regard to FIGS. 17 to 27. To carry out a stapling procedure with the stapler 1, the anvil 60 is removed entirely from the stapler 1 as shown in FIG. 17. The anvil open switch 20 is depressed to extend the distal end of the trocar tip 410 housed within the staple cartridge and which is longitudinally fixedly connected to the screw 250. The point of the trocar tip 410 can, now, be passed through or punctured through tissue that is to be stapled. The user can, at this point, replace the anvil 60 onto the trocar tip 410 from the opposite side of the tissue (see FIG. 18) and, thereby, lock the anvil 60 thereon. The anvil closed switch 22 can be actuated to begin closing the anvil 60 against the staple cartridge 50 and pinch the tissue therebetween within an anvil-cartridge gap 62.

Figure 14:
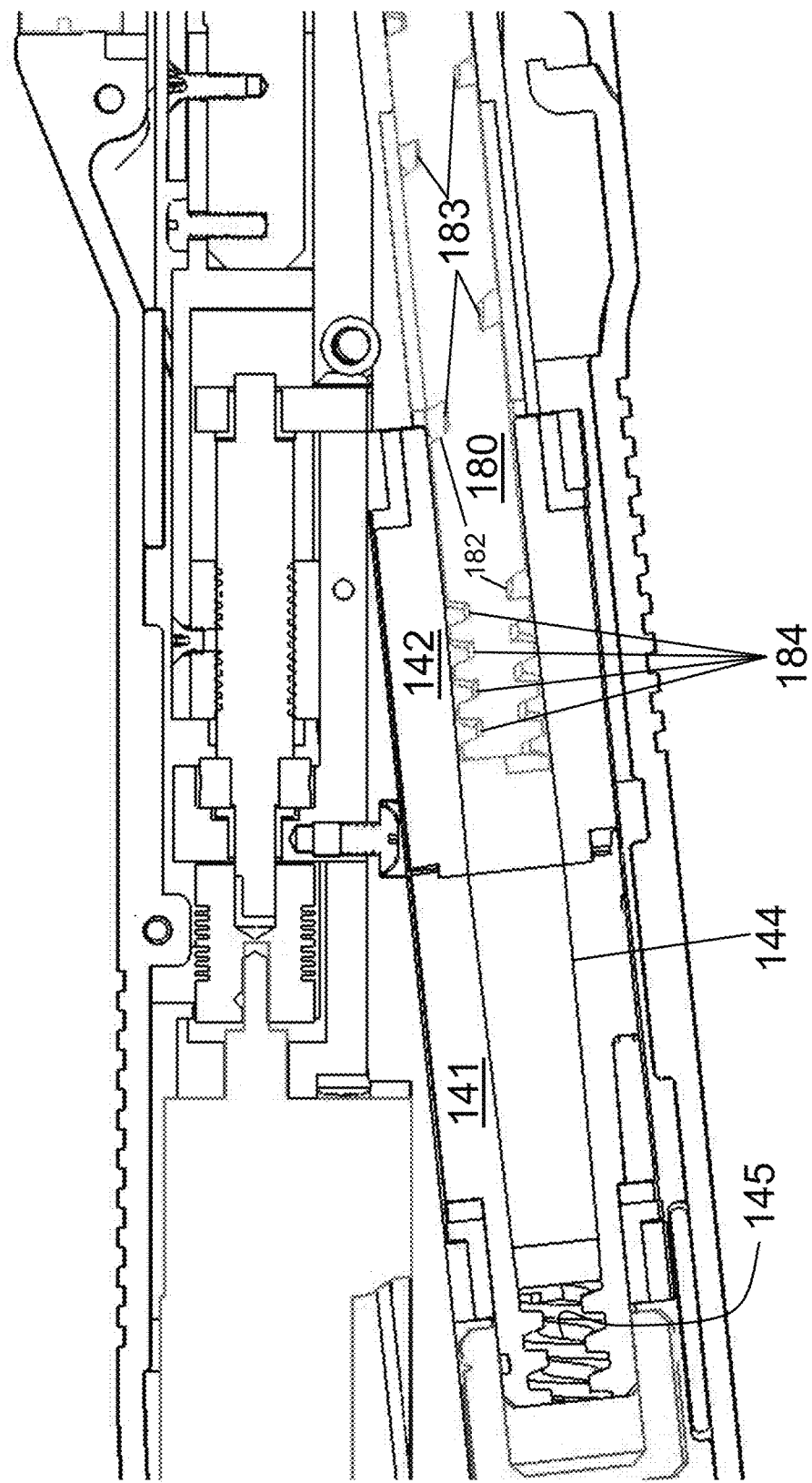
FIG. 14 is a fragmentary, enlarged, vertically cross-sectional view from the right side of an intermediate handle body portion of the stapler of FIG. 12.
Figure 15:
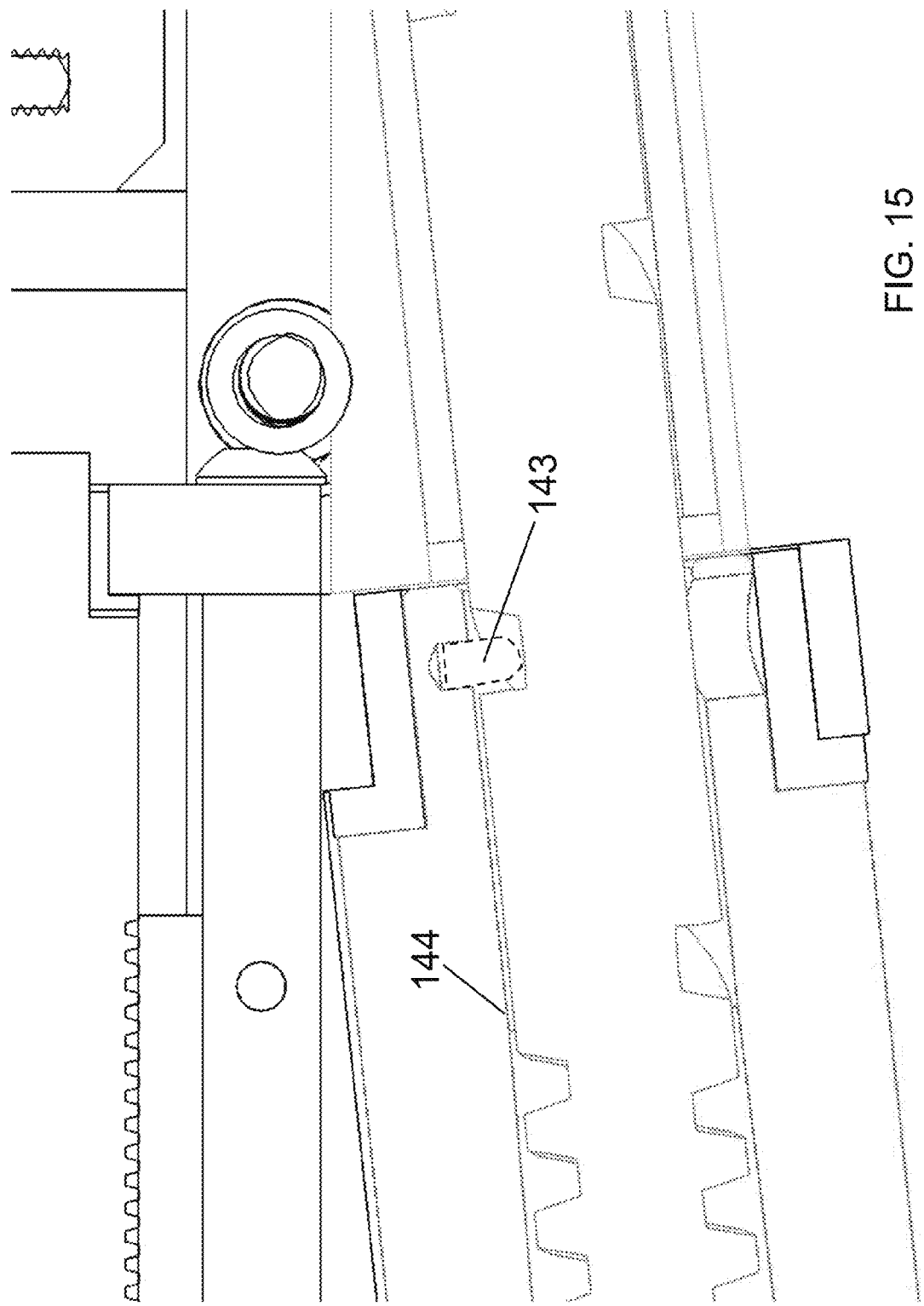
FIG. 15 is a fragmentary, further enlarged, vertically cross-sectional view from the right side of the intermediate handle body portion of the stapler of FIG. 14.
Figure 16:
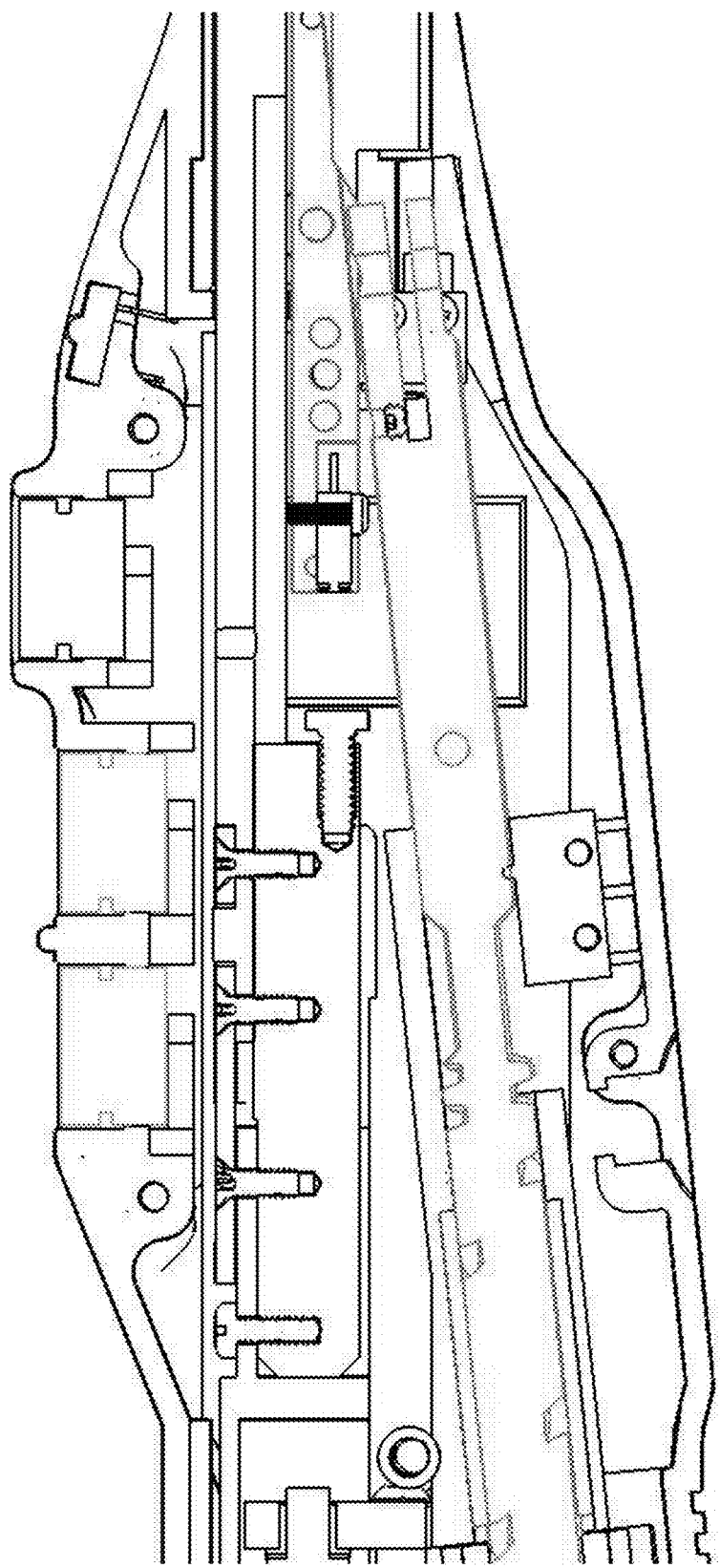
FIG. 16 is a fragmentary, enlarged, vertically cross-sectional view from the right side of a distal handle body portion of the stapler of FIG. 12.
Figure 19:
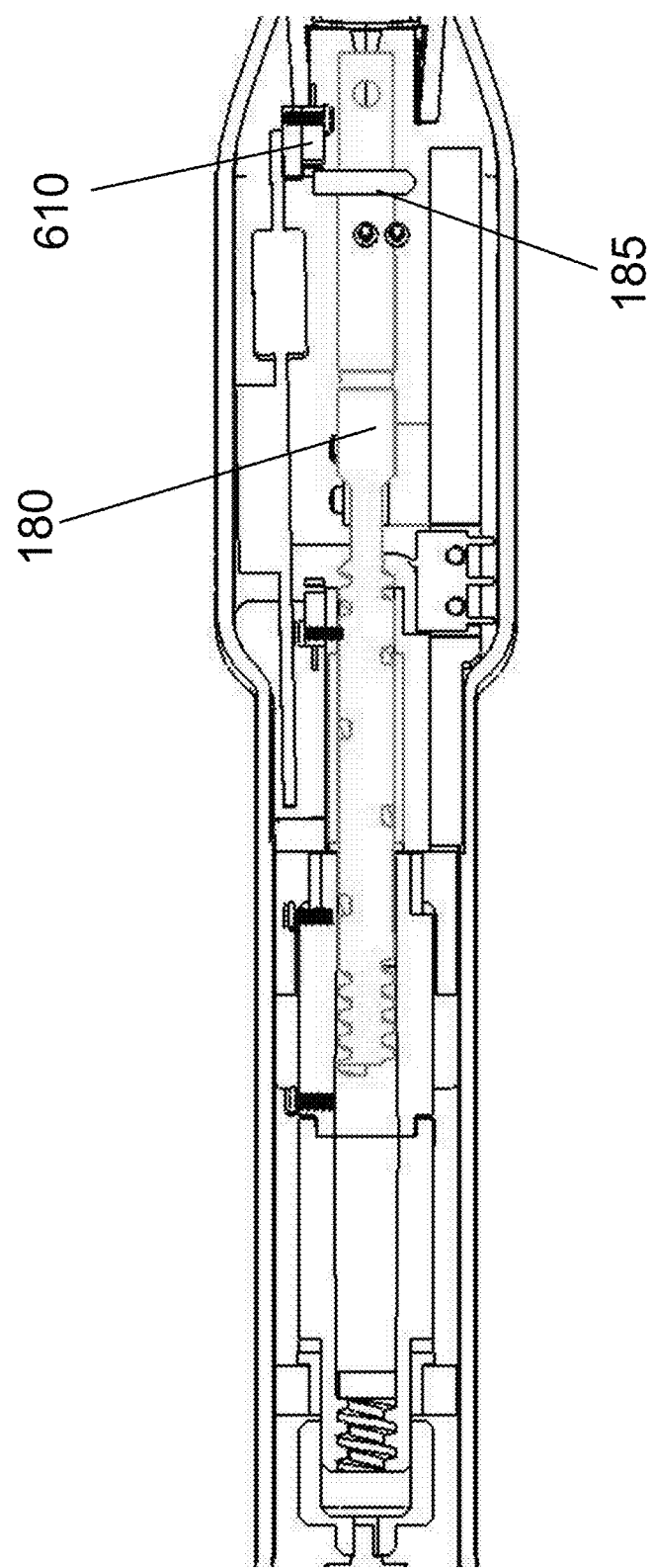
FIG. 19 is a fragmentary, horizontally cross-sectional view of the anvil control assembly from above the handle body portion of the stapler of FIG. 1 with the anvil rod in a fully extended position.
Figure 20:
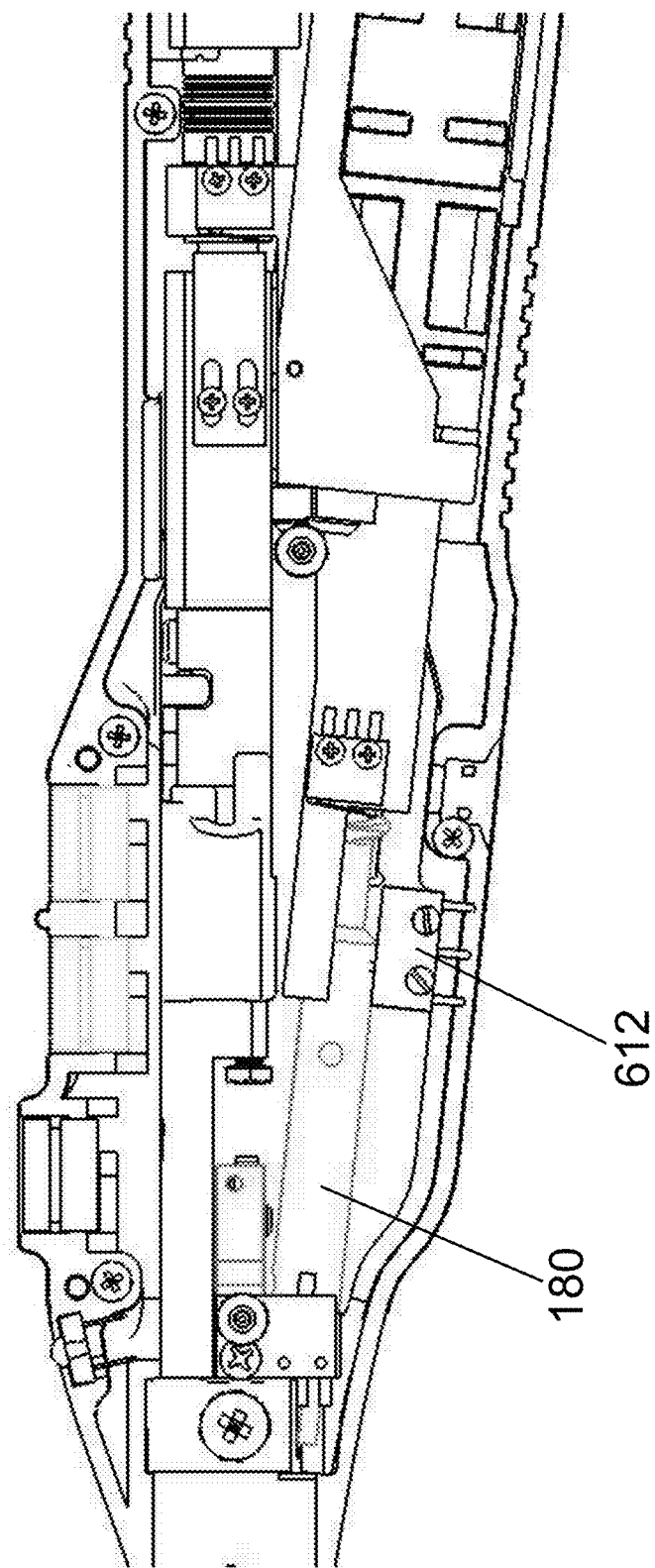
FIG. 20 is a fragmentary, side elevational view of the handle body portion of the stapler of FIG. 1 from a left side of the handle body portion with the left handle body and the circuit board removed and with the anvil rod in a fully extended position.
Figure 21:
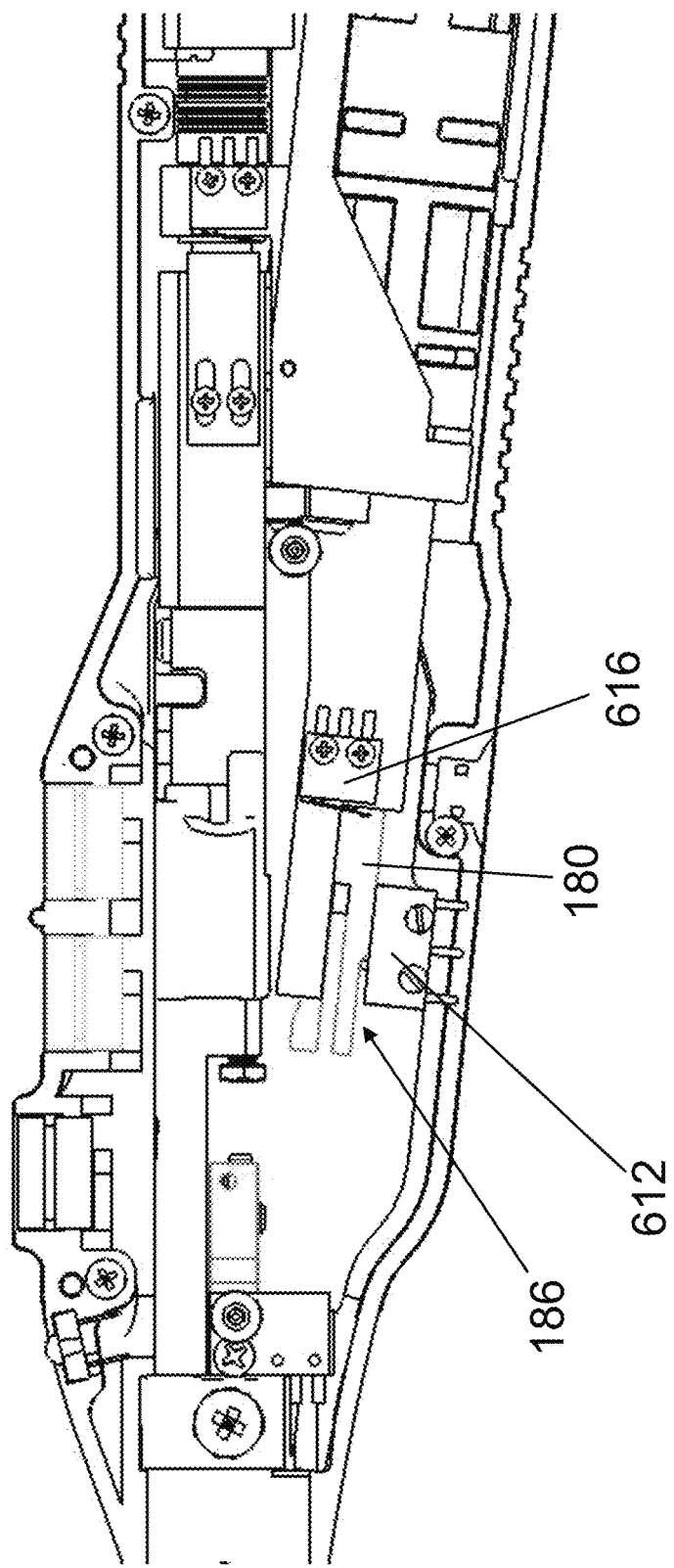
FIG. 21 is a fragmentary, side elevational view of the handle body portion of the stapler of FIG. 20 with the anvil rod in a 1-cm anvil closure position.

To describe how the trocar tip controlling movement of the anvil 60 occurs, reference is made to FIGS. 8 to 10, 14 to 15, and 18. As shown in dashed lines in FIG. 15, a rod-guiding pin 143 is positioned within the central bore 144 of the distal nut half 142. As the threaded rod 180 is screwed into the rotating nut 140, 141, 142, the pin 143 catches the proximal end of the thread 182 to surround the pin 143 therein. Thus, rotation of the nut 140 with the pin 143 inside the thread 182 will cause proximal or distal movement of the rod 180, depending on the direction of nut rotation. The thread 182 has a variable pitch, as shown in FIGS. 14 to 15, to move the anvil 60 at different longitudinal speeds. When the pin 143 is inside the longer (lower) pitched thread portion 183, the anvil 60 moves longitudinally faster. In comparison, when the pin 143 is inside the shorter (higher) pitched thread portion 184, the anvil 60 moves longitudinally slower. It is noted that the pin 143 is the only portion contacting the thread 182 when in the longer pitched thread portion 183. Thus, the pin 143 is exposed to the entire longitudinal force that is acting on the rod 180 at this point in time. The pin 143 is strong enough to bear such forces but may not be sufficient to withstand all longitudinal force that could occur with anvil 60 closure about interposed tissue.

As shown in FIG. 14, the rod 180 is provided with a shorter pitched thread portion 184 to engage in a corresponding internal thread 145 at the proximal end of the central bore 144 of the proximal nut half 141. When the shorter pitched thread portion 184 engages the internal thread 145, the entire transverse surface of the thread portion 184 contacts the internal thread 145. This surface contact is much larger than the contact between the pin 143 and any portion of the thread 182 and, therefore, can withstand all the longitudinal force that occurs with respect to anvil 60 closure, especially when the anvil 60 is closing about tissue during the staple firing state. For example, in the exemplary embodiment, the pin 143 bears up to approximately 30 to 50 pounds of longitudinal force. This is compared to the threads, which can hold up to 400 pounds of longitudinal force—an almost 10-to-1 difference.

An alternative exemplary embodiment of anvil control assembly 100 can entirely remove the complex threading of the rod 180. In such a case, the rod 180 has a single thread pitch and the anvil motor 120 is driven (through corresponding programming in the circuit board 500) at different speeds dependent upon the longitudinal position of the single-thread rod 180.

In any embodiment for driving the motors 120, 210, the control programming can take many forms. In one exemplary embodiment, the microcontroller on the battery powered circuit board 500 can apply pulse modulation (e.g., pulse-width, pulse-frequency) to drive either or both of the motors. Further, because the stapler 1 is a device that has a low duty cycle, or is a one-use device, components can be driven to exceed acceptable manufacturers' specifications. For example, a gear box can be torqued beyond its specified rating. Also, a drive motor, for example, a 6 volt motor, can be overpowered, for example, with 12 volts.

Closure of the anvil 60 from an extended position to a position in which the tissue is not compressed or is just slightly compressed can occur rapidly without causing damage to the interposed tissue. Thus, the longer-pitched thread portion 183 allows the user to quickly close the anvil 60 to the tissue in a tissue pre-compressing state. Thereafter, it is desirable to compress the tissue slowly so that the user has control to avoid over-compression of the tissue. As such, the shorter pitched thread portion 184 is used over this latter range of movement and provides the user with a greater degree of control. During such compression, the force switch 400 seen in FIG. 18 and described in co-pending U.S. Patent Provisional Application Ser. No. 60/801,989 can be used to indicate to the user through the tissue compression indicator 14 (and/or to the control circuitry of the circuit board 500) that the tissue is being compressed with a force that is greater than the pre-load of the spring 420 inside the force switch 400. It is noted that FIG. 18 illustrates the force switch 400 embodiment in the normally-open configuration described as the first exemplary embodiment of U.S. Patent Provisional Application Ser. No. 60/801,989. A strain gauge can also be used for measuring tissue compression.

Figure 22:
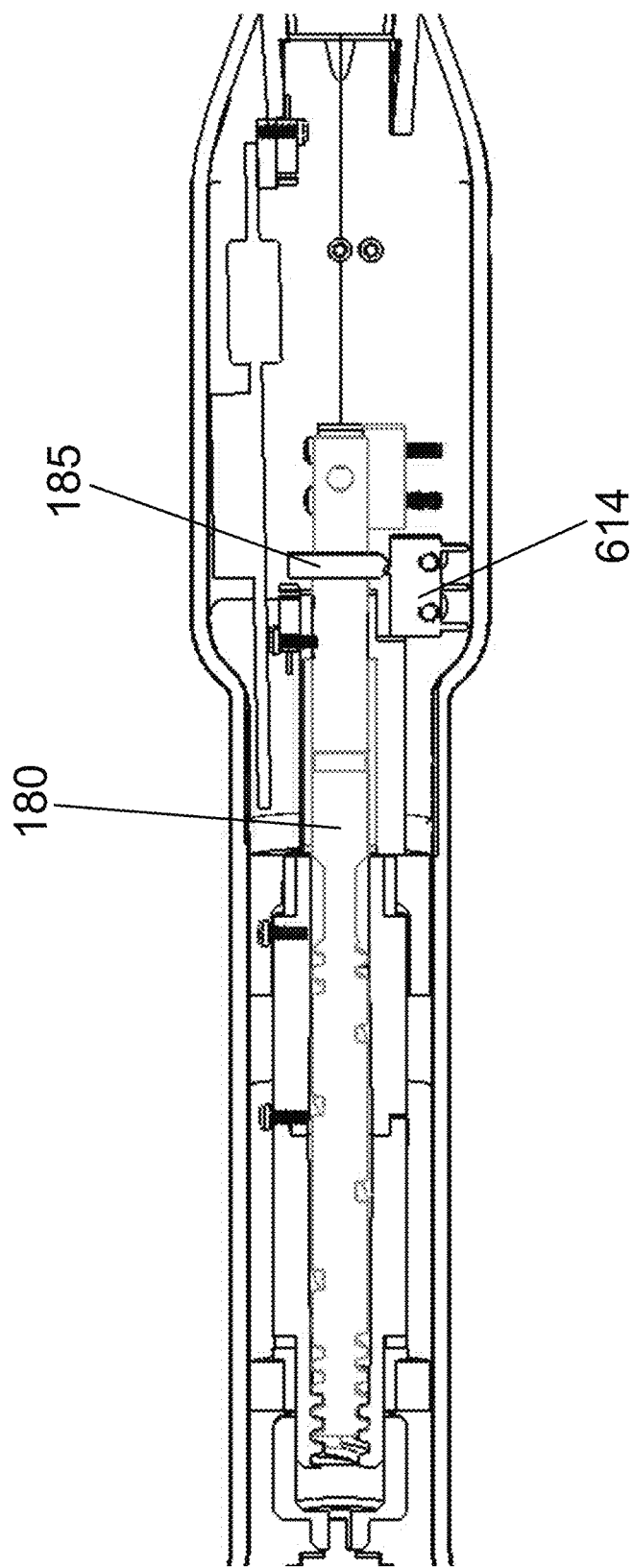
FIG. 22 is a fragmentary, horizontally cross-sectional view of the anvil control assembly from above the handle body portion of the stapler of FIG. 1 with the anvil rod in a safe staple firing position.
Figure 23:
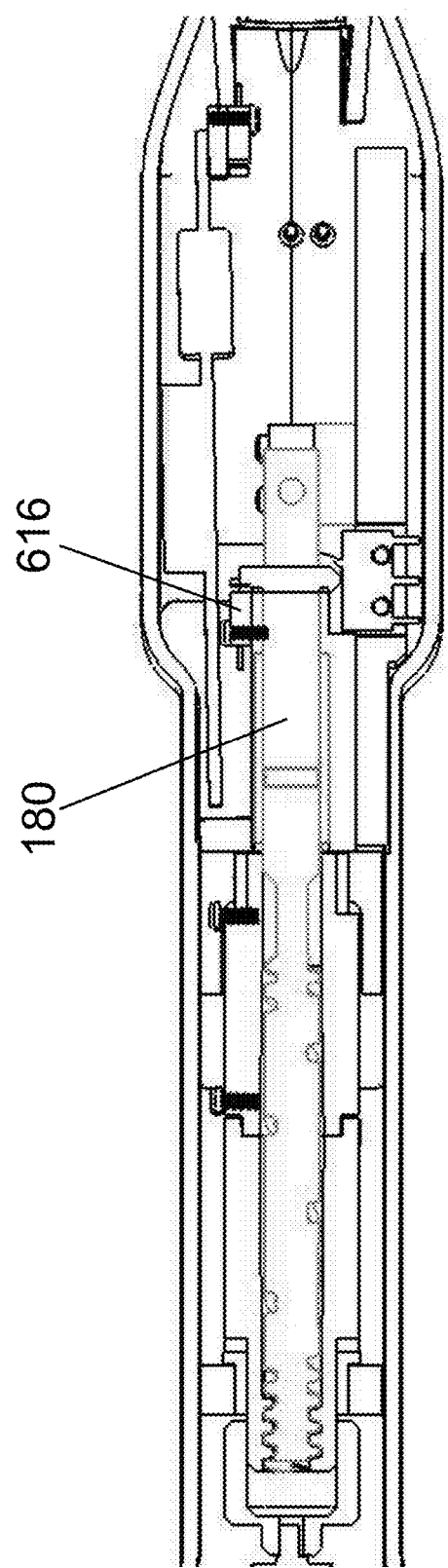
FIG. 23 is a fragmentary, horizontally cross-sectional view of the anvil control assembly from above the handle body portion of the stapler of FIG. 1 with the anvil rod in a fully retracted position.

FIGS. 19 to 23 illustrate movement of the rod 180 from an anvil-extended position (see FIGS. 19 to 20), to a 1-cm-closure-distance position (see FIG. 21), to a staple-fire-ready position (see FIG. 22), and, finally, to an anvil fully closed position (see FIG. 23). Movement of the rod 180 is controlled electrically (via the circuit board 500) by contact between a portion of a cam surface actuator 185 on the rod 180 and actuating levers or buttons of a series of micro-switches positioned in the handle body 10.

A rod-fully-extended switch 610 (see FIG. 19) is positioned distal in the handle body 10 to have the actuator 185 compress the activation lever of the rod-fully-extended switch 610 when the rod 180 (and, thereby, the anvil 60) is in the fully extended position. A 1-cm switch 612 is positioned in an intermediate position within the handle body 10 (see FIGS. 20 to 21) to prevent a 1-cm cam surface portion 186 of the rod 180 from pressing the activation button of the 1-cm switch 612 when the rod 180 (and, thereby, the anvil 60) is within 1 cm of the fully closed position. After passing the 1-cm closure distance, as shown in FIG. 22, the cam surface actuator 185 engages a staple-fire-ready switch 614. The lower end of the actuator 185 as viewed in FIGS. 22 to 23 has a bevel on both the forward and rear sides with respect to the button of the staple-fire-ready switch 614 and the distance between the portion on the two bevels that actuates the button (or, only the flat portion thereof) corresponds to the acceptable staple forming range (i.e., safe firing length) of the staples in the staple cartridge 50. Thus, when the button of the staple-fire-ready switch 614 is depressed for the first time, the distance between the anvil 60 and the staple cartridge 50 is at the longest range for successfully firing and closing the staples. While the button is depressed, the separation distance 62 of the anvil 60 (see FIG. 18) remains within a safe staple-firing range. However, when the button of the staple-fire-ready switch 614 is no longer depressed—because the actuator 185 is positioned proximally of the button, then staples will not fire because the distance is too short for therapeutic stapling. FIG. 23 show the rod 180 in the proximal-most position, which is indicated by the top end of the actuator 185 closing the lever of a rod fully-retracted switch 616. When this switch 616 is actuated, the programming in the circuit board 500 prevents the motor 120 from turning in a rod-retraction direction; in other words, it is a stop switch for retracting the rod 180 in the proximal direction.

It is noted that FIGS. 2 to 3, 11 to 12, and 16 illustrate the distal end of the rod 180 not being connected to another device at its distal end (which would then contact the proximal end of the force switch 400). The connection band or bands between the distal end of the rod 180 and the proximal end of the force switch 400 are not shown in the drawings only for clarity purposes. In an exemplary embodiment, the pull-bands are flat and flexible to traverse the curved underside of the cartridge plunger 320 through the anvil neck 30 and up to the proximal end of the force switch 400. Of course, if the force switch 400 is not present, the bands would be connected to the proximal end of the trocar tip 410 that releasably connects to the proximal end of the anvil 60.

Figure 24:
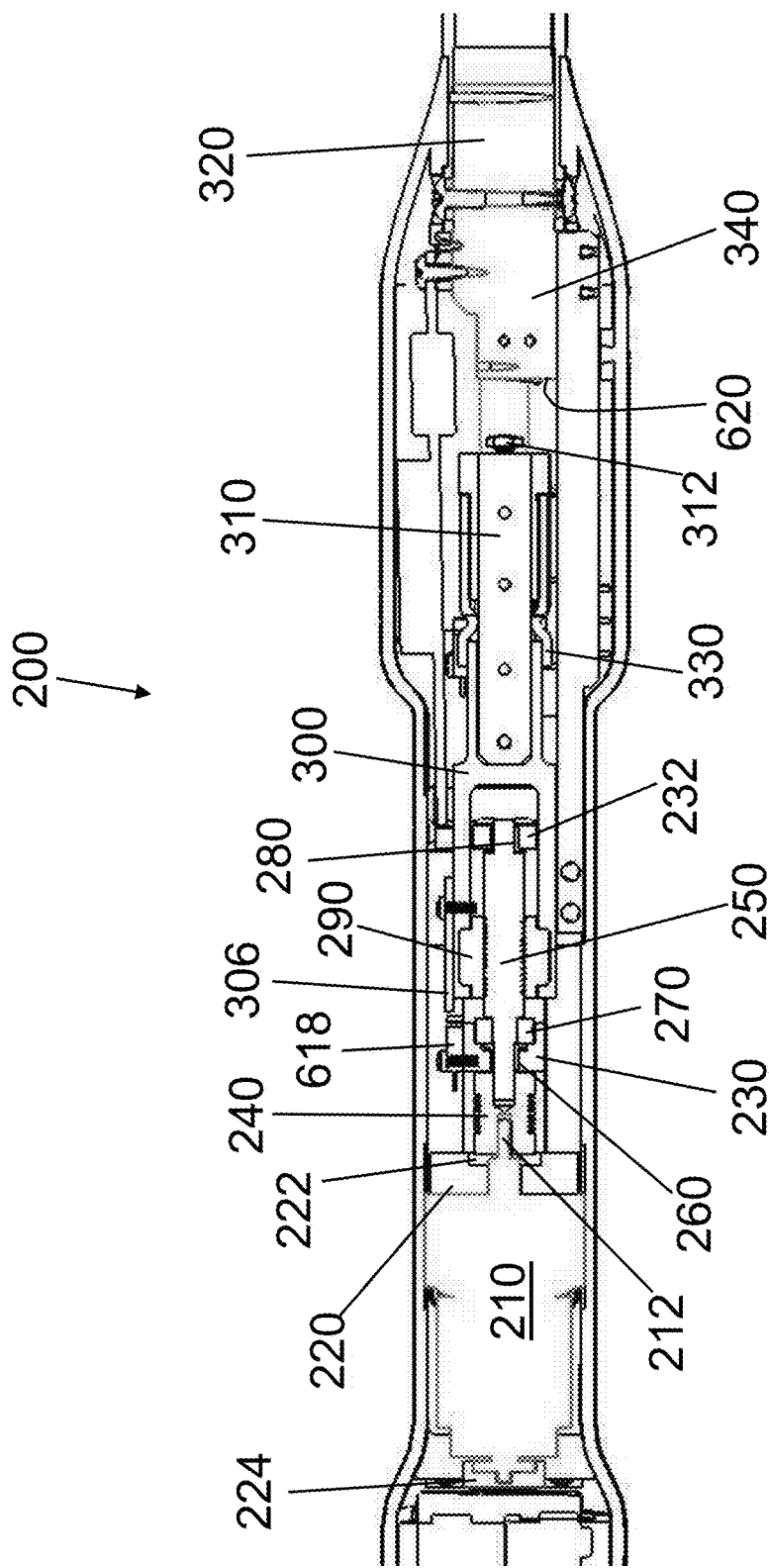
FIG. 24 is a fragmentary, horizontally cross-sectional view of the firing control assembly from above the handle body portion of the stapler of FIG. 1.
Figure 25:
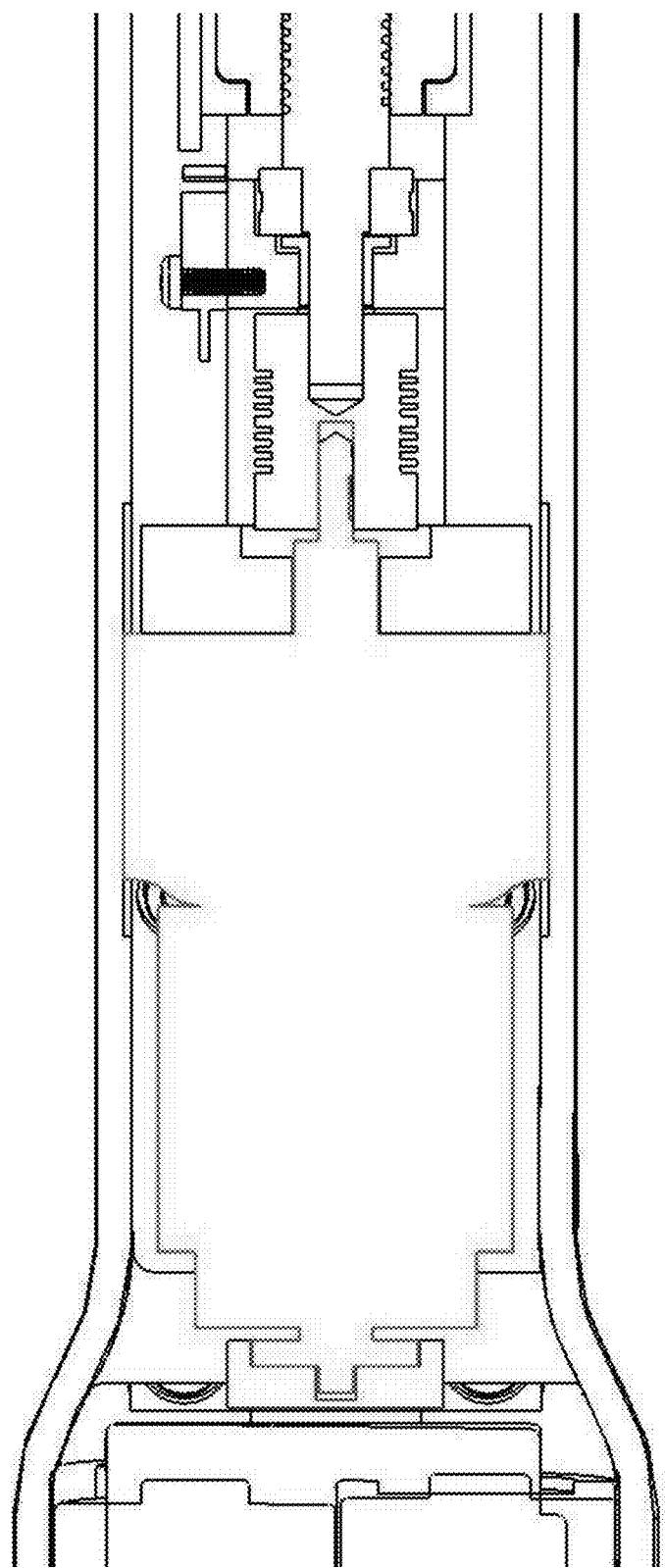
FIG. 25 is a fragmentary, enlarged, horizontally cross-sectional view from above a proximal portion of the firing control assembly of FIG. 24.
Figure 26:
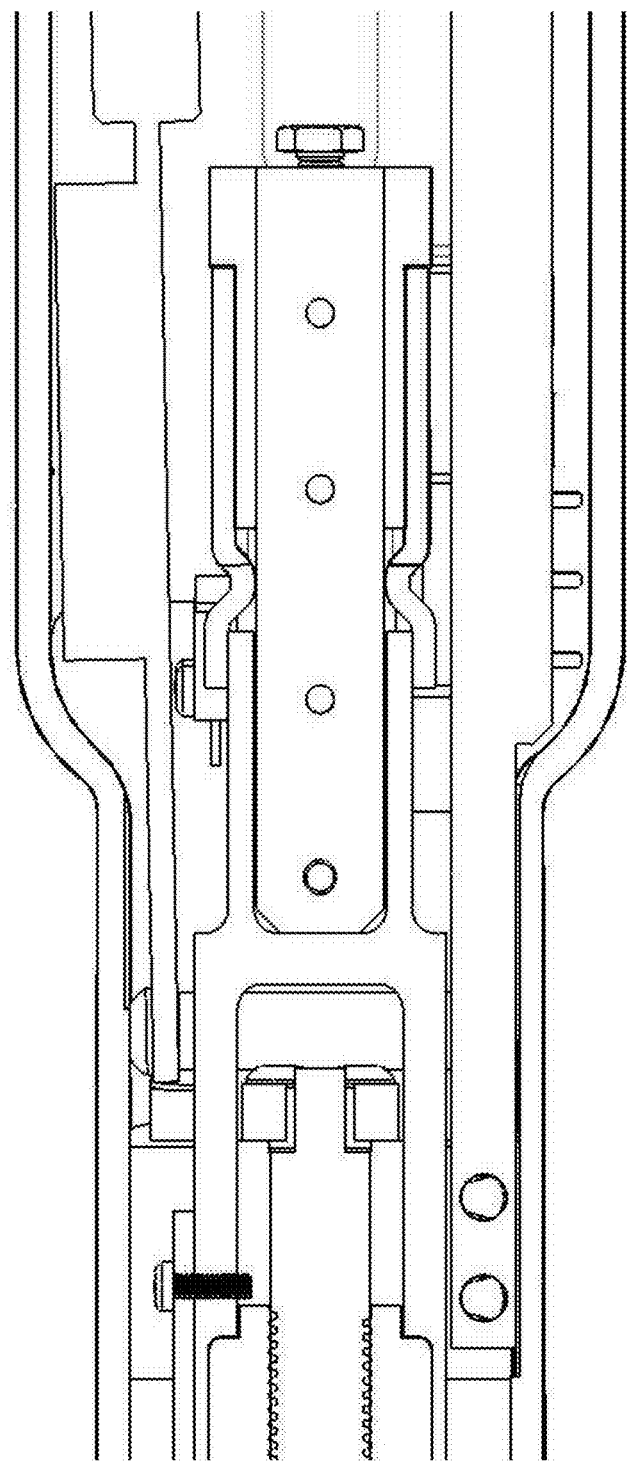
FIG. 26 is a fragmentary, enlarged, horizontally cross-sectional view from above an intermediate portion of the firing control assembly of FIG. 24.
Figure 27:
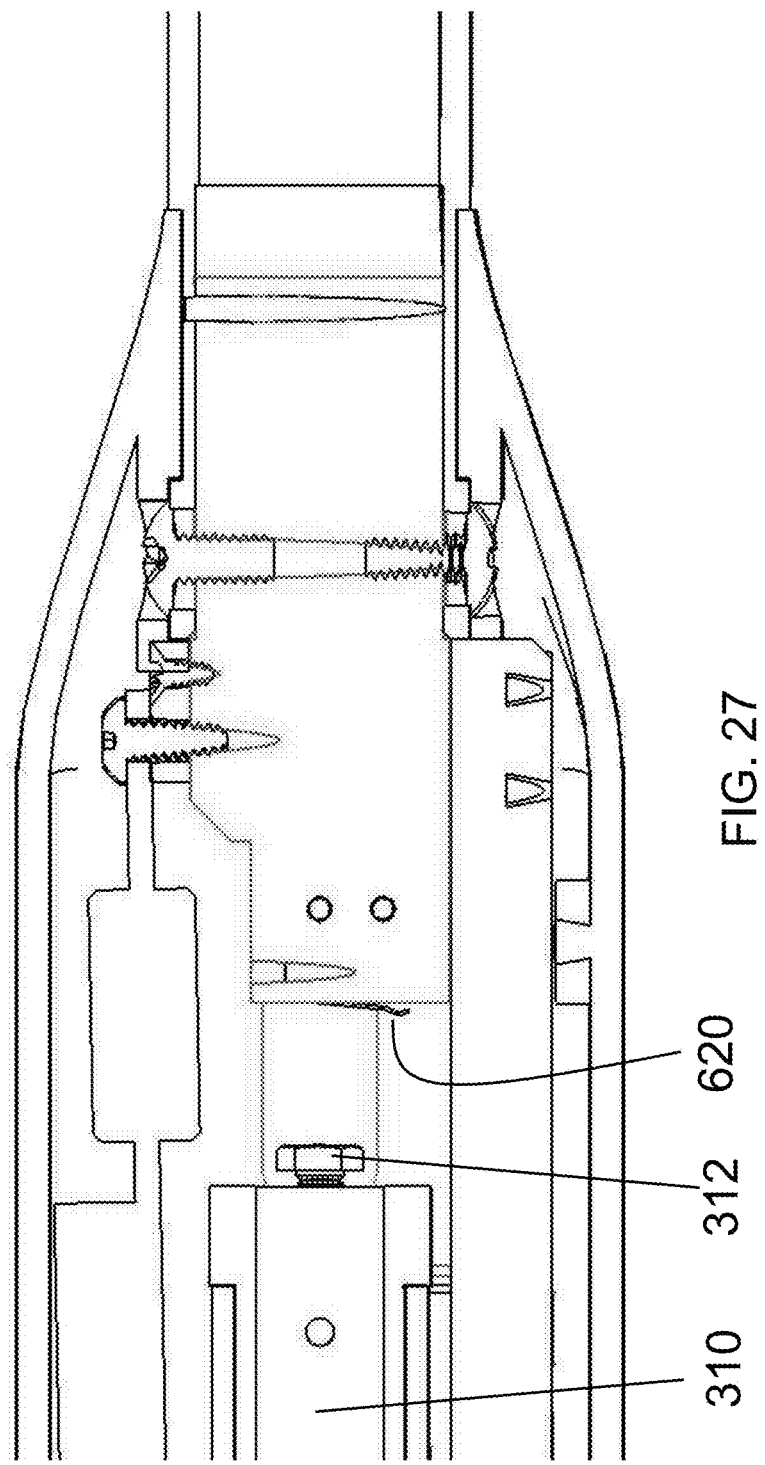
FIG. 27 is a fragmentary, enlarged, horizontally cross-sectional view from above a distal portion of the firing control assembly of FIG. 24.

Functionality of the staple control assembly 200 is described with regard to FIGS. 12 to 16 and 24 to 27, in particular, to FIG. 24. The stapling motor 210 is held between a motor bearing 222 and a motor shaft cover 224. The axle 212 of the stapling motor 210 is rotationally connected to the proximal end of the flexible coupling 240 and the distal end of the flexible coupling 240 is rotationally connected to the proximal end of the screw 250, which rotates on bearings 260, 270, 280 that are disposed within the intermediate coupling mount 230 and the distal plate 232. The longitudinally translating nut 290 is threaded onto the screw 250 between the coupling mount 230 and the distal plate 232. Therefore, rotation of the axle 212 translates into a corresponding rotation of the screw 250.

The nut coupling bracket 300 is longitudinally fixed to the nut 290 and to the stiffening rod 310 and the firing bracket 330. The firing bracket 330 is longitudinally fixed to the cartridge plunger 320, which extends (through a non-illustrated staple driver) up to the staple cartridge 50 (or to the staples). With such a connection, longitudinal movement of the nut 290 translates into a corresponding longitudinal movement of the cartridge plunger 320. Accordingly, when the staple firing switch 22 is activated, the stapling motor 210 is caused to rotate a sufficient number of times so that the staples are completely fired from the staple cartridge 50 (and the cutting blade, if present, is extended to completely cut the tissue between the anvil 60 and the staple cartridge 50). Programming in the circuitry, as described below, then causes the cartridge plunger 320 to retract after firing and remove any portion of the staple firing parts and/or the blade within the staple cartridge 50 from the anvil-cartridge gap 62.

Control of this stapling movement, again, occurs through micro-switches connected to the circuit board 500 through electrical connections, such as wires. A first of these control switches, the proximal staple switch 618, controls retraction of the staple control assembly 200 and defines the proximal-most position of this assembly 200. To actuate this switch, an actuation plate 306 is attached, in an adjustable manner, to a side of the nut coupling bracket 300. See, e.g., FIGS. 6 and 24. As such, when the nut 290 moves proximally to cause the plate 306 on the nut coupling bracket 300 to activate the proximal staple switch 618, power to the stapling motor 210 is removed to stop further proximally directed movement of the staple control assembly 200.

A second of the switches for controlling movement of the staple control assembly 200 is located opposite a distal transverse surface of the stiffening rod 310. See, e.g. FIG. 27. At this surface is disposed a longitudinally adjustable cam member 312 that contacts a distal staple switch 620. In an exemplary embodiment, the cam member 312 is a screw that is threaded into a distal bore of the stiffening rod 310. Accordingly, when the nut 290 moves distally to cause the cam member 312 of the stiffening rod 310 to activate the distal staple switch 620, power to the stapling motor 210 is removed to stop further distally directed movement of the staple control assembly 200.

Figure 28:
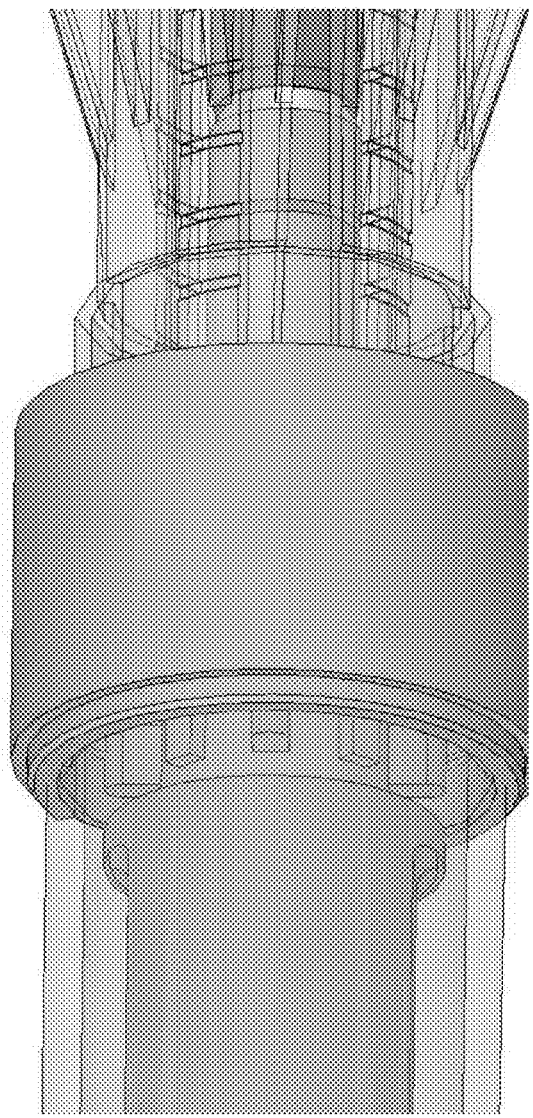
FIGS. 28 and 29 are shaded, fragmentary, enlarged, partially transparent perspective views of a staple cartridge removal assembly of the stapler of FIG. 1.
Figure 29:
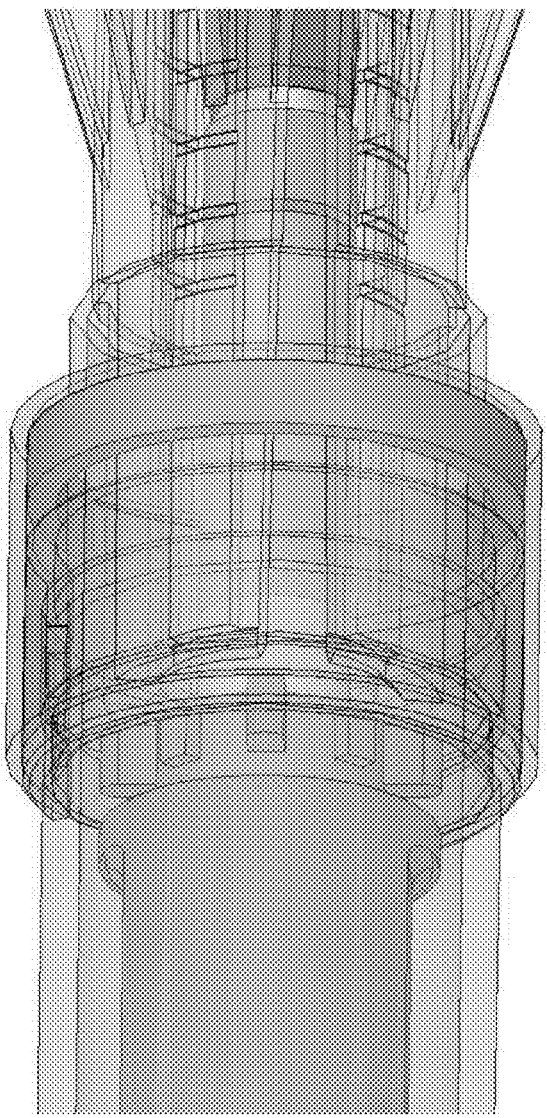

FIGS. 28 and 29 illustrate a removable connection assembly to permit replacement of a different staple cartridge 60 on the distal end of the anvil 30.

The proximal-most chamber of the handle body 10 defines a cavity for holding therein a power supply 600. This power supply 600 is connected through the circuit board 500 to the motors 120, 210 and to the other electrical components of the stapler 1.

The electronic components of the stapler 1 have been described in general with respect to control through the circuit board 500. The electric stapler 1 includes, as set forth above in an exemplary embodiment, two drive motors 120, 210 powered by batteries and controlled through pushbuttons 20, 21, 22. The ranges of travel of each motor 120, 210 are controlled by limit switches 610, 616, 618, 620 at the ends of travel and at intermediary locations 612, 614 along the travel. The logic by which the motors 120, 210 are controlled can be accomplished in several ways. For example, relay, or ladder logic, can be used to define the control algorithm for the motors 120, 210 and switches 610, 612, 614, 616, 618, 620. Such a configuration is a simple but limited control method. A more flexible method employs a microprocessor-based control system that senses switch inputs, locks switches out, activates indicator lights, records data, provides audible feedback, drives a visual display, queries radio frequency identification devices (RFIDs), senses forces, communicates with external devices, monitors battery life, etc. The microprocessor can be part of an integrated circuit constructed specifically for the purpose of interfacing with and controlling complex electro-mechanical systems. Examples of such chips include those offered by Atmel, such as the Mega 128, and by PIC, such as the PIC 16F684.

A software program is required to provide control instructions to such a processor. Once fully developed, the program can be written to the processor and stored indefinitely. Such a system makes changes to the control algorithm relatively simple; changes to the software that are uploaded to the processor adjust the control and user interface without changing the wiring or mechanical layout of the device.

For a disposable device, a power-on event is a one time occurrence. In this case, the power-on can be accomplished by pulling a tab or a release that is permanently removed from the device. The removal enables battery contact, thus powering on the device.

In any embodiment of the device, when the device is powered on, the control program begins to execute and, prior to enabling the device for use, goes through a routine that ensures awareness of actual positions of the extend/retract and firing sub-assemblies, referred to as a homing routine. The homing routine may be executed at the manufacturer prior to shipping to the user. In such a case, the homing routine is performed, the positions of the assemblies are set, and the device is shipped to the user in a ready-to-use condition. Upon power-up, the device verifies its positions and is ready to use.

Visual indicators (e.g., LEDs) are used to provide feedback to the user. In the case of the pushbutton switches 20, 21, 22, they can be lit (or backlit) when active and unlit when not active. The indicators can blink to convey additional information to the user. In the case of a delayed response after a button press, a given light can blink at an ever-increasing rate as the response becomes imminent, for example. The indicators can also light with different colors to indicate various states.

Cams are used in various locations at the stapler 1 to activate limit switches that provide position information to the processor. By using linear cams of various lengths, position ranges can be set. Alternatively, encoders can be used instead of limit switches (absolute and incremental positioning). Limit switches are binary: off or on. Instead of binary input for position information, encoders (such as optical encoders) can be used to provide position information. Another way to provide position feedback includes mounting pulse generators on the end of the motors that drive the sub-assemblies. By counting pulses, and by knowing the ratio of motor turns to linear travel, absolute position can be derived.

Use of a processor creates the ability to store data. For example, vital, pre-loaded information, such as the device serial number and software revision can be stored. Memory can also be used to record data while the stapler 1 is in use. Every button press, every limit switch transition, every aborted fire, every completed fire, etc., can be stored for later retrieval and diagnosis. Data can be retrieved through a programming port or wirelessly. In an exemplary embodiment, the device can be put into diagnostic mode through a series of button presses. In this diagnostic mode, a technician can query the stapler 1 for certain data or to transmit/output certain data. Response from the stapler 1 to such a query can be in the form of blinking LEDs, or, in the case of a device with a display, visual character data, or can be electronic data. As set forth above, a strain gauge can be used for analog output and to provide an acceptable strain band. Alternatively, addition of a second spring and support components can set this band mechanically.

An exemplary control algorithm for a single fire stapler 1 can include the following steps:

Power on.

Verify home position and go to home position, if necessary/desired.

Enable extend/retract buttons (lit) and disable (unlit) staple fire button.

Enable staple fire button only after full extension (anvil removal) and subsequent retraction with extend/retract buttons remaining enabled.

Upon actuation of staple fire button, retract anvil until force switch is activated.

Begin countdown by blinking fire button LED and increase blink rate as firing cycle becomes imminent. Continue monitoring of force switch and retract anvil so that force switch remains activated.

During staple fire cycle, any button press aborts staple fire routine.

If abort occurs before staple firing motor is activated, firing cycle stops, anvil is extended to home position, and staple fire button remains active and ready for a re-fire.

Alternatively, if the abort occurs during movement of firing motor, firing cycle stops, firing motor is retracted, anvil is returned to home position, and firing button is rendered inactive. Accordingly, stapler (or that staple cartridge) cannot be used.

After countdown to fire is complete, staple range limit switch is queried for position. If staple range limit switch is activated—meaning that anvil is within an acceptable staple firing range—then staple firing motor is activated and firing cycle proceeds. If staple range limit switch is not activated, then firing cycle is aborted, anvil is returned to home position, and staple firing button remains active ready for a re-fire attempt.

After a completed staple firing, anvil remains in closed position and only the extend button remains active. Once anvil is extended to at least the home position, both extend and retract buttons are made active. Staple fire button remains inactive after a completed staple firing.

Throughout the above exemplary cycle, button presses, switch positions, aborts, and/or fires can be recorded.

In a surgical procedure, the stapler is a one-way device. In the test mode, however, the test user needs to have the ability to move the trocar 410 and anvil 60 back and forth as desired. The power-on feature permits entry by the user into a manual mode for testing purposes. This test mode can be disengaged and the stapler reset to the use mode for packaging and shipment.

For packaging, it is desirable (but not necessary) to have the anvil 60 be disposed at a distance from the staple cartridge 50. Therefore, a homing sequence can be programmed to place the anvil 60 one centimeter (for example) away from the staple cartridge 50 before powering down for packaging and shipment.

When the electric stapler is unpackaged and ready to be used for surgery, the user turns the stapler on (switch 12). Staples should not be allowed to fire at any time prior to being in a proper staple-firing position and a desired tissue compression state. Thus, the anvil/trocar extend/retract function is the only function that is enabled. In this state, the extend and retract buttons 20, 21 are lit and the staple firing switch 22 is not lit (i.e., disabled).

Before use inside the patient, the trocar 410 is extended and the anvil 60 is removed. If the stapler is being used to anastomose a colon, for example, the trocar 410 is retracted back into the anvil neck 30 and the staple cartridge 50 and anvil neck 30 are inserted trans-anally into the colon to a downstream side of the dissection. The anvil 60, in contrast, is inserted through an upstream laparoscopic incision and placed at the upstream side of the dissection. The anvil 60 is attached to the trocar 410 and the two parts are retracted towards the staple cartridge 50 until a staple ready condition occurs. As set forth above, the anvil is moved to a distance that does not substantially compress and, specifically, does not desiccate, the tissue therebetween. At this point, staple firing can occur when desired.

The staple firing sequence is started by activating the staple fire switch 22. Staple firing can be aborted anytime during the firing sequence, whether prior to movement (during the blanching cycle) or during movement (whether the staples have started to form or not). The software is programmed to begin a staple firing countdown sequence because it is understood that the tissue needs to be compressed and allowed to desiccate before staple firing should occur. Thus, after the staple firing switch 22 is activated, the anvil 60 closes upon the interposed tissue and begins to compress the tissue. The staple firing sequence includes an optimal tissue compression (OTC) measurement and a feedback control mechanism that causes staples to be fired only when the compression is in a desired pressure range, referred to as the OTC range, and a sufficient time period has elapsed to allow fluid removal from the compressed tissue. The OTC range is known beforehand based upon known characteristics of the tissue that is to be compressed between the anvil 60 and the staple cartridge 50 (the force switch can be tuned for different tissue OTC ranges). It is the force switch 400 that provides the OTC measurement and supplies the microprocessor with information indicating that the OTC for that particular tissue has been reached. The OTC state can be indicated to the user with an LED, for example.

When the firing sequence begins, the staple fire switch 22 can be made to blink at a given rate and then proceed to blink faster and faster, for example, until firing occurs. If no abort is triggered during this wait time, the OTC state will remain for the preprogrammed desiccation duration and staple filing will occur after the countdown concludes. In the example of colon anastomosis with a circular stapler, stapling of the dissection occurs simultaneously with a cutting of tissue at the center of the dissection. This cutting guarantees a clear opening in the middle of the circular ring of staples sufficient to create an opening for normal colon behavior after the surgery is concluded.

As the liquid from the interposed compressed tissue is removed, the compressive force on the tissue naturally reduces. In some instances, this reduction can be outside the OTC range. Therefore, the program includes closed-loop anvil-compression control that is dependent upon continuous measurements provided by the force switch 400. With this feedback, the compressed tissue is kept within the OTC range throughout the procedure and even after being desiccated.

During the staple firing cycle, any actuation of a control switch by the user can be programmed to abort the staple fire routine. If an abort occurs before the staple firing motor 210 is activated, the firing cycle stops, the anvil 60 is extended to a home position, and the staple fire switch 22 remains active and ready for a re-fire attempt, if desired. Alternatively, if the abort occurs during movement of the staple firing motor 210, the firing cycle stops and the staple firing motor 210 is caused to extend the anvil 60 to its home position. At this point, the staple firing switch 22 is rendered inactive. Accordingly, the stapler (or that particular staple cartridge) can no longer be used (unless the staple cartridge is replaced).

It is noted that before a staple firing can occur, a staple range limit switch is queried for relative position of the staple cartridge 50 and anvil 60. If the staple range limit switch is activated—meaning that anvil 60 is within an acceptable staple firing range—then the staple firing motor 210 can be made active and the firing cycle can be allowed to proceed. If the staple range limit switch is not activated, then the firing cycle is aborted, the anvil 60 is returned to the home position, and the staple firing switch 22 remains active and ready for a re-fire attempt.

Powering (also referred to as actuating, powering, controlling, or activating) of the motor and/or the drive train of any portion of the end effector (e.g., anvil or stapler/cutter) is described herein. It is to be understood that such powering need not be limited to a single press of an actuation button by the user nor is the powering of a motor limited to a single energizing of the motor by the power supply. Control of any motor in the device can require the user to press an actuation button a number of times, for example, a first time to actuate a portion of the end effector for a first third of movement, a second time for a second third of movement, and a third time for a last third of movement. More specifically for a surgical stapler, a first exemplary actuation can move the staple sled or blade past the lock-out, a second exemplary actuation can move the part up to the tissue, and a third exemplary actuation can move the sled past all staples to the end of the staple cartridge. Similarly, powering of a motor need not be constant, for example, where the motor is energized constantly from the time that the blade begins movement until it reaches the end point of its movement. Instead, the motor can be operated in a pulsed mode, a first example of which includes periodically switching on and off the power supplied by the power supply to the motor during actuation of an end effector function. More specifically for a stapler, the motor can be pulsed ten times/second as the staple/cutter moves from its proximal/start position to its distal-most position. This pulsing can be directly controlled or controlled by microprocessor, either of which can have an adjustable pulse rate. Alternatively, or additionally, the motor can be operated with a pulse modulation (pulse-width or pulse-frequency), with pulses occurring at very short time periods (e.g., tenths, hundredths, thousandths, or millionths of a second). Accordingly, when the power supply, the motor, and/or the drive train are described herein as being powered, any of these and other possible modes of operation are envisioned and included.

After a completed staple firing, the anvil 60 remains in the closed position and only the extend switch 20 remains active (all other switches are deactivated). Once the anvil 60 is extended to at least the home position, both the extend and retract switches 20, 21 are made active but the retraction switch 21 does not permit closure of the anvil 60 past the home position. The staple fire switch 22 remains inactive after a completed staple firing.

As set forth above, the anvil neck 30 houses a linear force switch 400 connected to the trocar 410. This switch 400 is calibrated to activate when a given tensile load is applied. The given load is set to correspond to a desired pressure that is to be applied to the particular tissue before stapling can occur. Interfacing this switch 400 with the processor can ensure that the firing of staples only occurs within the OTC range.

An exemplary embodiment of a program listing for carrying out the methods described herein is supplied in the Appendix. The program listing provided in the Appendix is only submitted as exemplary and those of skill in the art can appreciate that programming the methods can take many different forms to achieve the same functionality.

Also mentioned above is the possibility of using RFIDs with a staple cartridge and a RFID interface for sensing compatible staple cartridges. In the case of a stapler that uses re-loadable staple cartridges, such as the stapler 1 described herein, a RFID can be placed in the staple cartridge to ensure compatibility with the particular stapler and, also, to track usage and inventory. In such a configuration, the stapler includes a RFID reader that interrogates the RFID mounted in the cartridge. The RFID responds with a unique code that the stapler verifies. If the stapler cartridge is verified, the stapler becomes active and ready for use. If the cartridge is rejected, however, the stapler gives a rejected indication (e.g., a blinking LED, an audible cue, a visual indicator). To avoid accidental or improper reading of a nearby staple cartridge, the antenna of the RFID reader can be constructed to only read the RFID when the staple cartridge is installed in the stapler or is very nearby (optimally, at the distal end of the device). Use of the RFID can be combined with a mechanical lockout to ensure that only one fire cycle is allowed per staple cartridge.

In the unlikely event that the stapler becomes inoperable during use, a mechanical override or bail-out is provided to allow manual removal of the device from the patient.

As described above, the present invention is not limited to a circular stapler, which has been used as an exemplary embodiment above, and can be applied to any surgical stapling head, such as a linear stapling device, for example. Accordingly, a linear stapler is being used in the text that follows for various exemplary embodiment. However, use of a linear stapler in this context should not be considered as limited only thereto.

Described above are components that exist along the staple control axis 80 and that form the staple control assembly 200. As set forth therein, the required force for proper staple ejection and tissue cutting can be over 200 pounds and, possibly, up to 250 pounds. It has been determined that minimum requirements for carrying out the desired stapling and cutting functions with the electric surgical stapler for human tissue (such as colon tissue, for example) are:

1) delivering approximately 54.5 kg (120 pounds) of force over a stroke of about 60 mm (~2.4") in approximately 3 seconds; or
2) delivering approximately 82 kg (180 pounds) of force over a stroke of about 60 mm (~2.4") in approximately 8 seconds.

The electric-powered, hand-held surgical stapling device of the present invention can meet these requirements because it is optimized in a novel way as set forth below.

To generate the force necessary to meet the above-mentioned requirements, the maximum power (in watts) of the mechanical assembly needs to be calculated based upon the maximum limits of these requirements: 82 kg over 60 mm in 3 seconds. Mathematical conversion of these figures generates an approximate maximum of 16 Watts of mechanical power needed at the output of the drive train. Conversion of the electrical power into mechanical power is not 1:1 because the motor has less than 100% efficiency and because the drive train also has less than 100% efficiency. The product of these two efficiency ratings forms the overall efficiency. The electrical power required to produce the 16 Watts of mechanical power is greater than the 16 Watts by an inverse product of the overall efficiency. Once the required electrical power can be determined, an examination of available power supplies can be made to meet the minimum power requirements. Thereafter, an examination and optimization of the different power supplies can be made. This analysis is described in detail in the following text.

Matching or optimizing the power source and the motor involves looking into the individual characteristics of both. When examining the characteristics of an electric motor, larger motors can perform a given amount work with greater efficiency than smaller motors. Also motors with rare-earth magnets or with coreless construction can deliver the same power in a smaller size, but at higher cost. Further, in general, larger motors cost less than smaller motors if both are designed to deliver the same power over a given period of time. Larger motors, however, have an undesirable characteristic when used in surgical stapling devices because the handle in which they are to be placed is limited by the size of an operator's hand. Physicians desire to use devices that are smaller and lighter, not larger and heavier. Based upon these considerations, cost, size, and weight are factors that can be optimized for use in the surgical stapler handle of the present invention.

Available motors for use within a physician's hand include motors with relatively inexpensive ceramic magnets and motors with relatively expensive rare earth (i.e., neodymium) magnets. However, the power increase of the latter as compared to the former is not sufficiently large to warrant the substantial increase in cost of the latter. Thus, ceramic magnet motors can be selected for use in the handle. Exemplary motors come in standard sizes (diameter) of 27.5 mm or 24 mm, for example. These motors have a rated efficiency of approximately 60% (which decreases to 30% or below depending upon the size of the load). Such motors operate at speeds of approximately 30,000 rpm (between 20,000 and 40,000 rpm) when unloaded.

Even though such conventional motors could be used, it would be desirable to reduce the size even further. To that effect, the inventors have discovered that coreless, brush-type, DC motors produce similar power output but with a significant reduction in size. For example, a 17 mm diameter coreless motor can output approximately the same power as a standard 24 mm diameter motor. Unlike a standard motor, the coreless motor can have an efficiency of up to 80%. Coreless motors almost all use rare earth magnets.

With such a limited volume and mechanical power available, it is desirable to select a mechanical gear train having the greatest efficiency. Placing a rack and pinion assembly as the final drive train control stage places a high-efficiency end stage in the drive train as compared to a screw drive because, in general, the rack and pinion has an approximate 95% efficiency, and the screw drive has a maximum of about 80% efficiency. For the linear electric stapler, there is a 60 mm travel range for the stapling/cutting mechanism when the stapler has a 60 mm cartridge (cartridges ranging from 30 mm to 100 mm can be used but 60 mm is used in this example for illustrative purposes). With this travel range, a 3-second, full travel duration places the rack and pinion extension rate at 0.8 inches per second. To accomplish this with a reasonably sized rack and pinion assembly, a gear train should reduce the motor output to approximately 60 rpm. With a motor output speed of approximately 30,000 rpm, the reduction in speed for the drive train becomes approximately 500:1. To achieve this reduction with the motor, a 5-stage drive train is selected. It is known that such drive trains have an approximate 97% efficiency for each stage. Thus, combined with an approximate 95% efficiency of the rack and pinion, the overall efficiency of the drive train is $(0.95)(0.97)^5$ or 82%. Combining the 60% motor efficiency with the 82% drive train efficiency yields an overall electrical to final mechanical efficiency of approximately 49.2%. Knowing this overall efficiency rating, when determining the amount of electrical power required for operating the stapler within the desired requirements, the actual electrical power needed is almost twice the value that is calculated for producing the stapling/cutting force.

To generate the force necessary to meet the above-mentioned requirements, the power (in watts) of the mechanical assembly can be calculated based upon the 82 kg over 60 mm in 3 seconds to be approximately 16 Watts. It is known that the overall mechanical efficiency is 49.2%, so 32.5 Watts is needed from the power supply (16 mech. watts≈32.5 elec. Watts×0.492 overall efficiency.). With this minimum requirement for electrical power, the kind of cells available to power the stapler can be identified, which, in this case, include high-power Lithium Primary cells. A known characteristic of high-power Lithium cells (e.g., CR123 or CR2 cells) is that they produce about 5 peak watts of power per cell. Thus, at least six cells in series will generate the required approximate amount of 32.5 watts of electrical power, which translates into 16 watts of mechanical power. This does not end the optimization process because each type of high-power Lithium cell manufactured has different characteristics for delivering peak power and these characteristics differ for the load that is to be applied.

Various battery characteristics exist that differentiate one battery of a first manufacturer from another battery of a second manufacturer. Significant battery characteristics to compare are those that limit the power that can be obtained from a battery, a few of which include:
- type of electrolyte in the cell;
- electrolyte concentration and chemistry;
- how the anode and cathode are manufactured (both in chemistry and in mechanical construction); and
- type and construction of the PTC (positive temperature coefficient of resistance) device.

Testing of one or more of these characteristics gives valuable information in the selection of the most desirable battery for use in the stapling device. It has been found that an examination of the last characteristic—PTC device behavior—allows an optimization of the type of battery to perform the desired work.

Most power sources are required to perform, with relative certainty and efficiency, many times throughout a long period of time. When designing and constructing a power source, it is not typical to select the power source for short-duration use combined with a low number of uses. However, the power source of an electric stapling device is only used for a short duration and for a small number of times. In each use, the motor needs to be ready for a peak load and needs to perform without error. This means that, for surgical staplers, the stapling/cutting feature will be carried out during only one medical procedure, which has cycle counts of between 10 and 20 uses at most, with each use needing to address a possible peak load of the device. After the one procedure, the device is taken out of commission and discarded. Therefore, the power source for the present invention needs to be constructed unlike any other traditional power supply.

The device according to the present invention is constructed to have a limited useful life of a power cell as compared to an expected useful life of the power cell when not used in the device. When so configured, the device is intended to work few times after this defined "life span." It is known that self-contained power supplies, such as batteries, have the ability to recover after some kind of use. For optimization with the present invention, the device is constructed within certain parameters that, for a defined procedure, will perform accordingly but will be limited or unable to continue performance if the time of use extends past the procedure. Even though the device might recover and possibly be used again in a different procedure, the device is designed to use the power cells such that they will most likely not be able to perform at the enhanced level much outside the range of intended single use periods or outside the range of aggregate use time. With this in mind, a useful life or clinical life of the power supply or of the device is defined, which life can also be described as an intended use. It is understood that this useful/clinical life does not include periods or occurrences of use during a testing period thereof to make sure that the device works as intended. The life also does not include other times that the device is activated outside the intended procedure, i.e., when it is not activated in accordance with a surgical procedure.

Conventional batteries available in the market are designed to be used in two ways: (1) provide a significant amount of power for a short duration (such as in a high-drain digital device like cameras) or (2) provide a small amount of power over a long duration (such as a computer's clock backup). If either of these operations is not followed, then the battery begins to heat up. If left unchecked, the battery could heat to a point where the chemicals could cause significant damage, such as an explosion. As is apparent, battery explosion is to be avoided. These extremes are prevented in conventional batteries with the presence of the PTC device—a device that is constructed to limit conduction of the battery as the battery increases in temperature (i.e., a positive temperature coefficient of resistance). The PTC device protects batteries and/or circuits from overcurrent and overtemperature conditions. Significantly, the PTC device protects a battery from external short circuits while still allowing the battery to continue functioning after the short circuit is removed. Some batteries provide short-circuit and/or overtemperature protection using a one-time fuse. However, an accidental short-circuit of such a fused battery causes the fuse to open, rendering the battery useless. PTC-protected batteries have an advantage over fused batteries because they are able to automatically "reset" when the short circuit is removed, allowing the battery to resume its normal operation. Understanding characteristics of the PTC device is particularly important in the present invention because the motor will be drawing several times greater current than would ever be seen in a typical high-drain application.

The PTC device is provided in series with the anode and cathode and is made of a partially conducting layer sandwiched between two conductive layers, for example. The device is in a low-resistance condition at a temperature during a normal operation (depending on circuit conditions in which the device is used, for example, from room temperature to 40° C.). On exposure to high temperature due to, for example, unusually large current resulting from the formation of a short circuit or excessive discharge (depending on circuit conditions in which the device is used, for example, from 60° to 130° C.), the PTC device switches into an extremely high-resistance mode. Simply put, when a PTC device is included in a circuit and an abnormal current passes through the circuit, the device enters the higher temperature condition and, thereby, switches into the higher resistance condition to decrease the current passing through the circuit to a minimal level and, thus, protect electric elements of the circuit and the battery/ies. At the minimal level (e.g., about 20% of peak current), the battery can cool off to a "safe" level at which time greater power can be supplied. The partially conducting layer of the PTC device is, for example, a composite of carbon powder and polyolefin plastic. Further description of such devices is unnecessary, as these devices are described and are well known in the art.

Because PTC circuits of different manufacturers operate with different characteristic behaviors, the present invention takes advantage of this feature and provides a process for optimizing the selection of a particular battery to match a particular motor and a particular use. An examination of the time when the PTC device switches to the higher resistance condition can be used as this indicator for optimizing a particular motor and drive train to a battery. It is desirable to know when the PTC device makes this switch so that, during normal stapler use, the PTC device does not make this change.

Exemplary batteries were loaded with various levels from approximately 3 amps to approximately 8 amps. At the high end, the PTC device changed to the high-resistance state almost immediately, making this current level too high for standard CR123 cells. It was determined that, for between 4 and 6 amps, one manufacturer's cell had PTC activation sooner than another manufacturer's cell. The longest PTC changeover duration for the second manufacturer was >3 minutes for 4 amps, approximately 2 minutes for 5 amps, and almost 50 seconds for 6 amps. Each of these durations was significantly greater than the 8-second peak load requirement. Accordingly, it was determined that the second manufacturer's cells would be optimal for use at peak amps as compared to the first manufacturer's cells.

Initially, it was surmised that higher amperes with lower or constant voltage would generate higher power out of the power cell(s). Based upon the configuration of 6 cells in series, the peak voltage could be 18 volts with a peak current of only 6 amps. Placing cells in parallel, in theory, should allow a higher peak amperage and a 3×2 configuration (two parallel set of three cells in series) could have a 9 volt peak with up to a 12 amp peak.

Different single cells were investigated and it was confirmed that a relatively low voltage (about 1.5 to 2 volts) and approximately 4 to 6 amperes produces the highest power in Watts. Two six-cell configurations were examined: a 6×1 series connection and a 3×2 parallel connection. The 3×2 configuration produced the greatest peak amperes of approximately 10 amps. The 6×1 configuration produced about 6 amps peak and the single cell was able to peak at 5-6 amps before the PTC device changed state. This information indicated the state at which any single cell in the series group would be activating its PTC device and, thus, limiting current through the entire group of cells. Thus, the tentative conclusion of yielding peak amps at lower voltage with a 3×2 configuration was maintained.

Figure 30:
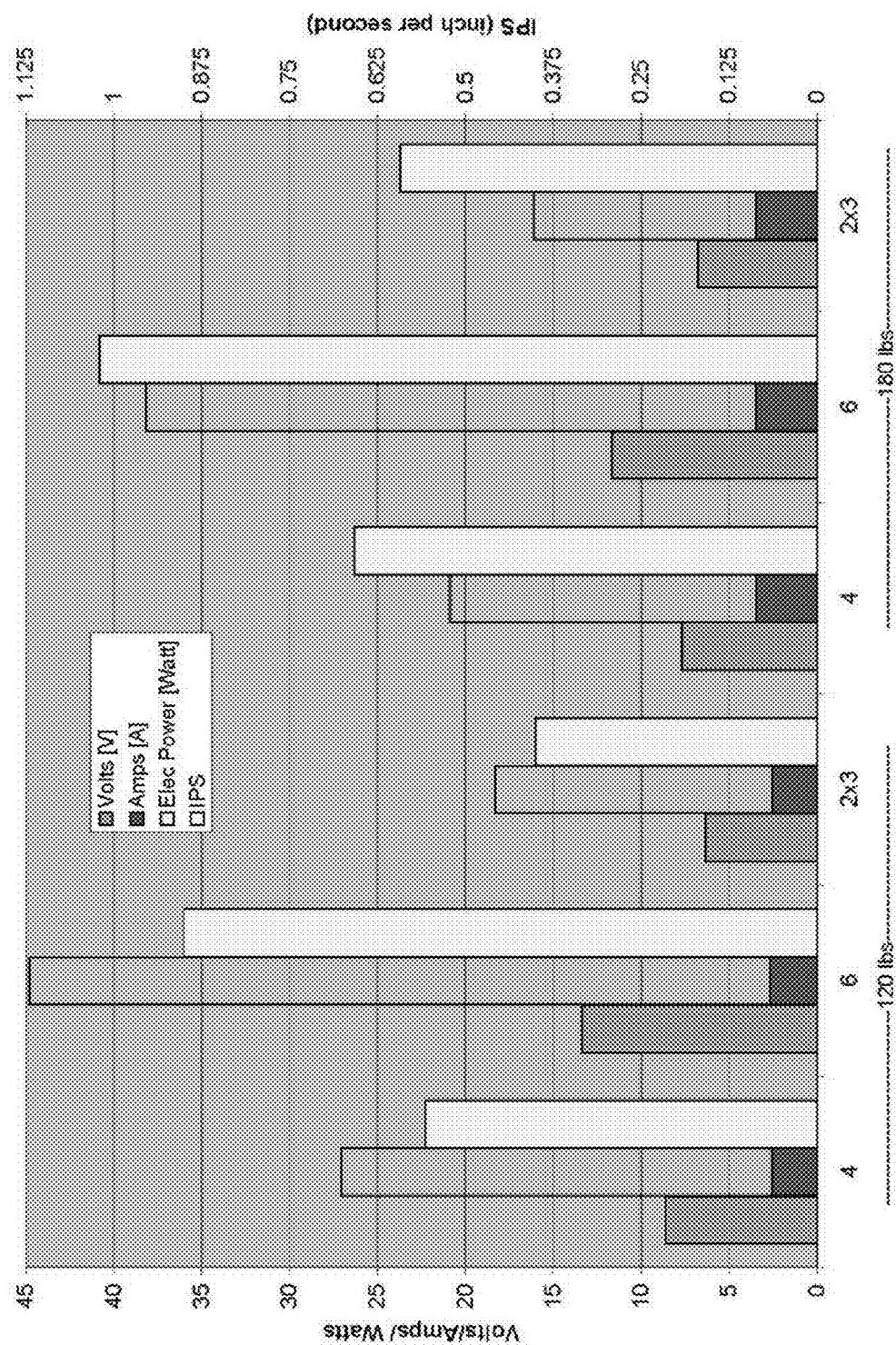
FIG. 30 is a bar graph illustrating a speed that a pinion moves a rack shown in FIG. 31 for various loads.

Three different CR123 battery configurations were tested: 4×1, 6×1, and 3×2, to see how fast the pinion would move the rack (in inches per second ("IPS")) for the 120# and 180# loads and for a given typical gearing. The results of this real world dynamic loading test are shown in the chart of FIG. 30, for both the 120# load:
 the 4×1 battery pack was able to move the load at about 0.6 IPS at approximately 2.5 amps but at approximately 8 volts;
 the 6×1 battery pack was able to move the load at about 0.9 IPS at approximately 2.5 amps but at approximately 13 volts; and
 the 3×2 battery pack was able to move the load at about 0.4 IPS at approximately 2.5 amps but at approximately 6 volts;
and the 180# load:
 the 4×1 battery pack was able to move the load at about 0.65 IPS at approximately 4 amps but at approximately 7.5 volts;
 the 6×1 battery pack was able to move the load at about 0.9 IPS at approximately 4 amps but at approximately 12 volts; and
 the 3×2 battery pack was able to move the load at about 0.4 IPS at approximately 4 amps but at approximately 7 volts.
Clearly, the peak current was limited and this limit was dependent upon the load. This experiment revealed that the motor drew a similar current regardless of the power supply for a given load but that the voltage changed depending upon the battery cell configuration. With respect to either load, the power output was the greatest in the 6×1 configuration and not in the 3×2 configuration, as was expected. From this, it was determined that the total power of the cell pack is driven by voltage and not by current and, therefore, the parallel configuration (3×2) was not the path to take in optimizing the power source.

Traditionally, when designing specifications for a motor, the windings of the motor are matched to the anticipated voltage at which the motor will be run. This matching takes into account the duration of individual cycles and the desired overall life of the product. In a case of an electric stapling device the motor will only be used for very short cycles and for a very short life, traditional matching methods yield results that are below optimal. Manufacturers of the motors give a voltage rating on a motor that corresponds to the number of turns of the windings. The lower the number of turns, the lower the rated voltage. Within a given size of motor winding, a lower number of turns allows larger wire to be used, such that a lower number of turns results in a lower resistance in the windings, and a higher number of turns results in a higher resistance. These characteristics limit the maximum current that the motor will draw, which is what creates most of the heat and damage when the motor is overdriven. For the present invention, a desirable configuration will have the lowest winding resistance to draw the most current from the power supply (i.e., battery pack). By running the motor at a voltage much higher than the motor rating, significantly greater power can be drawn from similarly sized motors. This trait was verified with testing of nearly identical coreless motors that only varied in winding resistance (and, hence, the number of turns). For example, 12-volt and 6-volt rated motors were run with 6 cells (i.e., at 19.2 volts). The motors rated for 12 volts output peak power of 4 Watts with the battery voltage only falling slightly to 18 volts when drawing 0.7 amps. In comparison, the motors rated for 6 volts output 15 Watts of power with the voltage dropping to 15 volts but drawing 2 amps of current. Therefore, the lower resistance windings were selected to draw enough power out of the batteries. It is noted that the motor windings should be balanced to the particular battery pack so that, in a stall condition, the motor does not draw current from the cells sufficient to activate the PTC, which condition would impermissibly delay use of an electric surgical stapler during an operation.

The 6×1 power cell configuration appeared to be more than sufficient to meet the requirements of the electric stapling device. Nonetheless, at this point, the power cell can be further optimized to determine if six cells are necessary to perform the required work. Four cells were, then, tested and it was determined that, under the 120# load, the motor/drive train could not move the rack over the 60 mm span within 3 seconds. Six cells were tested and it was determined that, under the 120# load, the motor/drive train could move the rack over the 60 mm span in 2.1 seconds—much faster than the 3-second requirement. It was further determined that, under the 180# load, the motor/drive train could move the rack over the 60 mm span in less than 2.5 seconds— much quicker than the 8-second requirement. At this point, it is desirable to optimize the power source and mechanical layout to make sure that there is no "runaway" stapling/ cutting; in other words, if the load is significantly less than the required 180# maximum, or even the 120# maximum, then it would not be desirable to have the rack move too fast.

Figure 31:
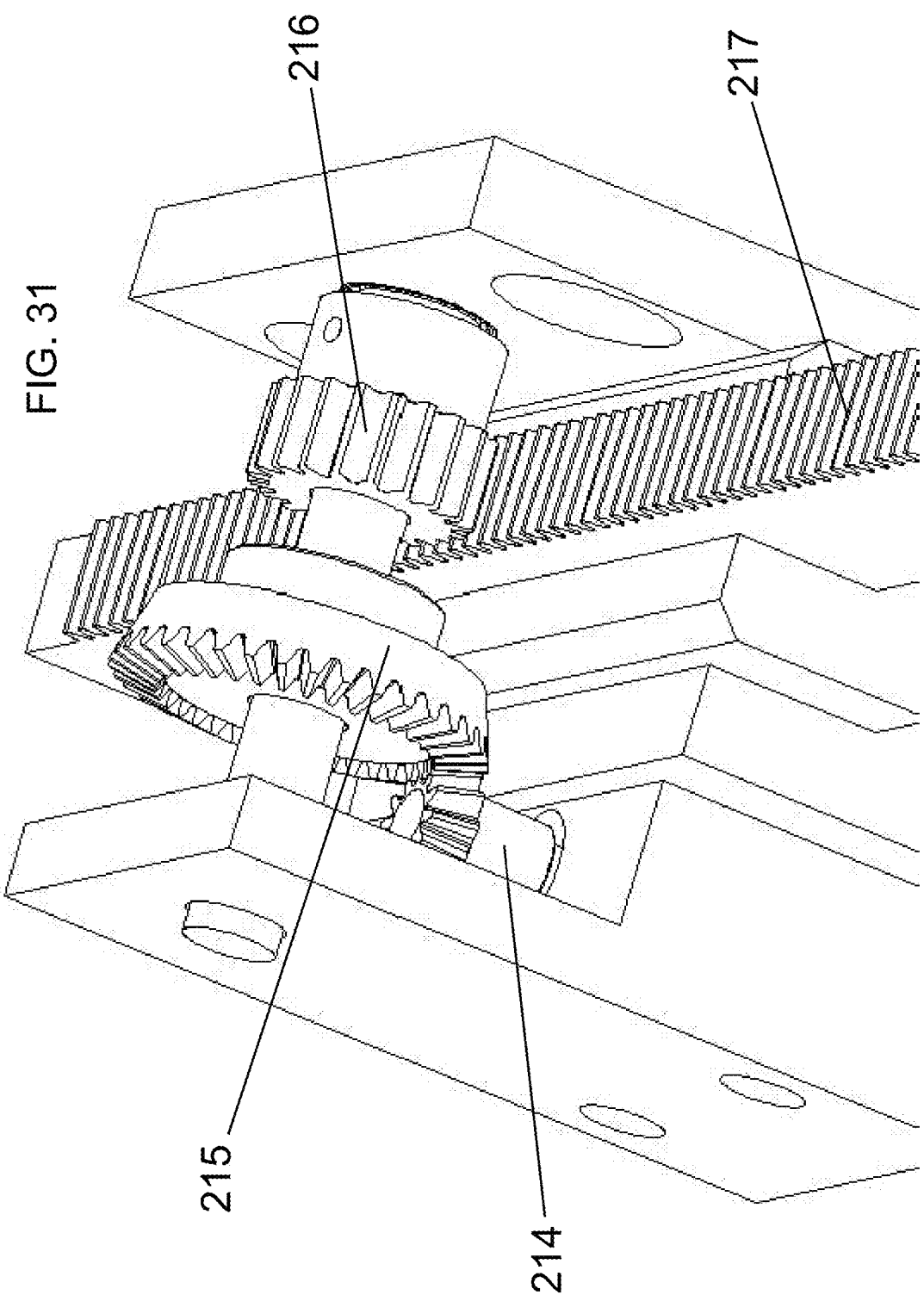
FIG. 31 is a fragmentary, perspective view of a simplified, exemplary portion of a gear train according to the present invention between a gear box and a rack.

The gear reduction ratio and the drive system need to be optimized to keep the motor near peak efficiency during the firing stroke. The desired stroke of 60 mm in 3 seconds means a minimum rack velocity of 20 mm/sec (~0.8 inches/ second). To reduce the number of variables in the optimization process, a basic reduction of 333:1 is set in the gear box. This leaves the final reduction to be performed by the gears present between the output shaft 214 of the gear box and the rack 217, which gears include, for example, a bevel gear 215 and the pinion 216 (which drives the rack), a simplified example of which is illustrated in FIG. 31.

These variables can be combined into the number of inches of rack travel with a single revolution of the output shaft 214 of the 333:1 gearbox. If the gearbox output (in rpm) never changed, it would be a simple function to match the inches of rack travel per output shaft revolution ("IPR") to the output rpm to get a desired velocity as follows:

(60 rpm 1 revolution/second (rps); 1 rps @ 0.8 IPR→0.8 in/sec).

In such an idealized case, if the IPR is plotted against velocity, a straight line would be produced. Velocity over a fixed distance can be further reduced to Firing Time. Thus, a plot of Firing Time versus IPR would also be a straight line in this idealized case. However, output of the motor (in rpm) and, therefore, of the gearbox, is not fixed because this speed varies with the load. The degree of load determines the amount of power the motor can put out. As the load increases, the rpms decrease and the efficiency changes. Based upon an examination of efficiency with differing loads, it has been determined that efficiency peaks at just over 60%. However, the corresponding voltage and amperes at this efficiency peak are not the same as at the point of peak power. Power continues to increase as the load increases until the efficiency is falling faster than the power is increasing. As the IPR increases, an increase in velocity is expected, but a corresponding increase in IPR lowers the mechanical advantage and, therefore, increases the load. This increasing load, with the corresponding decrease in efficiency at progressively higher loads, means that a point will exist when greater velocity out of the rack is no longer possible with greater IPR. This behavior is reflected as a deviation from a predicted straight line in the plot of Firing Time (in sec) versus IPR. Experimentation of the system of the present invention reveals that the boundary between unnecessary mechanical advantage and insufficient mechanical advantage occurs at approximately 0.4 IPR.

From this IPR value, it is possible to, now, select the final gear ratio of the bevel gear 215 to be approximately three times greater (3:1) than the sprocket of the output shaft. This ratio translates into an approximate IPR of 0.4.

Now that the bevel gear 215 has been optimized, the battery pack can be reexamined to determine if six cells could be reduced to five or even four cells, which would save cost and considerably decrease the volume needed for the power supply within the handle. A constant load of approximately 120# was used with the optimized motor, drive train, bevel gear, and rack and pinion and it was discovered that use of 4 cells resulted in an almost 5 second time period for moving the rack 60 mm. With 5 cells, the time was reduced to approximately 3.5 seconds. With a 6-cell configuration, the time was 2.5 seconds. Thus, interpolating this curve resulted in a minimum cell configuration of 5.5 cells. Due to the fact that cells only can be supplied in integer amounts, it was discovered that the 6-cell configuration was needed to meet the requirements provided for the electric stapling device.

From this, the minimum power source volume could be calculated as a fixed value, unless different sized cells could be used that provided the same electrical power characteristics. Lithium cells referred as CR2s have similar electrical power characteristics as have CR123s but are smaller. Therefore, using a 6-cell power supply of CR2s reduced the space requirement by more than 17%.

As set forth in detail above, the power source (i.e., batteries), drive train, and motor are optimized for total efficiency to deliver the desired output force within the required window of time for completing the surgical procedure. The efficiency of each kind of power source, drive train, and motor was examined and, thereafter, the type of power source, drive train, and motor was selected based upon this examination to deliver the maximum power over the desired time period. In other words, the maximum-power condition (voltage and current) is examined that can exist for a given period of time without activating the PTC (e.g., approximately 15 seconds). The present invention locates the voltage-current-power value that optimizes the way in which power is extracted from the cells to drive the motor. Even after such optimization, other changes can be made to improve upon the features of the electric stapler 1.

Another kind of power supply can be used and is referred to herein as a "hybrid" cell. In such a configuration, a rechargeable Lithium-ion or Lithium-polymer cell is connected to one or more of the optimized cells mentioned above (or perhaps another primary cell of smaller size but of a similar or higher voltage). In such a configuration, the Li-ion cell would power the stapling/cutting motor because the total energy contained within one CR2 cell is sufficient to recharge the Li ion cell many times, however, the primary cells are limited as to delivery. Li-ion and Li-Polymer cells have very low internal resistance and are capable of very high currents over short durations. To harness this beneficial behavior, a primary cell (e.g., CR123, CR2, or another cell) could take 10 to 30 seconds to charge up the secondary cell, which would form an additional power source for the motor during firing. An alternative embodiment of the Li-ion cell is the use of a capacitor; however, capacitors are volume inefficient. Even so, a super capacitor may be put into the motor powering system; it may be disconnected electrically therefrom until the operator determines that additional power is required. At such a time, the operator would connect the capacitor for an added "boost" of energy.

As mentioned above, if the load on the motor increases past a given point, the efficiency begins to decrease. In such a situation, a multi-ratio transmission can be used to change the delivered power over the desired time period. When the load becomes too great such that efficiency decreases, a multi-ratio transmission can be used to switch the gear ration to return the motor to the higher efficiency point, at which, for example, at least a 180# force can be supplied. It is noted, however, that the motor of the present invention needs to operate in both forward and reverse directions. In the latter operating mode, the motor must be able to disengage the stapling/cutting instrument from out of a "jammed" tissue clamping situation. Thus, it would be beneficial for the reverse gearing to generate more force than the forward gearing.

With significantly varying loads, e.g., from low pounds up to 180 pounds, there is the possibility of the drive assembly being too powerful in the lower end of the load range. Thus, the invention can include a speed governing device. Possible governing devices include dissipative (active) governors and passive governors. One exemplary passive governor is a flywheel, such as the energy storage element 56, 456 disclosed in U.S. Patent Application No. 2005/0277955 to Palmer et al. Another passive governor that can be used is a "fly" paddlewheel. Such an assembly uses wind resistance to govern speed because it absorbs more force as it spins faster and, therefore, provides a speed governing characteristic when the motor is moving too fast. Another kind of governor can be a compression spring that the motor compresses slowly to a compressed state. When actuation is desired, the compressed spring is released, allowing all of the energy to be transferred to the drive in a relatively short amount of time. A further exemplary governor embodiment can include a multi-stage switch having stages that are connected respectively to various sub-sets of the battery cells. When low force is desired, a first switch or first part of a switch can be activated to place only a few of the cells in the power supply circuit. As more power is desired, the user (or an automated computing device) can place successive additional cells into the power supply circuit. For example, in a 6-cell configuration, the first 4 cells can be connected to the power supply circuit with a first position of a switch, the fifth cell can be connected with a second position of the switch, and the sixth cell can be connected with a third position of the switch.

Electric motors and the associated gear box produce a certain amount of noise when used. The stapler of the present invention isolates the motor and/or the motor drive train from the handle to decrease both the acoustic and vibration characteristics and, thereby, the overall noise produced during operation. In a first embodiment, a dampening material is disposed between the handle body and both of motor and the drive train. The material can be foam, such as latex, polyester, plant-based, polyether, polyetherimide, polyimide, polyolefin, polypropylene, phenolic, polyisocyanates, polyurethane, silicone, vinyl, ethylene copolymer, expanded polyethylene, fluoropolymer, or styrofoam. The material can be an elastomer, such as silicone, polyurethane, chloroprene, butyl, polybutadiene, neoprene, natural rubber, or isoprene. The foam can be closed cellular, open cellular, flexible, reticular, or syntactic, for example. The material can be placed at given positions between the handle and motor/gear box or can entirely fill the chamber surrounding the motor/gear box. In a second embodiment, the motor and drive train are isolated within a nested box configuration, sometimes referred to as a "Chinese Box" or "Russian nesting doll." In such a configuration, the dampening material is placed around the motor/gear box and the two are placed within a first box with the gear box shaft protruding therefrom. Then, the first box is mounted within the "second box"—the handle body—and the dampening material is place between the first box and the handle interior.

The electric stapler of the present invention can be used in surgical applications. Most stapling devices are one-time use. They can be disposed after one medical procedure because the cost is relatively low. The electric surgical stapler, however, has a greater cost and it may be desirable to use at least the handle for more than one medical procedure. Accordingly, sterilization of the handle components after use becomes an issue. Sterilization before use is also significant. Because the electric stapler includes electronic components that typically do not go through standard sterilization processes (i.e., steam or gamma radiation), the stapler needs to be sterilized by other, possibly more expensive, means such as ethylene-oxide gas. It would be desirable, however, to make the stapler available to gamma radiation sterilization to reduce the cost associated with gas sterilization. It is known that electronics are usable in space, which is an environment where such electronics are exposed to gamma radiation. In such applications, however, the electronics need to work while being exposed. In contrast, the electric stapler does not need to work while being exposed to the gamma sterilization radiation. When semiconductors are employed, even if the power to the electronics is turned off, gamma radiation will adversely affect the stored memory. These components only need to withstand such radiation and, only after exposure ceases, need to be ready for use. Knowing this, there are various measures that can be taken to gamma-harden the electronic components within the handle. First, instead of use MOSFET memory, for example, fusable link memories can be used. For such memories, once the fuses are programmed (i.e., burnt), the memory becomes permanent and resistant to the gamma sterilization. Second, the memory can be mask-programmed. If the memory is hard programmed using masks, gamma radiation at the level for medical sterilization will not adversely affect the programming. Third, the sterilization can be performed while the volatile memory is empty and, after sterilization, the memory can be programmed through various measures, for example, a wireless link including infrared, radio, ultrasound, or Bluetooth communication can be used. Alternatively, or additionally, external electrodes can be contacted in a clean environment and these conductors can program the memory. Finally, a radiopaque shield (made from molybdenum or tungsten, for example) can be provided around the gamma radiation sensitive components to prevent exposure of these components to the potentially damaging radiation.

As set forth herein, characteristics of the battery, drive train, and motor are examined and optimized for an electric stapling application. The particular design (i.e., chemistry and PTC) of a battery will determine the amount of current that can be supplied and/or the amount of power that can be generated over a period of time. It has been determined that standard alkaline cells do not have the ability to generate the high power needed over the short period of time to effect actuation of the electric stapling device. It was also determined that some lithium-manganese dioxide cells also were unable to meet the needs for actuating the stapling device. Therefore, characteristics of certain lithium-manganese dioxide cell configurations were examined, such as the electrolyte and the positive temperature coefficient device.

It is understood that conventional lithium-manganese dioxide cells (e.g., CR123 and CR2) are designed for loads over a long period of time. For example, SUREFIRE® markets flashlights and such cells and states that the cells will last for from 20 minutes to a few hours (3 to 6) at the maximum lumen output of the flashlight. Load upon the cells(s) during this period of time is not close to the power capacity of the battery(ies) and, therefore, the critical current rate of the battery(ies) is not reached and there is no danger of overheating or explosion. If such use is not continuous, the batteries can last through many cycles (i.e., hundreds) at this same full power output.

Simply put, such batteries are not designed for loads over a period of 10 seconds or less, for example, five seconds, and are also not designed for a small number of uses, for example, ten to fifteen. What the present invention does is to configure the power supply, drive train, and motor to optimize the power supply (i.e., battery) for a small number of uses with each use occurring over a period of less than ten seconds and at a load that is significantly higher than rated.

All of the primary lithium cells that were examined possess a critical current rate defined by the respective PTC device and/or the chemistry and internal construction. If used above the critical current rate for a period of time, the cells can overheat and, possibly, explode. When exposed to a very high power demand (close to the PTC threshold) with a low number of cycles, the voltage and amperage profiles do not behave the same as in prior art standard uses. It has been found that some cells have PTC devices that prevent generation of power required by the stapler of the present invention, but that other cells are able to generate the desired power (can supply the current an voltage) for powering the electric stapling device. This means that the critical current rate is different depending upon the particular chemistry, construction, and/or PTC of the cell.

The present invention configures the power supply to operate in a range above the critical current rate, referred to herein as the "Super-Critical Current Rate." It is noted within the definition of Super-Critical Current Rate also is an averaging of a modulated current supplied by the power supply that is above the critical current rate. Because the cells cannot last long while supplying power at the Super-Critical Current Rate, the time period of their use is shortened. This shortened time period where the cells are able to operate at the Super-Critical Current Rate is referred to herein as the "Super-Critical Pulse Discharge Period," whereas the entire time when the power supply is activated is referred to as a "Pulse Discharge Period." In other words, the Super-Critical Pulse Discharge Period is a time that is less than or equal to the Pulse Discharge Period, during which time the current rate is greater than the critical current rate of the cells. The Super-Critical Pulse Discharge Period for the present invention is less than about 16 seconds, in other words, in a range of about one-half to fifteen seconds, for example, between two and four seconds and, more particularly, at about three seconds. During the life of the stapling device, the power supply may be subjected to the Super-Critical Current Rate over the Pulse Discharge Period for at least one time and less than twenty times within the time of a clinical procedure, for example, between approximately five and fifteen times, in particular, between ten and fifteen times within a period of five minutes. Therefore, in comparison to the hours of use for standard applications of the power supply, the present invention will have an aggregate use, referred to as the Aggregate Pulse Time, of, at most, approximately 200 to 300 seconds, in particular, approximately 225 seconds. It is noted that, during an activation, the device may not be required to exceed or to always exceed the Super-Critical Current Rate in a given procedure because the load presented to the instrument is dependent upon the specific clinical application (i.e., some tissue is denser than others and increased tissue density will increase load presented to device). However, the stapler is designed to be able to exceed the Super-Critical Current Rate for a number of times during the intended use of the surgical procedure. Acting in this Super-Critical Pulse Discharge Period, the device can operate a sufficient amount of times to complete the desired surgical procedure, but not many more because the power supply is asked to perform at an increased current.

Figure 32:
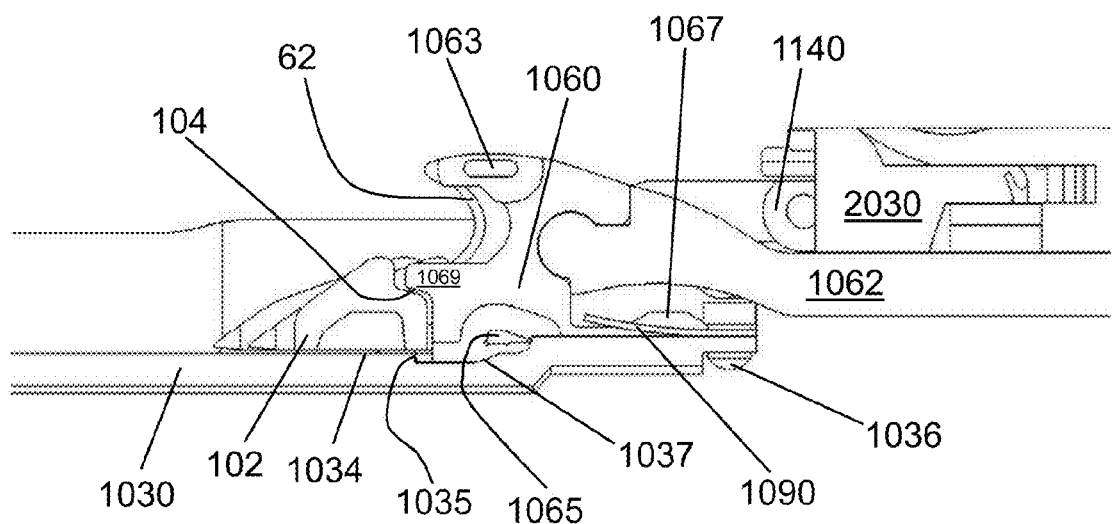
FIG. 32 is a fragmentary, vertically longitudinal, cross-sectional view of a distal end of an articulating portion of an exemplary embodiment of an end effector with the inner tube, the pushrod-blade support, the anvil, the closure ring, and the near half of the staple sled removed.

When performing in the increased range, the force generated by the device, e.g., the electric stapler 1, is significantly greater than existed in a hand-powered stapler. In fact, the force is so much greater that it could damage the stapler itself. In one exemplary use, the motor and drive assemblies can be operated to the detriment of the knife blade lock-out feature—the safety that prevents the knife blade 1060 from advancing when there is no staple cartridge or a previously fired staple cartridge in the staple cartridge holder 1030. This feature is illustrated in FIG. 32. As discussed, the knife blade 1060 should be allowed to move distally only when the staple sled 102 is present at the firing-ready position, i.e., when the sled 102 is in the position illustrated in FIG. 32. If the sled 102 is not present in this position, a fixed number of possibilities exist. One possible situation can be that there is no staple cartridge in the holder 1030. Another possible situation is that the staple cartridge is not properly installed in the holder 1030. A further possible situation can be that the sled 102 has already been moved distally—in other words, a partial or full firing has already occurred with a loaded staple cartridge. In some of these situations where the blade 1060 is in an unactuated position, the blade 1060 should not be allowed to move, or should be restricted in its movement. Accordingly, to insure that the sled 102 can prop up the blade 1060 when in a firing state, the sled 102 is provided with a lock-out contact surface 104 and the blade 1060 is provided with a correspondingly shaped contact nose 1069. It is noted at this point that, the lower guide wings 1065 do not rest against a floor 1034 in the cartridge holder 1030 until the blade 1060 has moved distally past an edge 1035. With such a configuration, if the sled 102 is not present at the distal end of the blade 1060 to prop up the nose 1069, then the lower guide wings 1065 will follow the depression 1037 just proximal of the edge 1035 and, instead of advancing on the floor 1034, will hit the edge 1035 and prevent further forward movement of the blade 1060. To assist with such contact when the sled 102 is not present (referred to as a "lock out"), the staple cartridge 1030 has a plate spring 1090 (attached thereto by at least one rivet 1036) for biasing the blade 1060. With the plate spring 1090 flexed upward and pressing downward against the flange 1067 (at least until the flange 1067 is distal of the distal end of the plate spring 1090), a downwardly directed force is imparted against the blade 1060 to press the wings 1065 down into the depression 1037. Thus, as the blade 1060 advances distally without the sled 102 being present, the wings 1065 follow the lower curve of the depression 1037 and are stopped from further distal movement when the distal edge of the wings 1065 hit the edge 1035.

Figure 33:
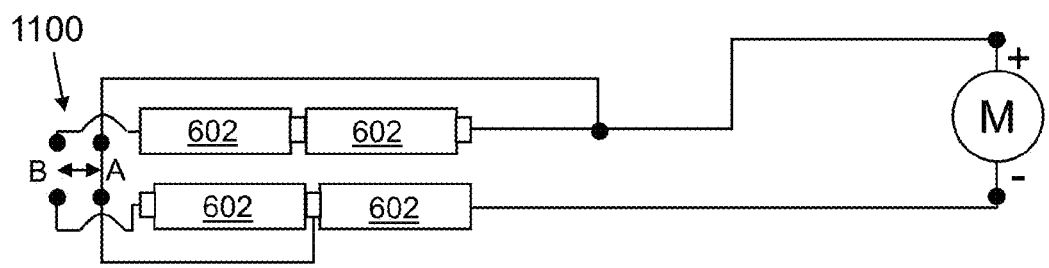
FIG. 33 is a schematic circuit diagram of an exemplary switching assembly for a power supply according to the invention.

This safety feature operates as described so long as the force transmitted by the knife blades 1062 to the blade 1060 is not great enough to tear off the lower guide wings 1065 from the blade 1060. With the forces able to be generated by the power supply, motor and drive train of the present invention, the blade 1060 can be pushed distally so strongly that the wings 1065 are torn away. If this occurs, there is no way to prevent distal movement of the blade 1060 or the sled 102. Accordingly, the present invention provides a way to lower the forces able to be imparted upon the wings 1065 prior to their passage past the edge 1035. In other words, the upper limit of force able to be applied to the blade 1060 is reduced in the first part of blade travel (past the edge 1035) and increases after the wings 1065 have cleared the edge 1035 and rest on the floor 1034. More specifically, a first exemplary embodiment of this two-part force generation limiter takes the form of a circuit in which only one or a few of the cells in the power supply are connected to the motor during the first part of the stapling/cutting stroke and, in the second part of the stapling/cutting stroke, most or all of the cells in the power supply are connected to the motor. A first exemplary form of such a circuit is illustrated in FIG. 33. In this first embodiment, when the switch 1100 is in the "A" position, the motor (e.g., stapling motor 210) is only powered with one power cell 602 (of a possible four in this exemplary embodiment). However, when the switch 1100 is in the "B" position, the motor is powered with all four of the cells 602 of the power supply 600, thereby increasing the amount of force that can be supplied to the blade 1060. Control of the switch 1100 between the A and B positions can occur by positioning a second switch somewhere along the blade control assembly or along the sled 102, the second switch sending a signal to a controller after the wings 1065 have passed the edge 1035. It is noted that this first embodiment of the control circuit is only exemplary and any similarly performing assembly can provide the lock-out protection for the device, see, for example, the second exemplary embodiment illustrated in FIG. 35.

Figure 34:
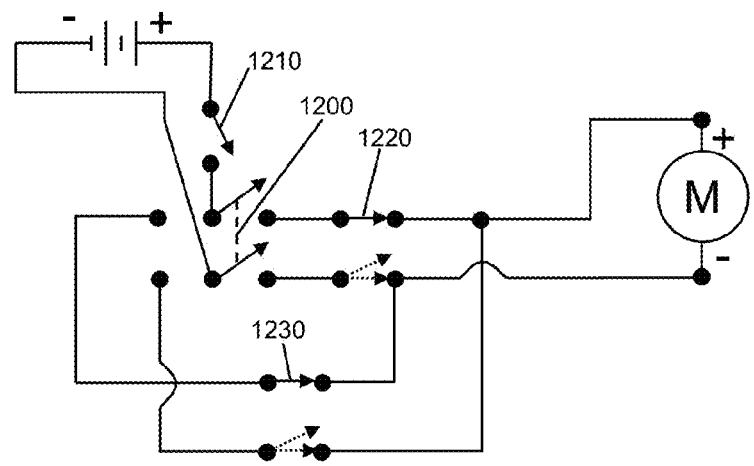
FIG. 34 is a schematic circuit diagram of an exemplary switching assembly for forward and reverse control of a motor according to the invention.

A first exemplary form of a forward and reverse motor control circuit is illustrated in FIG. 34. This first exemplary embodiment uses a double-throw, double pole switch 1200. The switch 1200 is normally spring-biased to a center position in which both poles are off. The motor M illustrated can, for example, represent the stapling motor 210 of the present invention. As can be seen, the power-on switch 1210 must be closed to turn on the device. Of course, this switch is optional. When a forward movement of the motor M is desired, the switch 1200 is placed in the right position as viewed in FIG. 34, in which power is supplied to the motor to run the motor in a first direction, defined as the forward direction here because the "+" of the battery is connected to the "+" of the motor M. In this forward switching position, the motor M can power the blade 1060 in a distal direction. Placement of an appropriate sensor or switch to indicate the forward-most desired position of the blade 1060 or the sled 102 can be used to control a forward travel limit switch 1220 that interrupts power supply to the motor M and prevents further forward travel, at least as long as the switch 1220 remains open. Circuitry can be programmed to never allow this switch 1220 to close and complete the circuit or to only allow resetting of the switch 1220 when a new staple cartridge, for example, is loaded.

When a reverse movement of the motor M is desired, the switch 1200 is placed in the left position as viewed in FIG. 34, in which power is supplied to the motor to run the motor in a second direction, defined as the reverse direction here because the "−" of the battery is connected to the "+" of the motor M. In this reverse switching position, the motor M can power the blade 1060 in a proximal direction. Placement of an appropriate sensor or switch to indicate the rearward-most desired position of the blade 1060 or the sled 102 can be used to control a rearward travel limit switch 1230 that interrupts power supply to the motor M and prevents further rearward travel, at least as long as the switch 1230 remains open. It is noted that other switches (indicated with dotted arrows) can be provided in the circuit to selectively prevent movement in either direction independent of the limit switches 1220, 1230.

It is noted that the motor can power the gear train with a significant amount of force, which translates into a high rotational inertia. As such, when any switch mentioned with respect to FIGS. 33 and 34 is used to turn off the motor, the gears may not just stop. Instead, the rotational inertia continues to propel, for example, the rack 217 in the direction it was traveling when power to the motor was terminated. Such movement can be disadvantageous for many reasons. By configuring the power supply and motor appropriately, a circuit can be formed to substantially eliminate such post-termination movement, thereby giving the user more control over actuation.

Figure 35:
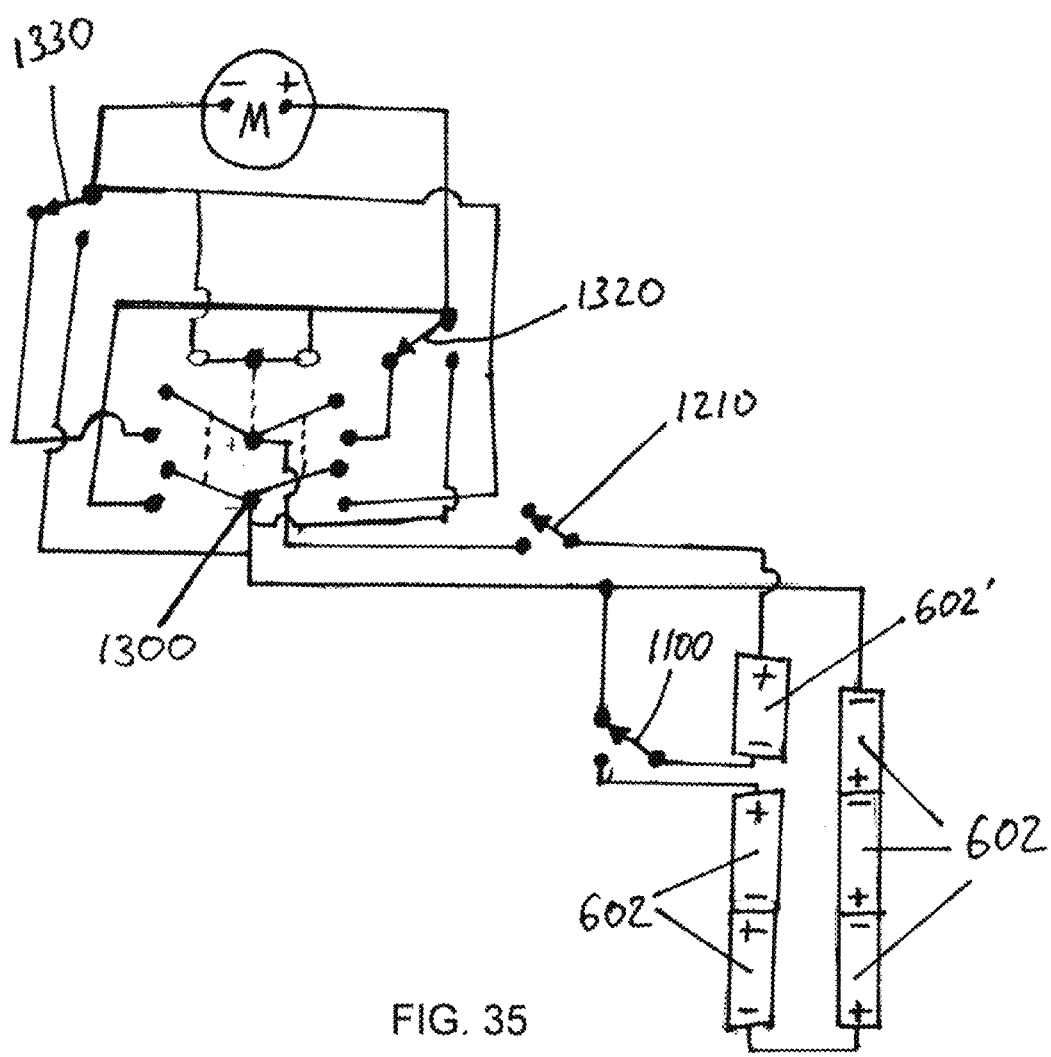
FIG. 35 is a schematic circuit diagram of another exemplary switching assembly for the power supply and the forward and reverse control of the motor according to the invention.

FIG. 35 illustrates an exemplary embodiment where the motor (for example, stapling motor 210) is arrested from further rotation when forward or reverse control is terminated. FIG. 35 also illustrates alternative embodiments of the forward/reverse control and of the multi-stage power supply. The circuit of FIG. 35 has a motor arrest sub-circuit utilizing a short-circuit property of an electrical motor. More specifically, the electrical motor M is placed into a short-circuit so that an electrically generated magnetic field is created in opposition to the permanent magnetic field, thus slowing the still-spinning motor at a rate that substantially prevents inertia-induced over-stroke. To explain how the circuit of FIG. 35 can brake the motor M, an explanation of the forward/reverse switch 1300 is provided. As can be seen, the forward/reverse switch 1300 has three positions, just like the switch 1200 of FIG. 34. When placed in the right position, the motor M is actuated in a forward rotation direction. When placed in the left position, the motor M is actuated in a rearward rotation direction. When the switch 1300 is not actuated—as shown in FIG. 35—the motor M is short circuited. This short circuit is diagrammatically illustrated by the upper portion of the switch 1300. It is noted that the switching processes in a braking switch is desired to take place in a time-delayed manner, which is also referred to as a break-before-make switching configuration. When switching over from operating the motor M to braking the motor M, the double-pole, double throw portion of the forward/reverse switch 1300 is opened before the motor short circuit is effected. Conversely, when switching over from braking the motor M to operating the motor M, the short circuit is opened before the switch 1300 can cause motor actuation. Therefore, in operation, when the user releases the 3-way switch 1300 from either the forward or reverse positions, the motor M is short-circuited and brakes quickly.

Other features of the circuit in FIG. 35 have been explained with regard to FIG. 34. For example, an on/off switch 1210 is provided. Also present is the power lock-out switch 1100 that only powers the motor with one power cell 602' in a given portion of the actuation (which can occur at the beginning or at any other desired part of the stroke) and powers the motor M with all of the power cells 602 (here, for example, six power cells) in another portion of the actuation.

A new feature of the reverse and forward limit switches 1320, 1330 prevents any further forward movement of the motor M after the forward limit switch 1320 is actuated. When this limit is reached, the forward limit switch 1320 is actuated and the switch moves to the second position. In this state, no power can get to the motor for forward movement but power can be delivered to the motor for reverse movement. The forward limit switch can be programmed to toggle or be a one-time use for a given staple cartridge. More specifically, the switch 1320 will remain in the second position until a reset occurs by replacing the staple cartridge with a new one. Thus, until the replacement occurs, the motor M can only be powered in the reverse direction. If the switch is merely a toggle, then power can be restored for additional further movement only when the movement has retreated the part away from actuating the switch 1320.

The reverse limit switch 1330 can be configured similarly. When the reverse limit is reached, the switch 1330 moves to the second position and stays there until a reset occurs. It is noted that, in this position, the motor M is in a short-circuit, which prevents motor movement in either direction. With such a configuration, the operation of the stapler can be limited to a single stroke up to the forward limit and a single retreat up to the rear limit. When both have occurred, the motor M is disabled until the two switches 1320 are reset.

The foregoing description and accompanying drawings illustrate the principles, preferred embodiments and modes of operation of the invention. More specifically, the optimized power supply, motor, and drive train according to the present invention has been described with respect to a surgical stapler. However, the invention should not be construed as being limited to the particular embodiments discussed above. Additional variations of the embodiments discussed above will be appreciated by those skilled in the art as well as for applications, unrelated to surgical devices, that require an advanced power or current output for short and limited durations with a power cell having a limited power or current output. As is shown and described, when optimized according to the present invention, a limited power supply can produce lifting, pushing, pulling, dragging, retaining, and other kinds of forces sufficient to move a substantial amount of weight, for example, over 82 kg.

The above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A surgical instrument, comprising:
 a surgical end effector having at least one actuation assembly to effect a surgical procedure when actuated;
 a handle mechanically coupled with the end effector and having a shell;
 an electric motor disposed within the shell and having:
  motor terminals; and
  a drive train operatively coupled to the at least one actuation assembly to actuate the at least one actuation assembly when the motor is supplied with power;
 a power supply having power terminals; and
 a selective switching connection disposed within the shell and having a break-before-make switch with three positions including a forward position, a reverse position, and an off position, the selective switching connection:
  in the forward position, electrically connecting the power terminals to the motor terminals to power the motor in a forward direction;
  in the reverse position, electrically connecting the power terminals to the motor terminals to power the motor in a reverse direction; and
  in the off position, electrically separating at least one of the power terminals from the motor terminals.

2. The instrument according to claim 1, wherein:
 the power supply is a removable battery pack and has two power terminals; and
 the switch of the selective switching connection is a double-pole/double-throw, break-before-make switch with three positions including the forward position, the reverse position, and the off position, and:
  in the forward position, electrically connects the two power terminals to the two motor terminals to power the motor in a forward direction;
  in the reverse position, electrically connects the two power terminals to the two motor terminals to power the motor in a reverse direction; and
  in the off position, electrically separates at least one of the two power terminals from the two motor terminals.

3. The instrument according to claim 1, wherein the end effector, handle, motor, and selective switching connection are all operable with only a single hand.

4. The instrument according to claim 1, wherein the end effector is a surgical stapling endocutter.

5. The instrument according to claim 1, wherein:
 the motor has a permanent magnetic field; and
 at least one of the motor, the drive train, and the actuation assembly has an inertia-induced over-stroke characteristic after powered operation.

6. The instrument according to claim 5, further comprising a post-termination braking circuit having the selective switching connection as a component thereof, the post-termination braking circuit electrically short-circuiting the motor terminals with the off position of the switch.

7. The instrument according to claim 1, wherein:
 the drive train has a rotational inertia when operating; and
 the motor has:
  a rotational inertia when spinning; and
  a permanent magnetic field.

8. The instrument according to claim 7, further comprising a post-termination braking circuit having the selective switching connection as a component thereof, the post-termination braking circuit operable to create an electrically-generated magnetic field in opposition to the permanent magnetic field with the rotational inertia of at least one of the drive train and the motor when short-circuiting the motor terminals with the off position of the switch.

9. A surgical instrument, comprising:
 a surgical end effector having at least one actuation assembly to effect a surgical procedure when actuated;
 a handle mechanically coupled with the end effector and having a shell;
 an electric motor disposed within the shell and having:
  motor terminals; and
  a drive train operatively coupled to the at least one actuation assembly to actuate the at least one actuation assembly when the motor is supplied with power;
 a power supply having power terminals; and
 a post-termination braking circuit:
  having a selective switching connection disposed within the shell and having a break-before-make switch with three positions including a forward position, a reverse position, and an off position, the selective switching connection:
   in the forward position, electrically connecting the power terminals to the motor terminals to power the motor in a forward direction;
   in the reverse position, electrically connecting the power terminals to the motor terminals to power the motor in a reverse direction; and
   in the off position, electrically separating at least one of the power terminals from the motor terminals; and
  electrically short-circuiting the motor terminals with the off position of the switch.

10. The instrument according to claim 9, wherein:
 the power supply is a removable battery pack and has two power terminals; and
 the switch of the selective switching connection is a double-pole/double-throw, break-before-make switch with three positions including the forward position, the reverse position, and the off position, and:
  in the forward position, electrically connects the two power terminals to the two motor terminals to power the motor in a forward direction;
  in the reverse position, electrically connects the two power terminals to the two motor terminals to power the motor in a reverse direction; and
  in the off position, electrically separates at least one of the two power terminals from the two motor terminals.

11. The instrument according to claim 9, wherein:
 the motor has a permanent magnetic field; and
 at least one of the motor, the drive train, and the actuation assembly has an inertia-induced over-stroke characteristic after powered operation.

12. The instrument according to claim 11, wherein the inertia-induced over-stroke of at least one of the motor, the drive train, and the actuation assembly is counteracted with the short-circuit.

13. A surgical instrument, comprising:
a surgical end effector having at least one actuation assembly to effect a surgical procedure when actuated;
a handle mechanically coupled with the end effector and having a shell;
an electric motor disposed within the shell and having:
 a rotational inertia when spinning;
 a permanent magnetic field;
 motor terminals; and
 a drive train operatively coupled to the at least one actuation assembly to actuate the at least one actuation assembly when the motor is supplied with power, the drive train having a rotational inertia when operating;
a power supply having power terminals; and
a post-termination braking circuit:
 having a selective switching connection disposed within the shell and having a break-before-make switch with three positions including a forward position, a reverse position, and an off position, the selective switching connection:
  in the forward position, electrically connecting the power terminals to the motor terminals to power the motor in a forward direction;
  in the reverse position, electrically connecting the power terminals to the motor terminals to power the motor in a reverse direction; and
  in the off position, electrically separating at least one of the power terminals from the motor terminals;
 electrically short-circuiting the motor terminals with the off position of the switch; and
 being operable to create an electrically-generated magnetic field in opposition to the permanent magnetic field with the rotational inertia of at least one of the drive train and the motor when short-circuiting the motor terminals with the off position of the switch.

14. The instrument according to claim 13, wherein:
the power supply is a removable battery pack and has two power terminals; and
the switch of the selective switching connection is a double-pole/double-throw, break-before-make switch with three positions including the forward position, the reverse position, and the off position, and:
 in the forward position, electrically connects the two power terminals to the two motor terminals to power the motor in a forward direction;
 in the reverse position, electrically connects the two power terminals to the two motor terminals to power the motor in a reverse direction; and
 in the off position, electrically separates at least one of the two power terminals from the two motor terminals.

* * * * *